United States Patent
Baker et al.

(10) Patent No.: US 6,194,458 B1
(45) Date of Patent: Feb. 27, 2001

(54) BENZAMIDE POTASSIUM CHANNEL INHIBITORS

(75) Inventors: Robert K. Baker, Cranford; Jianming Bao, Scotch Plains; Frank Kayser, Hoboken; Andrew Kotliar, Highland Park; William H. Parsons, Belle Mead; Kathleen M. Rupprecht, Cranford, all of NJ (US); Christopher F. Claiborne, Lansdale, PA (US); David A. Claremon, Maple Glen, PA (US); Nigel Liverton, Harleysville, PA (US); Wayne J. Thompson, Lansdale, PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/422,499

(22) Filed: Oct. 21, 1999

Related U.S. Application Data

(60) Provisional application No. 60/106,422, filed on Oct. 30, 1998.

(51) Int. Cl.[7] .................. A61K 31/22; A61K 31/165; A61K 31/34; C07C 261/00; C07C 233/00
(52) U.S. Cl. ................ 514/549; 514/551; 514/617; 514/469; 560/32; 564/185; 549/468
(58) Field of Search ............... 564/185; 514/551, 514/549, 617, 469; 560/32; 549/468

(56) References Cited

U.S. PATENT DOCUMENTS

| | | | |
|---|---|---|---|
| 5,135,949 | * | 8/1992 | Von Der Saal et al. ......... 514/520 |
| 5,141,955 | * | 8/1992 | Evers et al. ................. 514/466 |
| 5,312,031 | * | 5/1994 | Dugar ....................... 514/278 |
| 5,340,827 | * | 8/1994 | Beely et al. ................. 514/352 |
| 5,618,938 | | 4/1997 | Emonds-Alt et al. . |
| 5,985,881 | * | 11/1999 | Dollinger et al. ............. 514/255 |
| 6,040,339 | * | 3/2000 | Yoshida et al. ............... 514/485 |
| 6,054,457 | * | 4/2000 | Setoi et al. .................. 514/255 |

FOREIGN PATENT DOCUMENTS

| | | |
|---|---|---|
| WO 98/04521 | 10/1988 | (EP). |
| 0 317 321 A2 | 5/1989 | (EP). |
| 0 472 053 A2 | 2/1992 | (EP). |
| WO 96/21640 | 7/1976 | (WO). |
| WO 98/04135 | 2/1998 | (WO). |

OTHER PUBLICATIONS

Ott, et al., J. Med. Chem., vol. 11, pp. 777–787, 1968.
Avetisyan, et al., Arm. Khim, Zh., vol. 34(12), pp. 1007–1010, 1981 (attached English Abstract).

* cited by examiner

Primary Examiner—Deborah C. Lambkin
(74) Attorney, Agent, or Firm—Soonhee Jang; J. Antonio Garcia-Rivas; Mark R. Daniel

(57) ABSTRACT

This invention relates to benzamide potassium channel inhibitors of general structural Formula I.

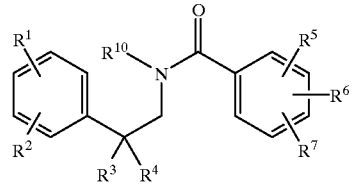

The compounds of this invention are useful in the treatment of autoimmune diseases, the prevention of rejection of foreign organ transplants and related afflictions, diseases and illnesses, and cardiac arrhythmias. Also within the scope of this invention are pharmaceutical formulations comprising a compound of Formula I and a pharmaceutical carrier, as well as pharmaceutical formulations comprising a compound of Formula I, one or more immunosuppressive compounds and a pharmaceutical carrier.

19 Claims, No Drawings

BENZAMIDE POTASSIUM CHANNEL INHIBITORS

RELATED APPLICATIONS

This application claims priority under 35 U.S.C. § 119(e) from U.S. Provisional Application 60/106,422 filed Oct. 30, 1998.

BACKGROUND OF THE INVENTION

The present invention relates to a class of compounds that are useful as potassium channel inhibitors to treat autoimmune disorders, cardiac arrhythmias, and the like.

Immunoregulatory abnormalities have been shown to exist in a wide variety of autoimmune and chronic inflammatory diseases, including systemic lupus erythematosis, chronic rheumatoid arthritis, type I and II diabetes mellitus, inflammatory bowel disease, biliary cirrhosis, uveitis, multiple sclerosis and other disorders such as Crohn's disease, ulcerative colitis, bullous pemphigoid, sarcoidosis, psoriasis, ichthyosis, Graves ophthalmopathy and asthma.

Although the underlying pathogenesis of each of these conditions may be quite different, they have in common the appearance of a variety of autoantibodies and self-reactive lymphocytes. Such self-reactivity may be due, in part, to a loss of the homeostatic controls under which the normal immune system operates. Similarly, following a bone-marrow or an organ transplantation, the host lymphocytes recognize the foreign tissue antigens and begin to produce antibodies which lead to graft rejection.

One end result of an autoimmune or a rejection process is tissue destruction caused by inflammatory cells and the mediators they release. Anti-inflammatory agents such as NSAID's act principally by blocking the effect or secretion of these mediators but do nothing to modify the immunologic basis of the disease. On the other hand, cytotoxic agents, such as cyclophosphamide, act in such a nonspecific fashion that both the normal and autoimmune responses are shut off. Indeed, patients treated with such nonspecific immunosuppressive agents are as likely to succumb from infection as they are from their autoimmune disease.

Cyclosporin A (CsA), which was approved by the US FDA in 1983 is currently the leading drug used to prevent rejection of transplanted organs. In 1993, FK-506 (Prograf) was approved by the US FDA for the prevention of rejection in liver transplantation. CsA and FK-506 act by inhibiting the body's immune system from mobilizing its vast arsenal of natural protecting agents to reject the transplant's foreign protein. In 1994, CsA was approved by the US FDA for the treatment of severe psoriasis and has been approved by European regulatory agencies for the treatment of atopic dermatitis. Though they are effective in fighting transplant rejection, CsA and FK-506 are known to cause several undesirable side effects including nephrotoxicity, neurotoxicity, and gastrointestinal discomfort. Therefore, a selective immunossuppressant without these side effects still remains to be developed. Potassium channel inhibitors promise to be the solution to this problem.

The importance of potassium channels was first recognized almost fifty years ago when Hodgkin and Huxley discovered that potassium ions contributed to the current that excited the squid giant. Research in the area, however, was hampered by the lack of selective, high affinity ligands for potassium channels. But the advent of recombinant DNA techniques and single cell and whole cell voltage clamp techniques has changed the slow pace of the field. Potassium channels have turned out to be the most diverse family of ion channels discovered to date. They modulate a number of cellular events such as muscle contraction, neuro-endocrine secretion, frequency and duration of action potentials, electrolyte homeostasis, and resting membrane potential.

Potassium channels have been classified according to their biophysical and pharmacological characteristics. Salient among these are the voltage dependent potassium channels, such as $K_v1$. The $K_v1$ class of potassium channels is further subdivided depending on the molecular sequence of the channel, for example $K_v1.1$, $K_v1.3$, $K_v1.5$. Functional voltage-gated $K^+$ channels can exist as multimeric structures formed by the association of either identical or dissimilar subunits. This phenomena is thought to account for the wide diversity of $K^+$ channels. However, subunit compositions of native $K^+$ channels and the physiologic role that particular channels play are, in most cases, still unclear.

Membrane depolarization by $K_v1.3$ inhibition has been shown to be an effective method to prevent T-cell proliferation and therefore has applications in many autoimmune conditions. Inhibition of $K^+$ channels in the plasma membrane of human T-lymphocytes has been postulated to play a role in eliciting immunosuppressive responses by regulating intracellular $Ca^{++}$ homeostasis, which has been found to be important in T-cell activation.

The $K_v1.3$ voltage-gated potassium channel is found in neurons, blood cells, osteoclasts and T-lymphocytes. The Chandy and Cahalan laboratories proposed a hypothesis that blocking the $K_v1.3$ channel would elicit an immunosuppressant response. (Chandy et al., *J. Exp. Med.* 160, 369, 1984; Decoursey et al., Nature, 307, 465, 1984). However, the K+ channel blockers employed in their studies were non-selective. Until research with the peptide margatoxin, a peptide found in scorpion venom, no specific inhibitor of the $K_v1.3$ channel existed to test this hypothesis. Although a laboratory (Price et al., *Proc. Natl. Acad. Sci.* USA, 86, 10171, 1989) showed that charybdotoxin would block $K_v1.3$ in human T cells, charybdotoxin was subsequently shown to inhibit four different $K^+$ channels ($K_v1.3$ and three distinct small conductance $Ca^{++}$ activated $K^+$ channels) in human T-lymphocytes, limiting the use of this toxin as a probe for the physiological role of $K_v1.3$ (Leonard et al., *Proc. Natl. Acad. Sci.* USA, 89, 10094, 1992). Margatoxin, on the other hand, blocks only $K_v1.3$ in T-cells, and has immunosuppressant activity in both in vitro and in vivo models. (Lin et al., *J. Exp. Med,* 177, 637, 1993). The therapeutic utility of this compound, however, is limited by its potent toxicity. Recently, a class of compounds has been reported that may be an attractive alternative to the above-mentioned drugs, see for example U.S. Pat. Nos. 5,670,504; 5,631,282; 5,696,156; 5,679,705; and 5,696,156. While addressing some of the activity/toxicity problems of previous drugs, these compounds tend to be of large molecular weight and are generally produced by synthetic manipulation of a natural product, isolation of which is cumbersome and labor intensive.

The foregoing problems are solved to a large extent by the practice of the invention as herein disclosed for immunosuppression.

Atrial fibrillation (AF) is the most common sustained cardiac arrhythmia in clinical practice and is likely to increase in prevalence with the aging of the population. Currently, AF affects more than 1 million Americans annually, represents over 5% of all admissions for cardiovascular diseases and causes more than 80,000 strokes each year in the United States. While AF is rarely a lethal arrhythmia, it is responsible for substantial morbidity and can lead to complications such as the development of congestive heart failure or thromboembolism. Currently available Class I and Class III antiarrhythmic drugs reduce the rate of recurrence of AF, but are of limited use because of a variety of potentially adverse effects including ventricular proarrhythmia. Because current therapy is inadequate and fraught with side effects, there is a clear need to develop new therapeutic approaches.

Antiarrhythmic agents of Class III are drugs that cause a selective prolongation of the duration of the action potential without significant cardiac depression. Available drugs in this class are limited in number. Examples such as sotalol and amiodarone have been shown to possess interesting Class III properties (Singh B. N., Vaughan Williams E. M. "A Third Class Of Anti-Arrhythmic Action: Effects On Atrial And Ventricular Intracellular Potentials And Other Pharmacological Actions On Cardiac Muscle, of MJ 1999 and AH 3747" Br. *J. Pharmacol* 1970; 39:675–689. and Singh B. N., Vaughan Williams E. M, "The Effect Of Amiodarone, A New Anti-Anginal Drug, On Cardiac Muscle", Br *J. Pharmacol* 1970; 39:657–667.), but these are not selective Class III agents. Sotalol also possesses Class II effects which may cause cardiac depression and is contraindicated in certain susceptible patients. Amiodarone, also is not a selective Class III antiarrhythmic agent because it possesses multiple electrophysiological actions and is severely limited by side effects (Nademanee, K. "The Amiodarone Odessey". *J. Am. Coll. Cardiol.* 1992; 20:1063–1065.) Drugs of this class are expected to be effective in preventing ventricular fibrillation. Selective class III agents, by definition, are not considered to cause myocardial depression or an induction of arrhythmias due to inhibition of conduction of the action potential as seen with Class I antiarrhythmic agents.

Class III agents increase myocardial refractoriness via a prolongation of cardiac action potential duration. Theoretically, prolongation of the cardiac action potential can be achieved by enhancing inward currents (i.e. $Na^+$ or $Ca^{2+}$ currents; hereinafter $I_{Na}$ and $I_{Ca}$, respectively) or by reducing outward repolarizing potassium ($K^+$) currents. The delayed rectifier ($I_K$) $K^+$ current is the main outward current involved in the overall repolarization process during the action potential plateau, whereas the transient outward ($I_{to}$) and inward rectifier ($I_{K1}$) $K^+$ currents are responsible for the rapid initial and terminal phases of repolarization, respectively. Cellular electrophysiologic studies have demonstrated that $I_K$ consists of two pharmacologically and kinetically distinct $K^+$ current subtypes, $I_{Kr}$ (rapidly activating and deactivating) and $I_{Ks}$ (slowly activating and deactivating) (Sanguinetti and Jurkiewicz, Two Components Of Cardiac Delayed Rectifier K+ Current: Differential Sensitivity To Block By Class III Antiarrhythmic Agents, *J Gen Physiol* 1990, 96:195–215). Class III antiarrhythmic agents currently in development, including d-sotalol, dofetilide (UK-68,798), almokalant (H234/09), E-4031 and methanesulfonamide-N-[1'-6-cyano-1,2,3,4-tetrahydro-2-naphthalenyl)-3,4-dihydro-4-hydroxyspiro[2H-1-benzopyran-2,4'-piperidin]-6yl] monochloride, predominantly, if not exclusively, block $I_{Kr}$. Although, amiodarone is a blocker of $I_{Ks}$ (Balser J. R. Bennett, P. B., Hondeghem, L. M. and Roden, D. M. "Suppression Of Time-Dependent Outward Current In Guinea Pig Ventricular Myocytes: Actions Of Quinidine And Amiodarone. *Circ. Res.* 1991, 69:519–529), it also blocks $I_{Na}$ and $I_{Ca}$, effects thyroid function, is as a nonspecific adrenergic blocker, and acts as an inhibitor of the enzyme phospholipase (Nademanee, K. "The Amiodarone Odessey". *J. Am. Coll. Cardiol.* 1992; 20:1063–1065). Therefore, its method of treating arrhythmia is uncertain Most Class III agents that are known to be in development predominantly block $I_{Kr}$.

Reentrant excitation (reentry) has been shown to be a prominent mechanism underlying supraventricular arrhythmias in man. Reentrant excitation requires a critical balance between slow conduction velocity and sufficiently brief refractory periods to allow for the initiation and maintenance of multiple reentry circuits to coexist simultaneously and sustain AF. Increasing myocardial refractoriness by prolonging action potential duration (APD), prevents and/or terminates reentrant arrhythmias. Most selective Class III antiarrhythmic agents currently in development, such as d-sotalol and dofetilide predominantly, if not exclusively, block $I_{kr}$, the rapidly activating component of $I_K$ found both in atrium and ventricle in man.

Since these $I_{kr}$ blockers increase APD and refractoriness both in atria and ventricle without affecting conduction per se, theoretically they represent potential useful agents for the treatment of arrhythmias like AF. These agents have a liability in that they have an enhanced risk of proarrhythmia at slow heart rates. For example, torsades de points has been observed when these compounds are utilized (Roden, D. M. "Current Status of Class III Antiarrhythmic Drug Therapy", *Am J. Cardiol,* 1993; 72:44B–49B). This exaggerated effect at slow heart rates has been termed "reverse frequency-dependence", and is in contrast to frequency-independent or frequency-dependent actions (Hondeghem, L. M. "Development of Class III Antiarrhythmic Agents". *J. Cadiovasc. Cardiol.* 20 (Suppl. 2):S17–S22).

The slowly activating component of the delayed rectifier ($I_{ks}$) potentially overcomes some of the limitations of $I_{kr}$ blockers associated with ventricular arrhythmias. Because of its slow activation kinetics however, the role of $I_{ks}$ in atrial repolarization may be limited due to the relatively short APD of the atrium. Consequently, although $I_{ks}$ blockers may provide distinct advantage in the case of ventricular arrhythmias, their ability to affect SVT is considered to be minimal.

The ultra-rapidly activating delayed rectifier $K^+$ current ($I_{kur}$) is believed to represent the native counterpart to a cloned potassium channel designated Kv1.5 and, while present in human atrium, it appears to be absent in human ventricle. Furthermore, because of its rapidity of activation and limited slow inactivation, $I_{kur}$ is believed to contribute significantly to repolarization in human atrium. Consequently, a specific blocker of $I_{kur}$, that is a compound which blocks Kv1.5, would overcome the short coming of other compounds by prolonging refractoriness by retarding repolarization in the human atrium without causing the delays in ventricular reporlarization that underlie arrhythmogenic afterdepolarizations and acquired long QT syndrome observed during treatment with current Class III drugs.

In intact human atrial myocytes an ultra-rapidly activating delayed rectifier $K^+$ current $I_{kur}$ which is also known as the sustained outward current, $I_{SUS}$ or $I_{SO}$, has been identified and this current has properties and kinetics identical to those expressed by the human $K^+$ channel clone (hKv1.5, HK2) when isolated from human heart and stably expressed in human (HEK-293) cell lines. (Wang, Fermini and Natel, 1993, Circ Res 73:1061–1076; Fedida et al., 1993, Circ Res 73:210–216; Snyders, Tamkun and Bennet, 1993, J Gen Physiol 101:513–543) and originally cloned from rat brain (Swanson et al., 10, Neuron 4:929–939). Although various antiarrythmic agents are now available on the market, those having both satisfactory efficacy and a high margin of safety have not been obtained. For example, antiarrythmic agents of Class I according to the classification scheme of Vaughan-Williams ("Classification Of Antiarrhythmic Drugs" In: Cardiac Arrhythmias, edited by: E. Sandoe, E. Flensted-Jensen, K. Olesen; Sweden, Astra, Sodertalje, pp449–472, 1981) which cause a selective inhibition of the maximum velocity of the upstroke of the action potential ($_{max}$) are inadequate for preventing ventricular fibrillation. In addition, they have problems regarding safety, namely, they cause a depression of myocardial contractility and have a tendency to induce arrhythmias due to an inhibition of impulse conduction. Beta-adrenoceptor blockers and calcium antagonists which belong to Class II and IV, respectively, have a defect in that their effects are either limited to a certain type of arrhythmia or are contraindicated because of their cardiac depressant properties in certain patients with cardiovascular disease. Their safety, however, is higher than that of the antiarrhythmic agents of Class I.

The method of treatment of atrial arrhythmia presented herein provides for greater safety and efficacy as well preferentially providing treatment at fast heart rates when treatment of this type is most desired.

SUMMARY OF THE INVENTION

This invention relates to benzamide potassium channel inhibitors of general structural Formula I.

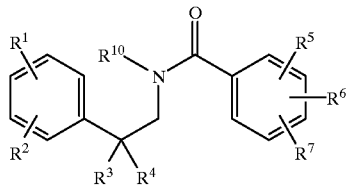

I

The compounds of this invention are useful in the treatment of autoimmune diseases, the prevention of rejection of foreign organ transplants and related afflictions, diseases and illnesses, and cardiac arrhythmias. Also within the scope of this invention are pharmaceutical formulations comprising a compound of Formula I and a pharmaceutical carrier, as well as pharmaceutical formulations comprising a compound of Formula I, one or more immunosuppressive compounds and a pharmaceutical carrier.

DETAILED DESCRIPTION OF THE INVENTION

An embodiment of the present invention is a compound of structural Formula I:

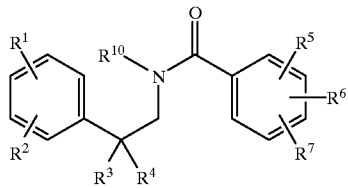

I or a pharmaceutically acceptable salt, crystal form, or hydrate, wherein:

n is: 0, 1, 2 or 3;
r is: 0 or 1;
s is: 0 or 1;
$R^1$, $R^2$, $R^5$, $R^6$ and $R^7$ are independently:
  (1) halo, wherein halo is fluoro, chloro, bromo, or iodo,
  (2) hydroxy,
  (3) $(C_1-C_6)$-alkyl,
  (4) $HO(C_1-C_6)$-alkyloxy,
  (5) $(C_1-C_4)$-perfluoroalkyl,
  (6) $(C_2-C_6)$-alkenyl,
  (7) $(C_2-C_6)$-alkynyl,
  (8) $O[(C=O)O_r]_s(C_1-C_6)$-alkyl, wherein the alkyl may be cyclic or straight-chained,
  (9) $(C_1-C_6)$-alkyl-$S(O)_n$—,
  (10) phenyl,
  (11) phenoxy,
  (12) cyano,
  (13) nitro,
  (14) $CO_2H$,
  (15) $CO(C_1-C_6)$-alkyl,
  (16) $CO_2(C_1-C_6)$-alkyl,
  (17) $CONR^8R^9$,
  (18) $NR^8R^9$,
  (20) $(C_2-C_6)$-alkenyloxy,
  (21) benzyloxy,
  (22) hydrogen,
  (23) $OCF_3$, or
  (24) $R^1$ and $R^2$ or $R^6$ and $R^7$ can an be taken together when on adjacent carbons to form a fused benzo, dihydrofuranyl, furanyl, pyrrolidyl, dihydropyrrolidyl or 1,3-dioxolan group;
$R^3$ and $R^4$ are independently:
  (1) halo, wherein halo is fluoro, chloro, bromo, or iodo,
  (2) hydroxy,
  (3) $HO(C_1-C_6)$-alkyloxy,
  (4) $(C_1-C_4)$-perfluoroalkyl,
  (5) $O(CO)CCl_3$,
  (6) $(C_1-C_6)$-alkyl-$S(O)_n$—,
  (7) phenyl-$(CH_2)_r$—$S(O)_n$—,
  (8) cyano,
  (9) nitro,
  (10) $CO_2H$,
  (11) $CO(C_1-C_6)$-alkyl,
  (12) $CO_2(C_1-C_6)$-alkyl,
  (13) $CONR^8R^9$,
  (14) $NR^8R^9$,
  (15) $O(CO)NR^8R^9$,
  (16) azido,
  (17) $NR^8(CO)NR^8R^9$,
  (18) hydrogen,
  (19) $(C_1-C_{10})$-alkyl, wherein alkyl includes cyclic as well as acyclic groups and is unsubstituted or substituted with one or two of the substituents selected from the group consisting of:
    (a) halo, wherein halo is fluoro, chloro, bromo, or iodo,
    (b) hydroxy,
    (c) oxo,
    (d) $O[(C=O)O_r]_s(C_1-C_6)$-alkyl,
    (e) $(C_1-C_6)$-alkyl-$S(O)_n$—,
    (f) aryl-$(C_1-C_6)$-alkyloxy,
    (g) cyano,
    (h) nitro,
    (i) vinyl,
    (j) $NR^8R^9$,
    (k) $O(CO)NR^8R^9$,
    (l) CHO, (m) $CO_2H$,
(n) $CO(C_1-C_6)$-alkyl,
(o) $CO_2(C_1-C_6)$-alkyl, wherein alkyl may be substituted with phenyl,
(p) $CONR^8R^9$,
(q) aryl, wherein aryl is defined as phenyl or naphthyl, unsubstituted or substituted with one, two or three of the substituents selected from the group consisting of:
  (a') halo, as defined above,
  (b') hydroxy,
  (c') $(C_1-C_6)$-alkyl,
  (d') $(C_1-C_4)$-perfluoroalkyl,
  (e') $(C_2-C_6)$-alkenyl,
  (f') $(C_2-C_6)$-alkynyl,
  (g') $(C_1-C_6)$-alkyloxy,
  (h') $(C_1-C_6)$-alkyl-$S(O)_n$—,
  (i') phenyl,
  (j') phenoxy,
  (k') cyano,
  (l') nitro,
  (m') $CO_2H$,
  (n') $CO(C_1-C_6)$-alkyl,
  (o') $CO_2(C_1-C_6)$-alkyl,
  (p') $CONR^8R^9$,
  (q') $NR^8R^9$, and
(r) heteroaryl, wherein heteroaryl is defined as an unsubstituted, monosubstituted, or disubstituted five or six membered aromatic heterocycle containing from 1 to 3 heteroatoms selected from the group consisting of O, N and S and wherein the substituents are members selected from the group consisting of:
  (a') halo, as defined above,
  (b') hydroxy,
  (c') $(C_1-C_6)$-alkyl,
  (d') $(C_1-C_4)$-perfluoroalkyl,
  (e') $(C_2-C_6)$-alkenyl,
  (f') $(C_2-C_6)$-alkynyl,
  (g') $(C_1-C_6)$-alkyloxy,
  (h') $(C_1-C_6)$-alkyl-$S(O)_n$—,
  (i') phenyl,
  (j') phenoxy,
  (k') cyano,
  (l') nitro,
  (m') $CO_2H$,
  (n') $CO(C_1-C_6)$-alkyl,
  (o') $CO_2(C_1-C_6)$-alkyl,
  (p') $CONR^8R^9$,
  (q') $NR^8R^9$, and
  (r') fused benzo or pyridyl group,
(s) heterocyclyl, wherein heterocyclyl is defined as a 3 to 7 atom cyclic, non-aromatic substituent containing from 1 to 3 heteroatoms selected from the group consisting of O, N, and S, said heterocycle being unsubstituted or substituted with one, two or three substituents selected from the group consisting of:
  (a') halo, as defined above,
  (b') hydroxy,
  (c') $(C_1-C_6)$-alkyl,
  (d') $(C_1-C_4)$-perfluoroalkyl,
  (e') $(C_2-C_6)$-alkenyl,
  (f') $(C_2-C_6)$-alkynyl,
  (g') $(C_1-C_6)$-alkyloxy,
  (h') $(C_1-C_6)$-alkyl-$S(O)_n$—,
  (i') phenyl,
  (j') phenoxy,
  (k') cyano,
  (l') nitro,
  (m') $CO_2H$,
  (n') $CO(C_1-C_6)$-alkyl,
  (o') $CO_2(C_1-C_6)$-alkyl,
  (p') $CONR^8R^9$,
  (q') $NR^8R^9$,
  (r') $NR^8CO(C_1-C_6)$-alkyl,
  (s') oxo,
  (t') fused benzo, and
  (u') fused pyridyl group;
(t) benzyl-$S(O)_n$—,
(u) $O[(C=O)O_r]_s(C_2-C_6)$-alkenyl,
(v) $O[(C=O)O_r]_s$aryl,
(w) $O[(C=O)O_r]_s$heteroaryl,
(x) $O(CH_2)_n$heteroaryl, or
(y) $O(CH_2)_n$aryl;
(20) $(C_2-C_{10})$-alkenyl, wherein alkenyl is unsubstituted or substituted with one or two of the substituents selected from the group consisting of:
  (a) halo, wherein halo is fluoro, chloro, bromo, or iodo,
  (b) hydroxy,
  (c) oxo,
  (e) $(C_1-C_6)$-alkyl-$S(O)_n$—,
  (f) phenyl-$(C_1-C_6)$-alkyloxy,
  (g) cyano,
  (h) nitro,
  (i) $NR^8R^9$,
  (j) CHO,
  (k) $CO_2H$,
  (l) $CO(C_1-C_6)$-alkyl,
  (m) $CO_2(C_1-C_6)$-alkyl,
  (n) $CONR^8R^9$,
  (o) aryl, wherein aryl is as defined above,
  (p) heteroaryl, wherein heteroaryl is as defined above,
  (q) heterocyclyl, wherein heterocyclyl is as defined above,
  (r) $O[(C=O)O_r]_s(C_1-C_6)$-alkyl, alkyl as defined above,
  (s) $O[(C=O)O_r]_s(C_2-C_6)$-alkenyl, as defined above,
  (t) $O[(C=O)O_r]_s$aryl, aryl as defined above,
  (u) $O[(C=O)O_r]_s$heteroaryl, heteroaryl as defined above,
  (v) $O(CH_2)_n$heteroaryl, heteroaryl as defined above, and
  (w) $O(CH_2)_n$aryl, aryl as defined above;
(21) $(C_2-C_{10})$-alkynyl, wherein alkynyl is unsubstituted or substituted with one or two of the substituents selected from the group consisting of:
  (a) halo, wherein halo is fluoro, chloro, bromo, or iodo,
  (b) hydroxy,
  (c) oxo,
  (d) $(C_1-C_6)$-alkyloxy,
  (e) $(C_1-C_6)$-$S(O)_n$—,
  (f) phenyl-$(C_1-C_6)$-alkyloxy,
  (g) cyano,
  (h) nitro,
  (i) vinyl,
  (j) $NR^8R^9$,
  (k) $NR^8CO(C_1-C_6)$-alkyl,
  (l) CHO,
  (m) $CO_2H$,
  (n) $CO(C_1-C_6)$-alkyl, (o) $CO_2C(C_1–C_6)$-alkyl,
(p) $CONR^8R^9$,
(q) aryl, wherein aryl is as defined above,
(r) heteroaryl, wherein heteroaryl is as defined above,
(s) heterocyclyl, wherein heterocyclyl is as defined above,
(t) $O[(C=O)O_r]_s(C_1–C_6)$-alkyl, alkyl as defined above,
(u) $O[(C=O)O_r]_s(C_2–C_6)$-alkenyl, as defined above,
(v) $O[(C=O)O_r]_s$aryl, aryl as defined above,
(w) $O[(C=O)O_r]_s$heteroaryl, heteroaryl as defined above
(x) $O(CH_2)_n$heteroaryl, heteroaryl as defined above, and
(y) $O(CH_2)_n$aryl, aryl as defined above,
(22) $O[(C=O)O_r]_s(C_1–C_6)$-alkyl, alkyl as defined above,
(23) $O[(C=O)O_r]_s(C_2–C_6)$-alkenyl, as defined above,
(24) $O[(C=O)O_r]_s$aryl, aryl as defined above,
(25) $O[(C=O)O_r]_s$heteroaryl, heteroaryl as defined above
(26) $O(CH_2)_n$heteroaryl, heteroaryl as defined above,
(27) aryl, wherein aryl is as defined above or
(28) $O(CH_2)_n$aryl, aryl as defined above;

$R^3$ can also be any of the following when $R^4$ is absent:
(29) oxo,
(30) $=CH-(C_1–C_6)$-alkyl, wherein alkyl is as defined above,
(31) $=CH-(C_2–C_6)$-alkenyl, wherein alkenyl is as defined above,
(32) $=CH$-aryl, wherein aryl is as defined above, or
(33) $=CH_2$;

$R^8$ and $R^9$ are independently selected from the group consisting of:
(1) hydrogen,
(2) $[(C=O)O_r]_s$aryl, wherein aryl is as defined above,
(3) $[(C=O)O_r]_s(C_2–C_8)$-alkenyl, wherein alkenyl is as defined above,
(4) $[(C=O)O_r]_s(C_1–C_8)$-alkyl, wherein alkyl is as defined above,
(5) $(C=O)_rS(O)_n(C_1–C_8)$-alkyl, wherein alkyl is as defined above,
(6) $(C=O)_rS(O)_n$-aryl, wherein aryl is as defined above, and
(7) heterocyclyl, wherein heterocyclyl is defined above;

$R^{10}$ is:
(1) hydrogen,
(2) $[(C=O)O_r]_s$aryl, wherein aryl is as defined above, or
(3) $[(C=O)O_r]_s(C_1–C_6)$-alkyl, wherein alkyl is as defined above.

Another embodiment of the invention is the compound of Formula 1, wherein $R^3$ and $R^4$ are independently:
(1) halo, wherein halo is fluoro, chloro, bromo, or iodo,
(2) hydroxy,
(3) $HO(C_1–C_6)$-alkyloxy,
(4) $(C_1–C_4)$-perfluoroalkyl,
(5) $O(CO)CCl_3$,
(6) $(C_1–C_6)$-alkyl-$S(O)_n$—,
(7) phenyl-$(CH_2)_r$—$S(O)_n$—,
(8) cyano,
(9) nitro,
(10) $CO_2H$,
(11) $CO(C_1–C_6)$-alkyl,
(12) $CO_2(C_1–C_6)$-alkyl,
(13) $CONR^8R^9$,
(14) $NR^8R^9$,
(15) $O(CO)NR^8R^9$,
(16) azido,
(17) $NR^8(CO)NR^8R^9$,
(18) hydrogen,
(19) $(C_1–C_6)$-alkyl, wherein alkyl includes cyclic as well as acyclic groups and is unsubstituted or substituted with one or two of the substituents selected from the group consisting of:
(a) halo, wherein halo is fluoro, chloro, bromo, or iodo,
(b) hydroxy,
(c) oxo,
(d) $O[(C=O)O_r]_s(C_1–C_6)$-alkyl,
(e) $(C_1–C_6)$-alkyl-$S(O)_n$—,
(f) aryl-$(C_1–C_6)$-alkyloxy,
(g) cyano,
(h) nitro,
(i) vinyl,
(j) $NR^8R^9$,
(k) $O(CO)NR^8R^9$,
(l) $CHO$,
(m) $CO_2H$,
(n) $CO(C_1–C_6)$-alkyl,
(o) $CO_2(C_1–C_6)$-alkyl, wherein alkyl may be substituted with phenyl,
(p) $CONR^8R^9$,
(q) aryl, wherein aryl is defined as phenyl or naphthyl, unsubstituted or substituted with one, two or three of the substituents selected from the group consisting of:
(a') halo, as defined above,
(b') hydroxy,
(c') $(C_1–C_6)$-alkyl,
(d') $(C_1–C_4)$-perfluoroalkyl,
(e') $(C_2–C_6)$-alkenyl,
(f') $(C_2–C_6)$-alkynyl,
(g') $(C_1–C_6)$-alkyloxy,
(h') $(C_1–C_6)$-alkyl-$S(O)_n$—,
(i') phenyl,
(j') phenoxy,
(k') cyano,
(l') nitro,
(m') $CO_2H$,
(n') $CO(C_1–C_6)$-alkyl,
(o') $CO_2(C_1–C_6)$-alkyl,
(p') $CONR^8R^9$,
(q') $NR^8R^9$, and
(r) heteroaryl, wherein heteroaryl is defined as an unsubstituted, monosubstituted, or disubstituted five or six membered aromatic heterocycle containing from 1 to 3 heteroatoms selected from the group consisting of O, N and S and wherein the substituents are members selected from the group consisting of:
(a') halo, as defined above,
(b') hydroxy,
(c') $(C_1–C_6)$-alkyl,
(d') $(C_1–C_4)$-perfluoroalkyl,
(e') $(C_2–C_6)$-alkenyl,
(f') $(C_2–C_6)$-alkynyl,
(g') $(C_1–C_6)$-alkyloxy,
(h') $(C_1–C_6)$-alkyl-$S(O)_n$—,
(i') phenyl,
(j') phenoxy,
(k') cyano,
(l') nitro, (m') $CO_2H$,
(n') $CO(C_1-C_6)$-alkyl,
(o') $CO_2(C_1-C_6)$-alkyl,
(p') $CONR^8R^9$,
(q') $NR^8R^9$, and
(r') fused benzo or pyridyl group,
(s) heterocyclyl, wherein heterocyclyl is defined as a 3 to 7 atom cyclic, non-aromatic substituent containing from 1 to 3 heteroatoms selected from the group consisting of O, N, and S, said heterocycle being unsubstituted or substituted with one, two or three substituents selected from the group consisting of:
(a') halo, as defined above,
(b') hydroxy,
(c') $(C_1-C_6)$-alkyl,
(d') $(C_1-C_4)$-perfluoroalkyl,
(e') $(C_2-C_6)$-alkenyl,
(f') $(C_2-C_6)$-alkynyl,
(g') $(C_1-C_6)$-alkyloxy,
(h') $(C_1-C_6)$-alkyl-$S(O)_n$—,
(i') phenyl,
(j') phenoxy,
(k') cyano,
(l') nitro,
(m') $CO_2H$,
(n') $CO(C_1-C_6)$-alkyl,
(o') $CO_2(C_1-C_6)$-alkyl,
(p') $CONR^8R^9$,
(q') $NR^8R^9$,
(r') $NR^8CO(C_1-C_6)$-alkyl,
(s') oxo,
(t') fused benzo, and
(u') fused pyridyl group;
(t) benzyl-$S(O)_n$—,
(u) $O[(C=O)O_r]_s(C_2-C_6)$-alkenyl,
(v) $O[(C=O)O_r]_s$aryl,
(w) $O[(C=O)O_r]_s$heteroaryl,
(x) $O(CH_2)_n$heteroaryl, or
(y) $O(CH_2)_n$aryl;
(20) $(C_2-C_6)$-alkenyl, wherein alkenyl is unsubstituted or substituted with one or two of the substituents selected from the group consisting of:
(a) halo, wherein halo is fluoro, chloro, bromo, or iodo,
(b) hydroxy,
(c) oxo,
(e) $(C_1-C_6)$-alkyl-$S(O)_n$—,
(f) phenyl-$(C_1-C_6)$-alkyloxy,
(g) cyano,
(h) nitro,
(i) $NR^8R^9$,
(j) CHO,
(k) $CO_2H$,
(l) $CO(C_1-C_6)$-alkyl,
(m) $CO_2(C_1-C_6)$-alkyl,
(n) $CONR^8R^9$,
(o) aryl, wherein aryl is as defined above,
(p) heteroaryl, wherein heteroaryl is as defined above,
(q) heterocyclyl, wherein heterocyclyl is as defined above,
(r) $O[(C=O)O_r]_s(C_1-C_6)$-alkyl, alkyl as defined above,
(s) $O[(C=O)O_r]_s(C_2-C_6)$-alkenyl, as defined above,
(t) $O[(C=O)O_r]_s$aryl, aryl as defined above,
(u) $O[(C=O)O_r]_s$heteroaryl, heteroaryl as defined above,
(v) $O(CH_2)_n$heteroaryl, heteroaryl as defined above, and
(w) $O(CH_2)_n$aryl, aryl as defined above;
(21) $(C_2-C_6)$-alkynyl, wherein alkynyl is unsubstituted or substituted with one or two of the substituents selected from the group consisting of:
(a) halo, wherein halo is fluoro, chloro, bromo, or iodo,
(b) hydroxy,
(c) oxo,
(d) $(C_1-C_6)$-alkyloxy,
(e) $(C_1-C_6)$-$S(O)_n$—,
(f) phenyl-$(C_1-C_6)$-alkyloxy,
(g) cyano,
(h) nitro,
(i) vinyl,
(j) $NR^8R^9$,
(k) $NR^8CO(C_1-C_6)$-alkyl,
(l) CHO,
(m) $CO_2H$,
(n) $CO(C_1-C_6)$-alkyl,
(o) $CO_2C(C_1-C_6)$-alkyl,
(p) $CONR^8R^9$,
(q) aryl, wherein aryl is as defined above,
(r) heteroaryl, wherein heteroaryl is as defined above,
(s) heterocyclyl, wherein heterocyclyl is as defined above,
(t) $O[(C=O)O_r]_s(C_1-C_6)$-alkyl, alkyl as defined above,
(u) $O[(C=O)O_r]_s(C_2-C_6)$-alkenyl, as defined above,
(v) $O[(C=O)O_r]_s$aryl, aryl as defined above,
(w) $O[C=O)O_r]_s$heteroaryl, heteroaryl as defined above
(x) $O(CH_2)_n$heteroaryl, heteroaryl as defined above, and
(y) $O(CH_2)_n$aryl, aryl as defined above,
(22) $O[(C=O)O_r]_s(C_1-C_6)$-alkyl, alkyl as defined above,
(23) $O[(C=O)O_r]_s(C_2-C_6)$-alkenyl, as defined above,
(24) $O[(C=O)O_r]_s$aryl, aryl as defined above,
(25) $O[(C=O)O_r]_s$heteroaryl, heteroaryl as defined above
(26) $O(CH_2)_n$heteroaryl, heteroaryl as defined above,
(27) aryl, wherein aryl is as defined above or
(28) $O(CH_2)_n$aryl, aryl as defined above;
$R^3$ can also be any of the following when $R^4$ is absent:
(29) oxo,
(30) $=CH-(C_1-C_6)$-alkyl, wherein alkyl is as defined above,
(31) $=CH-(C_2-C_6)$-alkenyl, wherein alkenyl is as defined above,
(32) $=CH$-aryl, wherein aryl is as defined above, or
(33) $=CH_2$.
A preferred embodiment is the compound of Formula I, wherein $R^1$, $R^2$, $R^5$, $R^6$ and $R^7$ are independently:
(1) halo, wherein halo is fluoro, chloro, bromo, or iodo,
(2) hydroxy,
(3) $(C_1-C_6)$-alkyl,
(4) $HO(C_1-C_6)$-alkyloxy,
(5) $(C_1-C_4)$-perfluoroalkyl,
(6) $(C_2-C_6)$-alkenyl,
(7) $O[(C=O)O_r]_s(C_1-C_6)$-alkyl, wherein the alkyl may be cyclic or straight-chained,
(8) phenyl,
(9) $CO(C_1-C_6)$-alkyl,
(10) $CO_2(C_1-C_6)$-alkyl,

(11) CONR$^8$R$^9$,
(12) NR$^8$R$^9$,
(13) (C$_2$–C$_6$)-alkenyloxy,
(14) benzyloxy,
(15) hydrogen,
(16) OCF$_3$,
(17) R$^1$ and R$^2$ or R$^6$ and R$^7$ can an be taken together when on adjacent carbons to form a fused benzo, dihydrofuranyl, furanyl, pyrrolidyl, dihydropyrrolidyl or 1,3-dioxolan group;

R$^3$ and R$^4$ are independently:
(1) halo, wherein halo is fluoro, chloro, bromo, or iodo,
(2) hydroxy,
(3) HO(C$_1$–C$_6$)-alkyloxy,
(4) (C$_1$–C$_4$)-perfluoroalkyl,
(5) O(CO)CCl$_3$,
(6) (C$_1$–C$_6$)-alkyl-S(O)$_n$—,
(7) phenyl-(CH$_2$)$_r$S(O)$_n$—,
(8) cyano,
(9) nitro,
(10) CO$_2$H,
(11) CO(C$_1$–C$_6$)-alkyl,
(12) CO$_2$(C$_1$–C$_6$)-alkyl,
(13) CONR$^8$R$^9$,
(14) NR$^8$R$^9$,
(15) O(CO)NR$^8$R$^9$,
(16) azido,
(17) NR$^8$(CO)NR$^8$R$^9$,
(18) hydrogen,
(19) (C$_1$–C$_6$)-alkyl, wherein alkyl includes cyclic as well as acyclic groups and is unsubstituted or substituted with one or two of the substituents selected from the group consisting of:
  (a) halo, wherein halo is fluoro, chloro, bromo, or iodo,
  (b) hydroxy,
  (c) oxo,
  (d) O[(C=O)O$_r$]$_s$(C$_1$–C$_6$)-alkyl,
  (e) aryl-(C$_1$–C$_6$)-alkyloxy,
  (f) NR$^8$R$^9$,
  (g) O(CO)NR$^8$R$^9$,
  (h) CHO,
  (i) CO$_2$H,
  (j) CO(C$_1$–C$_6$)-alkyl,
  (k) CO$_2$(C$_1$–C$_6$)-alkyl, wherein alkyl may be substituted with phenyl,
  (l) CO$_2$(C$_1$–C$_6$)-alkenyl,
  (m) CONR$^8$R$^9$,
  (n) aryl, wherein aryl is defined as phenyl or naphthyl, unsubstituted or substituted with a substituent selected from the group consisting of:
    (a') halo, as defined above,
    (b') hydroxy,
    (c') (C$_1$–C$_6$)-alkyl,
    (d') (C$_1$–C$_6$)-alkyloxy,
    (e') (C$_1$–C$_6$)-alkyl-S(O)$_n$—,
    (f') phenyl,
    (g') phenoxy,
    (h') cyano,
    (i') CO$_2$H,
    (j') CO(C$_1$–C$_6$)-alkyl,
    (k') CO$_2$(C$_1$–C$_6$)-alkyl,
    (l') CONR$^8$R$^9$,
    (m') NR$^8$R$^9$, and
  (o) benzyl-S(O)$_n$—,
  (p) O[(C=O)O$_r$]$_s$(C$_2$–C$_6$)-alkenyl,
  (q) O[(C=O)O$_r$]$_s$aryl,
  (r) O[(C=O)O$_r$]$_s$heteroaryl,
  (s) O(CH$_2$)$_n$heteroaryl, or
  (t) O(CH$_2$)$_n$aryl;
(20) (C$_2$–C$_6$)-alkenyl, wherein alkenyl is unsubstituted or substituted with a substituent selected from the group consisting of:
  (a) halo, wherein halo is fluoro, chloro, bromo, or iodo,
  (b) hydroxy,
  (c) oxo,
  (d) phenyl-(C$_1$–C$_6$)-alkyloxy,
  (e) NR$^8$R$^9$,
  (f) CHO,
  (g) CO$_2$H,
  (h) CO(C$_1$–C$_6$)-alkyl,
  (i) CO$_2$(C$_1$–C$_6$)-alkyl,
  (j) CONR$^8$R$^9$,
  (k) aryl, wherein aryl is as defined above,
  (l) O[(C=O)O$_r$]$_s$(C$_1$–C$_6$)-alkyl, alkyl as defined above,
  (m) O[(C=O)O$_r$]$_s$aryl, aryl as defined above,
  (n) O[(C=O)O$_r$]$_s$heteroaryl, heteroaryl as defined above,
  (o) O(CH$_2$)$_n$heteroaryl, heteroaryl as defined above, and
  (p) O(CH$_2$)$_n$aryl, aryl as defined above;
(21) O[(C=O)O$_r$]$_s$(C$_1$–C$_6$)-alkyl, alkyl as defined above,
(22) O[(C=O)O$_r$]$_s$(C$_2$–C$_6$)-alkenyl, as defined above,
(23) O[(C=O)O$_r$]$_s$aryl, aryl as defined above,
(24) O[(C=O)O$_r$]$_s$heteroaryl, heteroaryl as defined above
(25) O(CH$_2$)$_n$heteroaryl, heteroaryl as defined above,
(26) aryl, wherein aryl is as defined above or
(27) O(CH$_2$)$_n$aryl, aryl as defined above;

R$^3$ can also be any of the following when R$^4$ is absent:
(28) oxo,
(29) =CH-(C$_1$–C$_6$)-alkyl, wherein alkyl is as defined above,
(30) =CH-(C$_2$–C$_6$)-alkenyl, wherein alkenyl is as defined above,
(31) =CH-aryl, wherein aryl is as defined above, or
(32) =CH$_2$;

R$^8$ and R$^9$ are independently selected from the group consisting of:
(1) hydrogen,
(2) [(C=O)O$_r$]$_s$aryl, wherein aryl is as defined above,
(3) [(C=O)O$_r$]$_s$(C$_2$–C$_8$)-alkenyl, wherein alkenyl is as defined above, and
(4) [(C=O)O$_r$]$_s$(C$_1$–C$_8$)-alkyl, wherein alkyl is as defined above, and R$^{10}$ is:
(1) hydrogen, or
(2) [(C=O)O$_r$]$_s$(C$_1$–C6)-alkyl, wherein alkyl is as defined above.

Another preferred emodiment is the compound of Formula I, wherein R$^1$, R$^2$, R$^5$, R$^6$ and R$^7$ are independently:
(1) halo, wherein halo is fluoro, chloro, bromo, or iodo,
(2) hydroxy,
(3) (C$_1$–C$_3$)-alkyl,
(4) (C$_2$–C$_3$)-alkenyl,
(5) O(C$_1$–C$_4$)-alkyl, wherein the alkyl may be cyclic or straight-chained,
(6) O(CO)CH$_3$,
(7) CO(C$_1$–C$_3$)-alkyl,
(8) CO$_2$(C$_1$–C$_3$)-alkyl, (9) hydrogen,
(10) $R^1$ and $R^2$ or $R^6$ and $R^7$ can an be taken together when on adjacent carbons to form a fused benzo, dihydrofuranyl, furanyl, pyrrolidyl, dihydropyrrolidyl or 1,3-dioxolan group;

$R^3$ and $R^4$ are independently:
(1) hydrogen,
(2) $(C_1-C_6)$-alkyl, wherein alkyl includes cyclic as well as acyclic groups and is unsubstituted or substituted with one or two of the substituents selected from the group consisting of:
  (a) halo, wherein halo is fluoro, chloro, bromo, or iodo,
  (b) hydroxy,
  (c) oxo,
  (d) $O[(C=O)O_r]_s(C_1-C_6)$-alkyl, wherein r and s are independently 0 or 1,
  (e) $CO_2(C_2-C_3)$-alkenyl,
  (f) $O[(C=O)O_r]_s(C_1-C_6)$-alkenyl, wherein r and s are independently 0 or 1,
  (g) $NR^8R^9$,
  (h) $O(CO)NR^8R^9$,
  (i) CHO,
  (j) $CO_2H$,
  (k) $CO(C_1-C_6)$-alkyl,
  (l) $CO_2(C_1-C_6)$-alkyl, wherein alkyl may be substituted with phenyl,
  (m) $CONR^8R^9$,
  (n) aryl, wherein aryl is defined as phenyl, unsubstituted or substituted with a substituent selected from the group consisting of:
    (a') halo, as defined above,
    (b') hydroxy,
    (c') $(C_1-C_6)$-alkyl, and
    (d') $(C_1-C_6)$-alkyloxy, and
  (o) $O[(C=O)O_r]_s(C_2-C_6)$-alkenyl, wherein r and s are independently 0 or 1,
(3) $(C_2-C_6)$-alkenyl,
(4) aryl, wherein aryl is as defined above or
(5) $O(CH_2)_n$aryl, wherein aryl is as defined above;

$R^3$ can also be any of the following when $R^4$ is absent:
(6) $=CH-(C_1-C_6)$-alkyl, wherein alkyl is as defined above,
(7) $=CH-(C_2-C_6)$-alkenyl, wherein alkenyl is as defined above, $R^8$ and $R^9$ are independently selected from the group consisting of:
(1) hydrogen,
(2) $[(C=O)O_r]_s$aryl, wherein aryl is as defined above and r and s are independently 0 or 1,
(3) $(C_2-C_8)$-alkenyl, wherein alkenyl is as defined above, and
(4) $(C_1-C_6)$-alkyl, wherein alkyl is as defined above, and $R^{10}$ is:
(1) hydrogen, or
(2) $(C=O)(C_1-C_3)$-alkyl, wherein alkyl is as defined above.

A most preffered emodiment is a compound which is selected from the group consisiting of: 1-(2-methoxyphenyl)-1-oxo-2-aza-(S)-4-i-butyl-4-phenylbutane, 1-(2-methoxyphenyl)-1-oxo-2-aza-4-(S)-((3-allyloxycarbonyloxy)propyl))-4-phenylbutane, 1-(2-methoxyphenyl)-1-oxo-2-aza-4,4-diethyl-4-phenylbutane, 1-(2,3-dihydrobenzofuran-7-yl)-1-oxo-2-aza-4,4-diethyl-4-(phenyl)-butane, and 1-(2-methoxyphenyl)-1-oxo-2-aza-4-(S)-(3-hydroxypropyl)-4-phenylbutane, or a pharmaceutically acceptable salt thereof.

Also encompassed by the present invention is a method of treating a condition in a mammal, the treatment of which is effected or facilitated by Kv1.3 inhibition, which comprises administering the compound of claim 1 in an amount that is effective at inhibiting $K_v1.3$. Preferred conditions include: resistance by transplantation of organs or tissue, graft-versus-host diseases brought about by medulla ossium transplantation, rheumatoid arthritis, systemic lupus erythematosus, Hashimoto's thyroiditis, multiple sclerosis, myasthenia gravis, type I diabetes uveitis, juvenile-onset or recent-onset diabetes mellitus, posterior uveitis, allergic encephalomyelitis, glomerulonephritis, infectious diseases caused by pathogenic microorganisms, inflammatory and hyperproliferative skin diseases, psoriasis, atopical dermatitis, contact dermatitis, eczematous dermatitises, seborrhoeis dermatitis, Lichen planus, Pemphigus, bullous pemphigoid, Epidermolysis bullosa, urticaria, angioedemas, vasculitides, erythemas, cutaneous eosinophilias, Lupus erythematosus, acne, Alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, Scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns and leukotriene $B_4$-mediated diseases, Coeliac diseases, proctitis, eosinophilic gastroenteritis, mastocytosis, Crohn's disease, ulcerative colitis, migraine, rhinitis, eczema, interstitial nephritis, Good-pasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy; Pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis, pigentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenis, metastasis of carcinoma and hypobaropathy, disease caused by histamine or leukotriene-$C_4$ release, Behcet's disease, autoimmune hepatitis, primary biliary cirrhosis sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augention of chemotherapeutic effect, cytomegalovirus infection, HCMV infection, AIDS, cancer, senile dementia, trauma, and chronic bacterial infection. A most preferred condition is an autoimmune disease.

A further embodiment of the invention is a method of preventing or treating resistance to transplantation or transplantation rejection of organs or tissues in a patient in need thereof, which comprises administering a therapeutically effective amount of a compound of Formula I. Also encompassed within the invention is a method of suppressing the immune system in a subject in need thereof, which comprises administering to the subject an immune suppressing amount of a compound of Formula 1.

Another embodiment is a pharmaceutical formulation comprising a pharmaceutically acceptable carrier and the compound of Formula 1 or a pharmaceutically acceptable crystal form or hydrate thereof. A subembodiment of the invention is a pharmaceutical formulation of the compound of Formula I, comprising, in addition, a second immunosuppressive agent. Preferred immunosuppressive agents include, but are not limited to, azathioprine, brequinar sodium, deoxyspergualin, mizaribine, mycophenolic acid morpholino ester, cyclosporin, FK-506 and rapamycin.

Yet another embodiment is a method of treating a condition in a mammal, the treatment of which is effected or facilitated by $K_v1.5$ inhibition, which comprises administering a compound of Formula 1 in an amount that is effective at inhibiting $K_v1.5$. A preferred emodiment is a method of preventing or treating cardiac arrhythmias in a mammal, which comprises administering a therapeutically effective amount of a compound of Formula I.

The compounds of the present invention have asymmetric centers and this invention includes all of the optical isomers and mixtures thereof. Unless specifically mentioned otherwise, reference to one isomer applies to both isomers.

In addition compounds with carbon-carbon double bonds may occur in Z— and E— forms with all isomeric forms of the compounds being included in the present invention.

As used herein, the term "alkyl", unless otherwise indicated, includes those alkyl groups of a designated number of carbon atoms of either a straight, branched, or cyclic configuration (carbocycles). Examples of "alkyl" include methyl, ethyl, propyl, isopropyl, butyl, sec-and tert-butyl, pentyl, hexyl, heptyl, cyclopropyl, cyclobutyl, cyclopentyl, cyclohexyl, cycloheptyl, norbornyl, and the like. "Alkoxy" represents an alkyl group of indicated number of carbon atoms attached through an oxygen bridge, such as methoxy, ethoxy, propoxy, butoxy and pentoxy. The following illustrate the foregoing definitions: "$(C_1-C_3)$-alkyl" may be methyl, ethyl, propyl, isopropyl, or cyclopropyl. Similarly, "O-$(C_1-C_3)$-alkyl" may be methoxy, ethoxy, n-propoxy, i-propoxy, or cyclopropoxy. In some cases, a $C_0$ designation is used, as in "-$(C_0-C_2)$-alkyl-phenyl." In such a case, the substituent is intended to be any of the following: phenyl, benzyl, 1-phenylethyl, or 2-phenylethyl. In certain definitions, the alkyl may be substituted with one or more substituents. For example a definition which reads "$(C_1-C_2)$-alkyl, substituted with one or two substitutents selected from oxo, hydroxy, and halo" is intended to include $C(O)CH_3$, $CH_2BrCH_3$, $CO_2H$, $C(OH)CH_3$, $CH_2CH_2(OH)$, $CH_2CO_2H$, $CHBrCH_2Cl$, CHO, and so on.

"Alkenyl" is intended to include hydrocarbon chains of a specified number of carbon atoms of either a straight- or branched-configuration and at least one unsaturation, which may occur at any point along the chain, such as ethenyl, propenyl, butenyl, pentenyl, dimethyl pentenyl, and the like, and includes E and Z forms, where applicable. "Halogen" and "halo", as used herein, mean fluoro, chloro, bromo and iodo.

The term "aryl," unless specifically defined otherwise, defined as phenyl or naphthyl, unsubstituted or substituted with one, two or three of the substituents selected from the group consisting of halo, hydroxy, alkyl, perfluoroalkyl, alkenyl, alkynyl, alkyloxy, alkyl-$S(O)_n$—, phenyl, phenoxy, cyano, nitro, $CO_2H$, CO-alkyl, $CO_2$-alkyl, $CONR^8R^9$, and $NR^8R^9$.

The term "heteroaryl" as utilized herein, unless specifically defined otherwise, is intended to include the following: an unsubstituted, monosubstituted, or disubstituted five or six membered aromatic heterocycle containing from 1 to 3 heteroatoms selected from the group consisting of O, N and S and wherein the substituent is halo, hydroxy, alkyl, perfluoroalkyl, alkenyl, alkynyl, alkyloxy, -alkyl-$S(O)_n$—, phenyl, phenoxy, cyano, nitro, $CO_2H$, CO-alkyl, $CO_2$-alkyl, $CONR^8R^9$, $NR^8R^9$, or a fused benzo or pyridyl group. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, pyrazinyl, pyridazinyl, pyridinyl, pyrimidinyl, and pyrrolyl which are substituted or unsubstituted as defined above.

In the compounds of Formula I, the heteroaryl or aryl groups may be optionally substituted with the substituents listed above at any available carbon atom or nitrogen atom (if present), but compounds bearing certain substitutents, directly substituted to a nitrogen may be relatively unstable and are not preferred. The heteroaryl may also be fused to a second 5-, 6-, or 7-membered ring containing one or two oxygens such as: dioxolanyl, dihydrofuranyl, dihydropyranyl, and dioxanyl. Disubstituted aryl groups may be ortho, para or meta and all three are intended unless specifically defined otherwise.

"Heterocyclyl" is defined as a 3 to 7 atom cyclic, non-aromatic substituent containing from 1 to 3 heteroatoms selected from the group consisting of O, N, and S, which is unsubstituted or substituted with one, two or three substituents selected from the group consisting of halo, hydroxy, alkyl, perfluoroalkyl, alkenyl, alkynyl, alkyloxy, alkyl-$S(O)_n$—, phenyl, phenoxy, cyano, nitro, $CO_2H$, COalkyl, $CO_2$-alkyl, $CONR^8R^9$, $NR^8R^9$, $NR^8CO$-alkyl, oxo, fused benzo, and fused pyridyl group.

Pharmaceutically acceptable salts include both the metallic (inorganic) salts and organic salts; a list of which is given in *Remington's Pharmaceutical Sciences*, 17th Edition, pg. 1418 (1985). It is well known to one skilled in the art that an appropriate salt form is chosen based on physical and chemical stability, flowability, hydroscopicity and solubility. As will be understood by those skilled in the art, pharmaceutically acceptable salts include, but are not limited to salts of inorganic acids such as hydrochloride, sulfate, phosphate, diphosphate, hydrobromide, and nitrate or salts of an organic acid such as malate, maleate, fumarate, tartrate, succinate, citrate, acetate, lactate, methanesulfonate, p-toluenesulfonate or palmoate, salicylate and stearate. Similarly pharmaceutically acceptable cations include, but are not limited to sodium, potassium, calcium, aluminum, lithium and ammonium (especially ammonium salts with secondary amines). Preferred salts of this invention for the reasons cited above include potassium, sodium, calcium and ammonium salts. Also included within the scope of this invention are crystal forms, hydrates and solvates of the compounds of Formula I.

Methods for preparing the compounds of this invention are illustrated in the following schemes and examples. Other synthetic routes would be readily apparent to those skilled in the art.

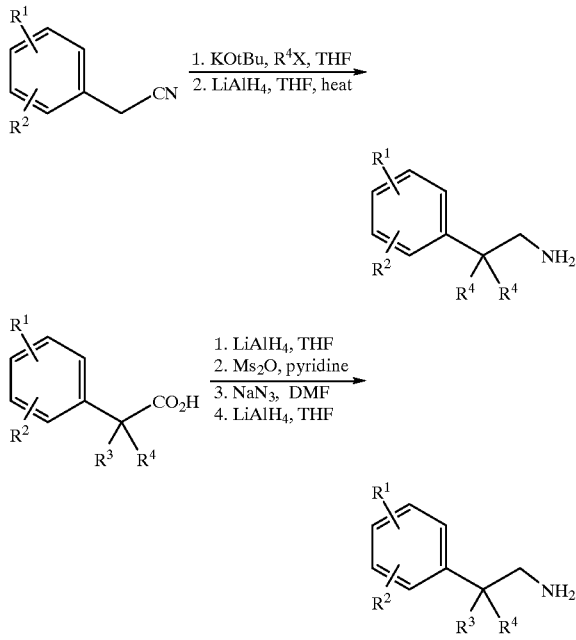

Many methods are available to prepare the amine precursors that serve as starting materials for the compounds of this invention. The substituted or unsubstituted phenylacetonitrile substrates shown in Scheme A are commercially available or can be prepared by procedures well known in the art. As shown in Scheme A, the phenylacetonitrile precursors are deprotonated with bases such as potassium t-butoxide (KOtBu) or sodium hydride (NaH) in an aprotic solvent such as THF and alkylated with alkyl halides. This leads primarily to bis-alkylation. The resulting arylacetonitriles are then reduced to amines with suitable reducing agents such as excess lithium aluminum hydride (LiAlH$_4$) in an aprotic solvent such as THF, preferably at elevated temperatures.

Amine intermediates are also prepared from substituted phenylacetic acid precursors, many which are commercially available in chiral or racemic form. The acid substrate is reduced with LiAH$_4$ in THF to give the alcohol. The hydroxy group is derivatized as the methanesulfonate with methanesulfonyl chloride in pyridine or in THF or dichloromethane with triethylamine or pyridine. This intermediate is then reacted with sodium azide in a polar aprotic solvent such as dimethylformamide. Alternatively, lithium azide in THF can be used. Finally, the azide is reduced to the corresponding amino group by hydrogenation using a palladium catalyst. This and other procedures are described in March, J.; Advanced Organic Chemistry, 4th ed., John Wiley & Sons, New York, pp. 428 and 1219 (1992).

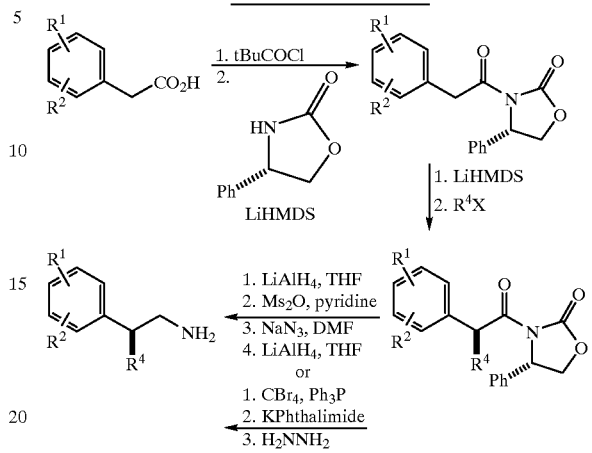

In reaction Scheme B, R$^4$ groups are appended by asymmetric alkylation of phenylacetyloxazolidinone imides as reviewed by Evans, Asymmetric Synthesis, vol. 3, Academic Press Inc., New York, p 2–101 (1984). Thus, alkylation using (R)-(−)-4-phenyl-2-oxazolidinone provides the R$^4$ substituent in the (S)-configuration. The (S)-(−)-4-phenyl-2-oxazolidinone gives R$^4$ in the (R)-configuration. The oxazolidinone group is removed with LiAlH$_4$ to give the hydroxy intermediate which is then converted as described in Reaction Scheme A.

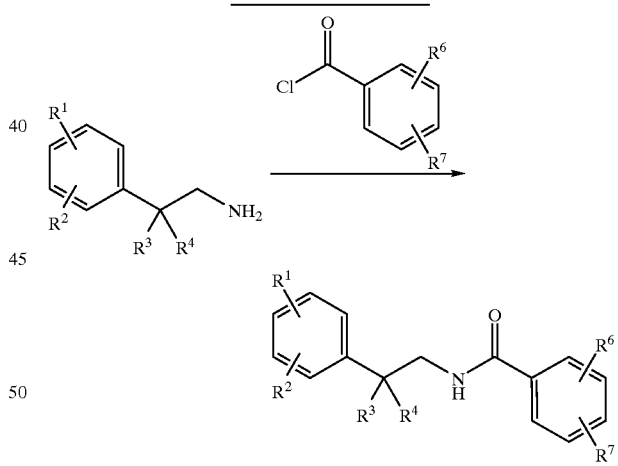

As shown in Scheme C, the amine intermediates are then acylated with acid chlorides in aprotic solvents such as THF and CH$_2$Cl$_2$ with a base such as triethylamine to give the corresponding benzamides. The acid chlorides, when not purchased, are prepared by stirring the carboxylic acids in reagents such as oxalyl chloride or thionyl chloride. Alternatively, amides can be prepared by reaction of benzoic acids with the amine using the standard coupling conditions as described in March, J.; Advanced Organic Chemistry, 4th ed., John Wiley & Sons, New York, pp. 417–424 (1992). One such coupling reagent is dicyclohexyl carbodiimide as reviewed by Bodanski, The Practice of Peptide Synthesis, Springer, New York, (1984).

REACTION SCHEME D

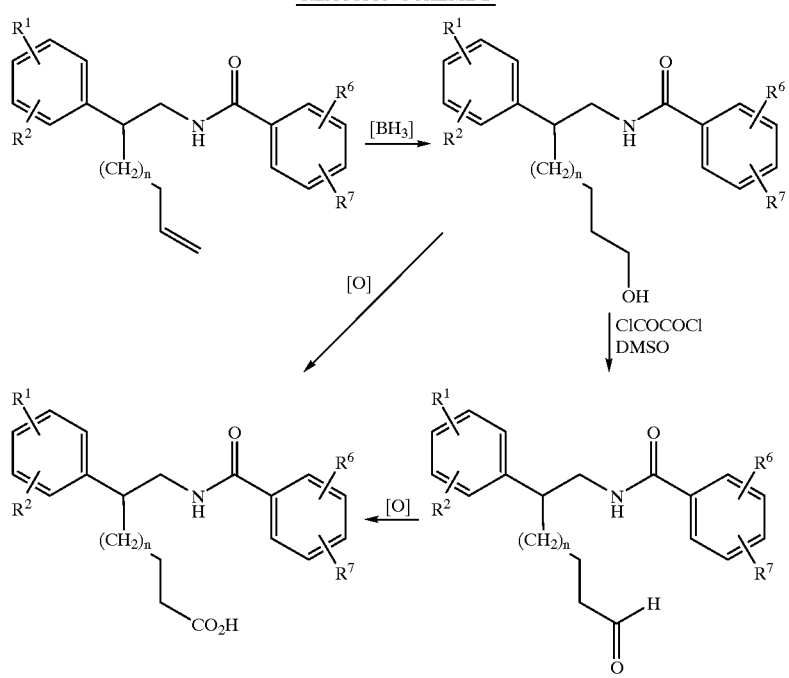

As shown in Scheme D, in an embodiment of this invention, derivatives containing olefins are hydroborated to give primary alcohols as reviewed in March, J.; Advanced Organic Chemistry, 4th ed., John Wiley & Sons, New York, pp. 783–789 (1992). For optimal regioselectivity, a substituted borane reagent such as 9-borabicyclo(3.3.1)nonane (9-BBN) is preferred. Cleavage of the borane intermediate with hydrogen peroxide provides the alcohol.

The primary alcohol is then converted to an aldehyde by a Swern oxidation procedure with oxalyl chloride in DMSO as reviewed by Mancuso and Swern, Synthesis, 165–185 (1981).

The primary alcohol or aldehyde is converted to a carboxylic acid by a variety of oxidation procedures as referenced by Larock, Comprehensive Organic Transformation, VCH, New York, pp 93–97 (1989).

REACTION SCHEME E

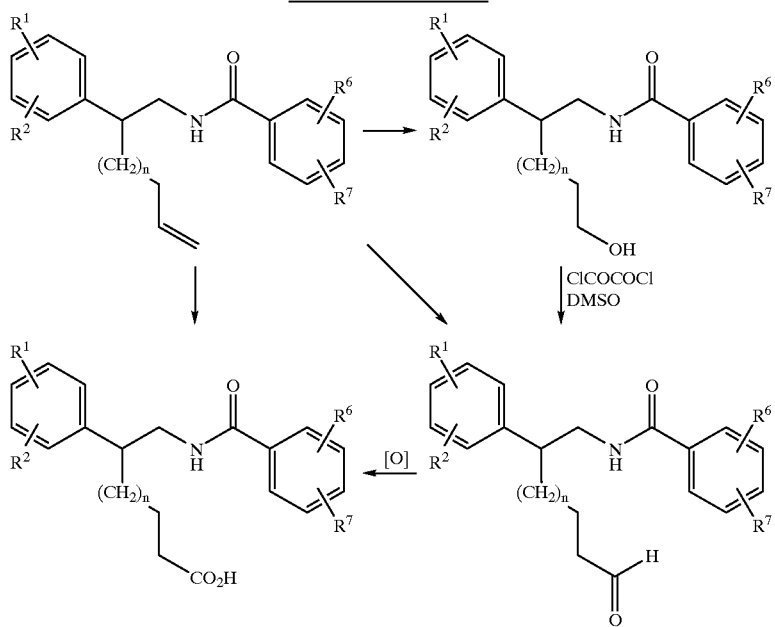

In Reaction Scheme E, the olefin group can be oxidatively cleaved with ozone. The ozonide can be reduced with sodium borohydride to give the corresponding alcohol, or it can be decomposed to the corresponding aldehyde as described in March, J.; Advanced Organic Chemistry, 4th ed., John Wiley & Sons, New York, pp. 1177–1181 (1992). Alternatively, the aldehyde is prepared by cleavage with catalytic osmium tetroxide and periodate. The aldehyde is then converted to the corresponding acid as described in Reaction Scheme D. The olefin can be cleaved to the carboxylic acid directly with ruthenium tetroxide and periodate.

derivatives. Carbamate derivatives are also prepared with commercially available carbamoyl chlorides or isocyanates.

Ether derivatives can also be prepared. A particulary useful procedure involves reacting an alcohol with trifluoromethane sulfonic anhydride (Tf$_2$O, triflic anhydride) in dichloromethane at reduced temperature, preferably −78° C. to obtain the preformed triflate. To this solution is added the alcohol, the reaction mixture is warmed to room temperature and stirring is continued until reaction is complete. Ethers may also be prepared by heating a mixture of alcohol, the appropriate alkylhalide and an excess of silver oxide (Ag$_2$O) in an aprotic invert solvent such as THF.

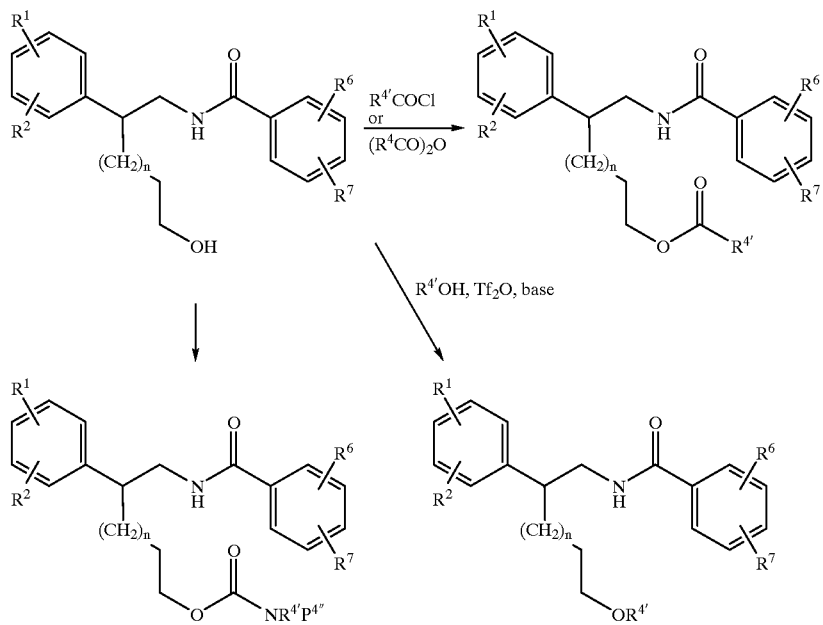

As depicted in Reaction Scheme F, esters can be prepared by reaction of an acid chloride with the hydroxy group in a basic solvent such as pyridine. It should be understood that R$^{4'}$ is used to represent a portion of the R$^4$ definition. The acid chlorides, when not purchased, are prepared by stirring the carboxylic acids in reagents such as oxalyl chloride or thionyl chloride. Esters may also be prepared by reaction of the acid chloride and the hydroxy group with silver cyanide (AgCN) in an aprotic solvent such as HMPA. C1 sulfonate derivatives are prepared in a similar manner by reaction with sulfonyl chlorides.

Carbonate and carbamate derivatives are prepared by first reacting the alcohol derivative with carbonyldiimidazole (CDI) to obtain the imidazolecarbonyl intermediate which is then reacted with an alcohol (R$^{4'}$OH) or amine (R$^{4'}$R$^{4''}$NH) to give the corresponding carbonate or carbamate derivatives. In an alternate approach, reaction of the hydroxy group with 4-nitrochloroformate provides the 4-nitrophenylcarbonate which then can be reacted with amines to give carbamates or with alcohols to give carbonate

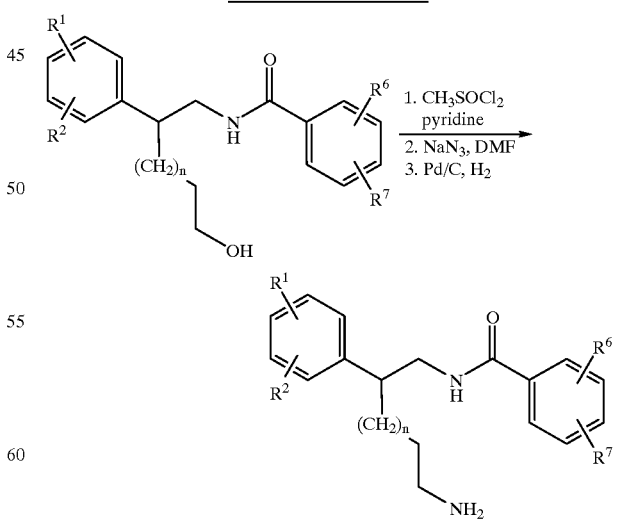

In Reaction Scheme G, the hydroxy group is converted to the corresponding amino group by well-known procedures. The hydroxy group is first derivatized as the methanesulfonate with methanesulfonyl chloride in pyridine or in THF or dichloromethane with triethylamine or pyridine. This intermediate is then reacted with sodium azide in a polar aprotic solvent such as dimethylformamide. Alternatively, lithium azide in THF can be used. The azide displacement occurs with inversion, so that the beta hydroxy group gives the alpha azide derivative and vice versa. Finally, the azide is reduced to the corresponding amino group by hydrogenation using a palladium catalyst. This and other procedures are described in March, J.; Advanced Organic Chemistry, 4th ed., John Wiley & Sons, New York, pp. 428 and 1219 (1992).

4-nitrophenylcarbamate which then can be reacted with alcohols. Carbamate derivatives are also prepared with chloroformates. For instance, reaction with ethylchloroformate will give the ethylcarbamate derivative.

The amino group can be alkylated by reductive amination procedures. For instance, the amino group is reacted with an aldehyde or ketone in the presence of sodium cyanoborohydride or sodium triacetoxyborohydride. This transformation may also be accomplished with hydrogen and a catalyst.

UTILITY

The present invention is related to compounds of Formula I, including but not limited to those specified in the

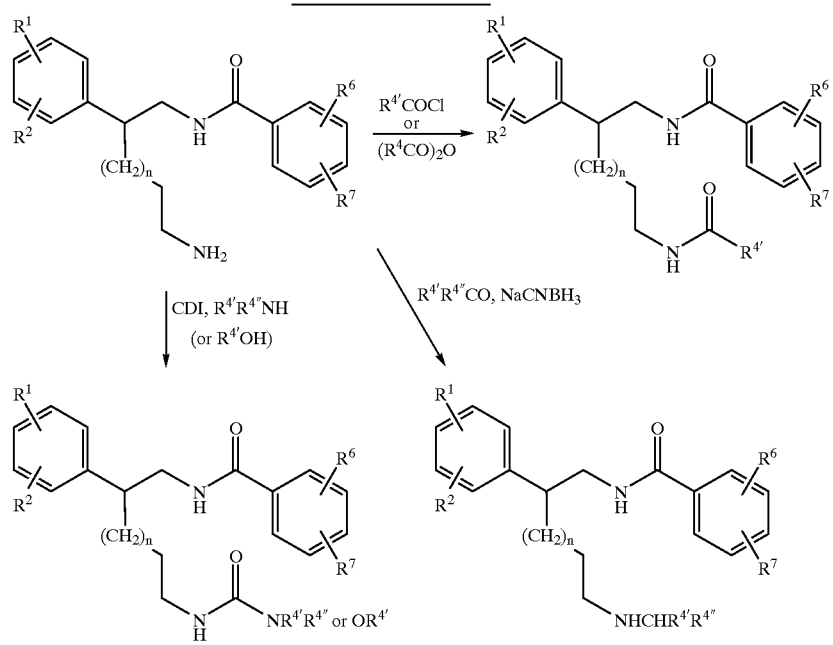

REACTION SCHEME H

As depicted in Reaction Scheme H, amides are prepared by reaction of an acid chloride with the amino group in a basic solvent such as pyridine. The acid chlorides, when not purchased, are prepared by stirring the carboxylic acids in reagents such as oxalyl chloride or thionyl chloride. Amides may also be prepared from carboxylic acids by using coupling reagents such as dicyclohexyl carbodiimide as reviewed by Bodanski, The Practive of Peptide Synthesis, Springer, New York, (1984). C1 sulfonamide derivatives are prepared in a similar manner by reaction with sulfonyl chlorides.

Urea derivatives are prepared by first reacting the C4 amino derivative with carbonyldiimidazole (CDI) to obtain the imidazolecarbonyl intermediate which is then reacted with an amine ($R^{4'}R^{4''}NH$) to give the corresponding urea derivatives. In an alternate approach, reaction of the amino group with 4-nitrochloroformate provides the 4-nitrophenyl carbamate which then can be reacted with amines to give urea derivatives. Urea derivatives are also prepared with commercially available carbamoyl chlorides or isocyanates.

Carbamate derivatives are prepared in a similar manner. Reacting the C4 amino derivative with carbonyldiimidazole (CDI) gives the imidazolecarbonyl intermediate which is then reacted with an alcohol to give the corresponding carbamate derivatives. In an alternate approach, reaction of the amino group with 4-nitrochloroformate provides the examples, which are useful in a mammalian subject for the treatment and prevention of immunemediated diseases such as the resistance by transplantation of organs or tissue such as heart, kidney, liver, medulla ossium, skin, cornea, lung, pancreas, intestinum tenue, limb, muscle, nervous, duodenum, small-bowel, pancreatic-islet-cell, including xeno transplants, etc.; graft-versus-host diseases brought about by medulla ossium transplantation; autoimmune diseases such as rheumatoid arthritis, systemic lupus erythematosus, Hashimoto's thyroiditis, multiple sclerosis, myasthenia gravis, type I diabetes uveitis, juvenile-onset or recent-onset diabetes mellitus, posterior uveitis, allergic encephalomyelitis, glomerulonephritis, and the like; and further infectious diseases caused by pathogenic microorganisms. Further uses may include the treatment and prophylaxis of inflammatory and hyperproliferative skin diseases and cutaneous manifestations of immunologically mediated illnesses, such as psoriasis, atopical dermatitis, contact dermatitis and further eczematous dermatitises and further eczematous dermatitises, seborrhoeis dermatitis, Lichen planus, Pemphigus, bullous pemphigoid, Epidermolysis bullosa, urticaria, angioedemas, vasculitides, erythemas, cutaneous eosinophilias, Lupus erythematosus, acne and Alopecia areata; various eye diseases (autoimmune and otherwise) such as keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, Scleritis, Graves' opthalmopathy, Vogt-Koyanagi-Harada syndrome, sarcoidosis, etc.; pollen allergies, reversible obstructive airway disease, which includes condition such as asthma (for example, bronchial asthma, allergic asthma, intrinsic asthma, extrinsic asthma and dust asthma), particularly chronic or inveterate asthma (for example, late asthma and airway hyper-responsiveness), bronchitis and the like; inflammation of mucous and blood vessels such as gastric ulcers, vascular damage caused by ischemic diseases and thrombosis, ischemic bowel diseases, inflammatory bowel diseases, necrotizing enterocolitis, intestinal lesions associated with thermal burns and leukotriene $B_4$-mediated diseases; intestinal inflammations/allergies such as Coeliac diseases, proctitis, eosinophilic gastroenteritis, mastocytosis, Crohn's disease and ulcerative colitis; food-related allergic diseases which have symptomatic manifestation remote from the gastrointestinal tract (e.g. migraine, rhinitis and eczema); renal diseases such as interstitial nephritis, Good-pasture's syndrome, hemolytic-uremic syndrome and diabetic nephropathy; nervous diseases such as multiple myositis, Guillain-Barre syndrome, Meniere's disease, polyneuritis, multiple neuritis, mononeuritis and radiculopathy; endocrine diseases such as hyperthyroidism and Basedow's disease; hematic diseases such as pure red cell aplasia, aplastic anemia, hypoplastic anemia, idiopathic thrombocytopenic purpura, autoimmune hemolytic anemia, agranulocytosis, pernicious anemia, megaloblastic anemia and anerythroplasia; bone diseases such as osteoporosis; respiratory diseases such as sarcoidosis, fibroid lung and idiopathic interstitial pneumonia; skin disease such as dermatomyositis, leukoderma vulgaris, ichthyosis vulgaris, photoallergic sensitivity and cutaneous T cell lymphoma; circulatory diseases such as arteriosclerosis, atherosclerosis, aortitis syndrome, polyarteritis nodosa and myocardosis; collagen diseases such as scleroderma, Wegener's granuloma and Sjogren's syndrome; adiposis; eosinophilic fascitis; periodontal disease such as lesions of gingiva, periodontium, alveolar bone and substantia ossea dentis; nephrotic syndrome such as glomerulonephritis; male pattern alopecia or alopecia senilis by preventing epilation or providing hair germination and/or promoting hair generation and hair growth; muscular dystrophy; Pyoderma and Sezary's syndrome; Addison's disease; active oxygen-mediated diseases, as for example organ injury such as ischemia-reperfusion injury of organs (such as heart, liver, kidney and digestive tract) which occurs upon preservation, transplantation or ischemic disease (for example, thrombosis and cardiac infraction): intestinal diseases such as endotoxin-shock, pseudomembranous colitis and colitis caused by drug or radiation; renal diseases such as ischemic acute renal insufficiency and chronic renal insufficiency; pulmonary diseases such as toxinosis caused by lung-oxygen or drug (for example, paracort and bleomycins), lung cancer and pulmonary emphysema; ocular diseases such as cataracta, siderosis, retinitis, pigmentosa, senile macular degeneration, vitreal scarring and corneal alkali burn; dermatitis such as erythema multiforme, linear IgA ballous dermatitis and cement dermatitis; and others such as gingivitis, periodontitis, sepsis, pancreatitis, diseases caused by environmental pollution (for example, air pollution), aging, carcinogenis, metastasis of carcinoma and hypobaropathy; disease caused by histamine or leukotriene-$C_4$ release; Behcet's disease such as intestinal-, vasculo- or neuro-Behcet's disease, and also Behcet's which affects the oral cavity, skin, eye, vulva, articulation, epididymis, lung, kidney and so on. Furthermore, the compounds of the invention are useful for the treatment and prevention of hepatic disease such as immunogenic diseases (for example, chronic autoimmune liver diseases such as the group consisting of autoimmune hepatitis, primary biliary cirrhosis and sclerosing cholangitis), partial liver resection, acute liver necrosis (e.g. necrosis caused by toxin, viral hepatitis, shock, or anoxia), B-virus hepatitis, non-A/non-B hepatitis, cirrhosis (such as alcoholic cirrhosis) and hepatic failure such as fulminant hepatic failure, late-onset hepatic failure and "acute-on-chronic" liver failure (acute liver failure on chronic liver diseases), and moreover are useful for various diseases such as augmention of chemotherapeutic effect, preventing or treating activity of cytomegalovirus infection, particularly HCMV infection, and antiinflammatory activity.

The compounds of the present invention may also be used in the treatment of immunodepression or a disorder involving immunodepression, such as AIDS, cancer, senile dementia, trauma (including wound healing, surgery and shock) chronic bacterial infection, and certain central nervous system disorders.

Using the methodologies described below, representative compounds of the invention were evaluated and found to exhibit activity thereby demonstrating and confirming the utility of the compounds of the invention as $K_v1.3/Kv1.5$ inhibitors and therefore as immunosuppressants and antiarrhythmics.

ASSAYS

T CELL IL-2 ASSAY

Peripheral blood mononuclear (MNC) cells from healthy donors were separated by density centrifugation with ficoll-hypaque (LSM, Organon Teknika, Durham, N.C.), followed by rosetted with neuraminidase treated sheep red blood cells (SRBC). After another centrifugation with leucocyte separation medium (LSM), the SRBC of the rosetted T cells were then lysed with ammonium chloride lysing buffer (GIBCO, Grand Island, N.Y.). Such purified T cells were resuspended at $3 \times 10^6$/mL in RPMI 1640 culture medium (GIBCO) supplemented with 10% fetal calf serum (Sigma, St. Louis, Mo.), 100 mM glutamine, 1 mM sodium pyruvate, 0.1 mM non-essential amino acids, and 1% penn-strep (GIBCO). The cell suspension was immediately distributed into 96 well round-bottom microculture plates (Costar) at 200 $\mu$L/well. The various dilutions of test compound were then added in triplicate wells at 25 $\mu$L/well, incubated for 30 min at 37° C. Ionomycin (125 ng/mL), and PMA (1 or 5 ng/mL), were added to the appropriate wells. The culture plates were then incubated at 37° C. in a humidified atmosphere of 5% $CO_2$—95% air for 18–24 hours. The supernatants were removed, and assayed for IL-2 with an IL-2 capture ELISA, using monoclonal anti-IL-2, and biotinylated goat anti-IL-2 antibodies (unconjugated antibodies purchased from R&D System, Minneapolis, Minn.). The ELISA was developed with streptavidin conjugated peroxidase (Zymed, San Francisco, Calif.) and substrate for peroxidase (Sigma). Mean OD and units of IL-2 of the replicate wells were calculated from standard curve, created with recombinant IL-2 (Collaborative Biomedical Products, Bedford, Mass.) and the results were expressed as concentration of compound required to inhibit IL-2 production of T cells by 50%.

T CELL PROLIFERATION ASSAY

Peripheral blood mononuclear cells (MNC) from healthy donors were separated by density centrifugation with ficoll-hypaque (LSM, Organon Teknika, Durham, N.C.). After washing the MNC with complete media (RPMI 1640 medium with 5% fetal calf serum, 100 mM glutamine, 1 mM sodium pyruvate, 0.1 mM non-essential amino acid, and 1% penn-strep, obtained from GIBCO, Grand Island, N.Y.), they were then irradiated at 7500 RADS, and resuspended at 4–4.5×10$^6$ cells/mL in complete media. Another aliquot of MNC were rosetted with neuraminidase treated SRBC. After another centrifugation with LSM, the sheep red blood cells (SRBC) of these rosetted T cells were then lysed with ammonium chloride lysing buffer (GIBCO, Grand Island, N.Y.). After washing 2× with complete media, these purified T cells were also resuspended at 2–2.5×10$^6$ cells/mL in complete media. The various dilutions of the compound were added in triplicates at 50 ul/well of a 96 well flat-bottom microculture plate (Costar, Cambridge, Mass.). T cell suspension was then immediately distributed into the wells at 100 ul/well. After incubating the cells with compound for 30 min. at 37° C. in a humidified atmosphere of 5% $CO_2$—95% air, 20 $\mu\Lambda$/well of anti-CD3 (Ortho Diagnostic, NJ) at final conc. of 0.3 ng/mL was added, followed by 50 $\mu\Lambda$ of the irradiated MNC. The culture plates were then incubated at 37° C. in a humidified atmosphere of 5% $CO_2$—95% air for 72 hours. The proliferation of T lymphocytes was assessed by measurement of tritiated thymidine incorporation. During the last 18–24 hrs. of culturing, the cells were pulse-labeled with 2 $\mu$Ci/well of tritiated thymidine (NEN, Cambridge, Mass.). The cultures were harvested on glass fiber filters using a multiple sample harvester (MACH-II, Wallac, Gaithersburg, Md.). Radioactivity of filter discs corresponding to individual wells was measured by standard liquid scintillation counting methods (Betaplate Scint Counter, Wallac). Mean counts per minute of replicate wells were calculated and the results were expressed as concentration of compound required to inhibit tritiated thymidine uptake of T cells by 50%.

$K_v1.3$-RUBIDIUM EFFLUX ASSAY

CHO cells transfected with $K_v1.3$ channels at site densities of approximately 40,000 sites/cell are plated into 96 well culture plates and maintained in Iscove's Modified Dulbecco's Medium (IMDM, with L-Glutamine and HEPES, JRH Biosciences). Cells are incubated overnight with $^{86}Rb^+$ (3 $\mu$Ci/mL, Dupont-NEN) in the glutamine supplemented IMDM. After aspiration of the media, 100 $\mu$L of Low K Buffer (in mM, 6.5 KCl, 125 NaCl, 1 $CaCl_2$, 2 $MgCl_2$, 10 HEPES, pH adjusted to 7.2 with NaOH) is added to each well followed by 100 $\mu$L test samples in Low K Buffer also containing 0.2% BSA and 2 mM ouabain. Samples are tested at either 1 $\mu$g/mL for routine screening or at a variety of concentrations encompassing at least $^1/_{10}$ to 10 times the putative $IC_{50}$ of test compound to determine potency. After a fixed preincubation time, which is usually 10 min, the samples are aspirated. The $K_v1.3$ channels are opened by depolarization of the cells with High K Buffer (final concentrations, in mM, 63.25 KCl, 68.25 NaCl, 1 $CaCl_2$, 2 $MgCl_2$, 10 HEPES, pH adjusted to 7.2 with NaOH) also containing test compounds. To measure $^{86}Rb^+$ efflux through the channels, aliquots of 100 $\mu$L are taken from each well after a given time and added to plates containing 100 $\mu$L MicroScint-40 (Packard) for counting by liquid scintillation techniques. MicroScint-40 (100 $\mu$L) is then added to each well of the cell plate to determine the remaining $^{86}Rb^+$ activity. The efflux counts are normalized for the total amount of $^{86}Rb^+$ that was in the cells by adding the efflux counts to the cell plate counts. Activity is determined by % inhibition of the efflux window that is established using a saturating concentration of margatoxin (MgTX), a 39 amino acid peptide that is a potent blocker of $K_v1.3$ channels ($IC_{50}$=100 pM).

$K_v1.5$-RUBIDIUM EFFLUX ASSAY

The Kv1.5 $^{86}Rb^+$ (a potassium ion surrogate) efflux assay utilizes HEK 293 cells engineered to stably express the human Kv1.5 potassium channel. Cells are seeded at a density of 25000 cells/well in poly-D-lysine coated 96-well Packard CulturPlates one to three days prior to the assay and loaded with $^{86}Rb^+$ (0.05 microcuries/well) the day before assay. On the day of assay, plates are washed three times using a Skatron 96-well plate washer and two hundred microliters of low KCl buffer (125 mM NaCl, 6.5 mM KCl, 1 mM $CaCl_2$, 2 mM $MgCl_2$, 0.02% bovine serum albumin, 10 mM HEPES, pH 7.2) with or without inhibitor is added to each well. After ten minutes at room temperature, the plates are washed one time with low KCl buffer and two hundred microliters of high KCl buffer (same as low KCl buffer except KCl is 60 mM and NaCl is 65 mM) with or without inhibitor is added to the appropriate wells to activate the Kv1.5 channel. The plates are incubated for an additional ten minutes at room temperature at which time one hundred microliters of each supernatant is transferred to a 96-well Packard OptiPlate. The cell plates are immediately washed one time with low KCl buffer followed by the addition of one hundred microliters of low KCl buffer to each well. One hundred microliters of Microscint scintillation cocktail is added to each well of the supernatant and cell plates and radioactivity is determined on a Packard TopCount scintillation counter. The reduction of supernatant $^{86}Rb^+$ is used to quantitate the degree of inhibition of the Kv1.5 potassium channel.

Di-TRITIUM CORREOLIDE (DiTC) BINDING ASSAY

Activity of compounds can be evaluated by determining their effect on DiTC binding to either Kv1.3 or Kv1.5 channels expressed in human embryonic kidney cells (HEK). The Kv1.3 and Kv1.5 channels used are cloned human channels. DiTC is also known as L-765,910 and is a natural product analogue which binds specifically to Kv1.x channels, such as Kv1.3 and Kv1.5. In general, compounds are incubated at given concentrations in the presence of 20 nM DiTC (10 $\mu$M cold ligand is used to define non-specific binding) and either HEK/Kv1.3 or HEK/Kv1.5 membranes, in a buffer containing 135 mM NaCl, 4.6 mM KCl, 20 mM Tris, pH=7.4 (tris[hydroxymethyl]aminomethane), and 0.02% bovine serum albumin (BSA). Binding is allowed to reach equilibrium by incubation of the samples at room temperature for 24 hrs. Separation of bound from free ligand is achieved by filtration through GF/C filters and washing with ice-cold buffer containing 100 mM NaCl, 20 mM Tris (pH=7.4), and 0.04% BSA. Scintilltion fluid is added to the samples and radioactivity associated with filters determined by liquid scintillation techniques. Specific DiTC binding is the difference between total and non-specific binding. The activity of a given compound is assessed relative to an untreated control.

HEK cells expressing either human Kv1.3 or Kv1.5 channels were grown by Analytical Biological Services in bioreactors containing MEM supplemented with FBS, Penicillin, Streptomycin, and Geneticin. Seven tubes of frozen cell pellets (25 L of cells) were then thawed and 20 mL Homogenization Buffer was added to each tube. The contents of the tubes were pooled into a 50 mL glass/Teflon homogenizer. The cells were homogenized for 10 strokes (500 rpm) and transferred to 50 mL tubes. The tubes were then centrifuged at 1000 rpm for 5 min at 4° C. (253×g, Beckman GPR). The supernatant was collected and set aside on ice. The pellets were resuspended in a total of 40 mL Lysis Buffer, homogenized as described above, and the homogenate was centrifuged as described above. The supernatant was added to the set aside supernatant. The pooled supernatant was then centrifuged at 40,000 rpm for 45 min at 4° C. (186,000×g, Beckman 45TI). The pellet was resuspended in 70 mL Storage Buffer by homogenization as described above. Aliquots were flash frozen using liquid nitrogen and stored at −70° C. (Homogenization Buffer: 250 mM Sucrose, 5 mM $MgCl_2$, 20 mM Tris, pH=7.4; Storage Buffer: 100 mM NaCl, 20 mM HEPES, pH=7.4).

DOSAGE FORMS

As an immunosuppressive, these compounds are useful in the treatment of autoimmune diseases, the prevention of rejection of foreign organ transplants and/or related afflictions, diseases and illnesses.

The compounds of this invention can be administered for the treatment of autoimmune diseases, the prevention of rejection of foreign organ transplants and/or related afflictions, diseases and illnesses according to the invention by any means that effects contact of the active ingredient compound with the site of action in the body of a warm-blooded animal. For example, administration, can be oral, topical, including transdermal, ocular, buccal, intranasal, inhalation, intravaginal, rectal, intracisternal and parenteral. The term "parenteral" as used herein refers to modes of administration which include subcutaneous, intravenous, intramuscular, intraarticular injection or infusion, intrasternal and intraperitoneal.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

For the purpose of this disclosure, a warm-blooded animal is a member of the animal kingdom possessed of a homeostatic mechanism and includes mammals and birds.

The dosage administered will be dependent on the age, health and weight of the recipient, the extent of disease, kind of concurrent treatment, if any, frequency of treatment and the nature of the effect desired. Usually, a daily dosage of active ingredient compound will be from about 1–500 milligrams per day. Ordinarily, from 10 to 100 milligrams per day in one or more applications is effective to obtain desired results. These dosages are the effective amounts for the treatment of autoimmune diseases, the prevention of rejection of foreign organ transplants and/or related afflictions, diseases and illnesses.

The active ingredient can be administered orally in solid dosage forms, such as capsules, tablets, troches, dragées, granules and powders, or in liquid dosage forms, such as elixirs, syrups, emulsions, dispersions, and suspensions. The active ingredient can also be administered parenterally, in sterile liquid dosage forms, such as dispersions, suspensions or solutions. Other dosages forms that can also be used to administer the active ingredient as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene gycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences,* A. Osol, a standard reference text in this field.

For administration by inhalation, the compounds of the present invention may be conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

For ocular administration, an ophthalmic preparation may be formulated with an appropriate weight percent solution or suspension of the compounds of Formula I in an appropriate ophthalmic vehicle, such that the compound is maintained in contact with the ocular surface for a sufficient time period to allow the compound to penetrate the corneal and internal regions of the eye.

Useful pharmaceutical dosage-forms for administration of the compounds of this invention can be illustrated as follows:

CAPSULES

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

SOFT GELATIN CAPSULES

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

TABLETS

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

INJECTABLE

A parenteral composition suitable for administration by injection is prepared by stirring 1.5% by weight of active ingredient in 10% by volume propylene glycol. The solution is made to volume with water for injection and sterilized.

SUSPENSION

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise or in conjunction with another therapeutic agent. When drugs are administered in physical combination, the dosage form and administration route should be selected depending on the compatibility of the combined drugs. Thus the term coadministration is understood to include the administration of the two agents concomitantly or sequentially, or alternatively as a fixed dose combination of the two active components.

The following examples illustrate the preparation of the compounds of Formula I and as such are not to be considered as limiting the invention set forth in the claims appended hereto.

EXAMPLE 1

1-(2-methoxyphenyl)-1-oxo-2-aza-4-phenylbutane

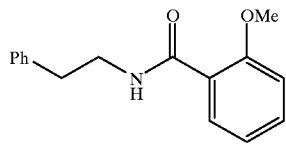

To a solution of 0.5 gm of phenethylamine (4.12 mmol) in 5 mL of dichloromethane and 0.978 mL of pyridine (8.2 mmol) at 0° C. was added 1.39 gm of 2-methoxybenzoyl chloride (1.14 mL, 8.2 mmol). The reaction was allowed to warm to room temperature and was stirred for 4 hr. The reaction mixture was concentrated, 5mL of heptane were added and the mixture was evaporated to dryness this being repeated one more time. The residue was purified by HPLC (RCM SepPak, silica 25×100, 3.6% $CH_3CN$, 14.4% $tBuOCH_3$, 82% hexane) to give the title compound.

$^1$H NMR ($CDCl_3$) δ 2.95 (m, 2H), 3.8 (s,m, 5H), 6.95 (d, 1H), 7.1 (t, 1H), 7.4 (m, 6H), 7.9 (br s, 1H), 8.2 (dd, 1H). Mass Spectrum m/e 256 ($M^+1$).

EXAMPLE 2

1-(2-methoxyphenyl)-1-oxo-2-aza-4,4-diethyl-4-phenylbutane

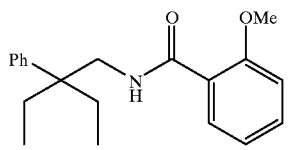

Step 1 3,3-diethyl-3-phenethylamine

To a solution of 0.25 gm of 2,2-diethylphenylacetonitrile (1.44 mmol, purchased from Sigma-Aldrich Rare Chemicals) in 10 mL of THF at room temperature, was added 7.22 mL of a 1 M solution of lithium aluminum hydride (LAH) in THF (7.22 mmol). After stirring for 12 hr, the reaction was quenched with with the successive addition of 1 mL of water, 1 mL of 15% NaOH solution and a 1 mL of water. The aluminum salts were removed by filtration and washed with 100 mL of ethylacetate. The filtrate was dried over $MgSO_4$, filtered and concentrated. The title compound was used without further purification.

Step 2 1-(2-methoxyphenyl)-1-oxo-2-aza-4,4-diethyl-4-phenylbutane

To a solution of 3,3-diethyl-3-phenethylamine (Step 1) in 5 mL of dichloromethane at room temperature was added 0.405 mL of 2-methoxybenzoyl chloride (2.7 mmol), 0.164 mL of pyridine (2.02 mmol) and 10 mg of 4,4-dimethylaminopyridine (DMAP). After stirring for 12 hr, the reaction mixture was concentrated in vacuo and purified by chromatography (silica, 2:1 hexanes:ethyl acetate). The residue was repurified by HPLC (RCM SepPak, silica 25×100, 2.6% $CH_3CN$, 10.6% $tBuOCH_3$, 86.8% hexane) to afford the title compound.

$^1$H NMR ($CDCl_3$) δ 0.8 (t, 6H), 1.8 (m, 4H), 1.8 (m, 1H), 3.55 (s, 3H), 3.8 (d, 2H), 6.85 (d, 1H), 7.05 (t, 1H), 7.35 (m, 1H), 7.4 (m, 5H), 7.65 (br s, 1H), 8.2 (dd, 1H). Mass Spectrum m/e 312 ($M^+1$).

EXAMPLE 3

1-(2-methoxyphenyl)-1-oxo-2-aza-4,4-dimethyl-4-phenylbutane

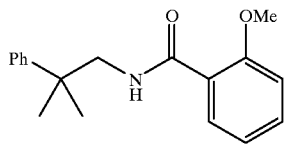

Step 1 2,2-dimethylphenylacetonitrile

To a solution of 1 gm of phenylacetonitrile (8.5 mmol) in 10 mL of anhydrous DMSO, at 0° C., was added 0.043 gm of NaH (17.1 mmol). After stirring for 0.5 hr, 1.2 mL of methyl iodide (19.6 mmol) was slowly added to the reaction mixture. After 6 hours, TLC indicated that the reaction was complete. The reaction was quenched with $H_2O$. The acqueous layer was extracted 3 times with ether. The combined organic fractions were dried over $MgSO_4$, filtered through a thin layer of silica gel and concentrated in vacuo to provide the title compound which was used without further purification.

2,2-dimethylphenylacetonitrile was converted to the title compound according to procedures described in Example 2.

$^1$H NMR ($CDCl_3$) δ 1.4 (s, 6H), 3.55 (s, 3H), 3.75 (d, 2H), 6.85 (d, 1H), 7.05 (t, 1H), 7.3 (m, 1H), 7.4 (m, 5H), 7.65 (br s, 1H), 8.2 (dd, 1H). Mass Spectrum m/e 284 ($M^+1$).

EXAMPLE 4
1-(2-methoxyphenyl)-1-oxo-2-aza-4,4-dibenzyl-4-phenylbutane

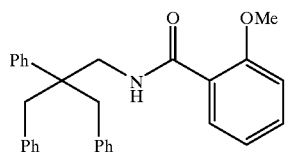

The title compound was prepared from 2,2-dibenzyl acetonitrile (Sigma-Aldrich Rare Chemicals) according to procedures described in Example 2.

$^1$H NMR (CDCl$_3$) δ 3.15 (s, 4H), 3.55 (s, 3H), 3.8 (d, 2H), 6.9 (m, 5H), 7.1 (m, 1H), 7.15 (m, 5H), 7.35 (m, 5H), 7.4 (m, 1H), 8.0 (br s, 1H), 8.2 (dd, 1H). Mass Spectrum m/e 436 (M$^+$1).

EXAMPLE 5
1-(2-methoxyphenyl)-1-oxo-2-aza-4,4-diallyl-4-phenylbutane

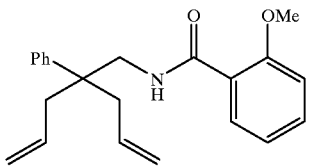

Step 1 2,2-diallylphenylacetonitrile

The title compound was prepared from phenylacetonitrile, allyl chloride and NaH as described in Example 3.

Step 2 1-(2-methoxyphenyl)-1-oxo-2-aza-4,4-diallyl-4-phenylbutane

The title compound was prepared from 2,2-diallylphenyl acetonitrile as described in Example 2.

$^1$H NMR (CDCl$_3$) δ 0.8 2.55 (m, 4H), 3.6 (s, 3H), 3.8 (d, 2H), 5.1 (m, 4H), 5.7 (m, 2H), 6.85 (d, 1H), 7.05 (t, 1H), 7.30 (m, 1H), 7.4 (m, 5H), 7. (br 70 s, 1H), 8.2 (dd, 1H). Mass Spectrum m/e 336 (M$^+$1).

EXAMPLE 6
1-(2-methoxyphenyl)-1-oxo-2-aza-4,4-di-n-propyl-4-phenylbutane

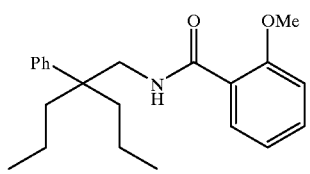

A mixture of 0.2 gm of 1-(2-methoxyphenyl)-1-oxo-2-aza-4,4-diallyl-4-phenylbutane (Example 5) in 10 mL of methanol and 0.025 gm of 5% Pd/C was hydrogenated at 40 psi (Parr Apparatus). After 12 hr, the reaction mixture was filtered through a thin pad of silica and concentrated in vacuo to afford the title compound.

$^1$H NMR (CDCl$_3$) δ 0.85 (t, 6H), 1.15 (m, 2H), 1.3 (m, 2H), 1.7 (m, 4H), 3.55 (s, 3H), 3.8 (d, 2H), 6.85 (d, 1H), 7.05 (t, 1H), 7.3 (m, 1H), 7.4 (m, 5H), 7.65 (br s, 1H), 8.2 (dd, 1H). Mass Spectrum m/e 340 (M$^+$1).

EXAMPLE 7
1-(2-methoxyphenyl)-1-oxo-2-aza-4,4-di-(3-hydroxypropyl)-4-phenylbutane

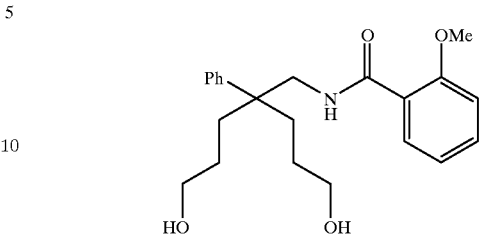

To 0.512 gm of 1-(2-methoxyphenyl)-1-oxo-2-aza-4,4-diallyl-4-phenylbutane (Example 5, 1.5 mmol) in a nitrogen atmosphere, was added 12 mL of a 0.5 M solution of 9-borabicyclo(3.3.1)nonane (9-BBN) in hexanes, and the reaction mixture was stirred at 35° C. After 4 hr, the reaction mixture was cooled to 0° C. and to it was added 5 mL of 15% NaOH solution, 2 mL of hydrogen peroxide solution (30% in water) and 3 mL of THF. After 3 hr at room temperature, the reaction mixture was extracted 3 times with ethyl acetate. The combined organic fractions were washed with 1N HCl and sat. NaHCO$_3$, dried over MgSO$_4$, filtered and concentrated. The residue was purified by chromatography (silica, 4:1, ethyl acetate: hexanes) to give the title compound.

$^1$H NMR (CDCl$_3$) δ 1.4 (m, 2H), 1.6 (m, 2H), 1.8 (m, 4H), 2.2 (br s, 2H), 3.55 (s, 3H), 3.6 (m, 4H), 3.8 (d, 2H), 6.85 (d, 1H), 7.05 (t, 1H), 7.3 (m, 1H), 7.4 (m, 5H), 7.65 (br s, 1H), 8.2 (dd, 1H). Mass Spectrum m/e 372 (M$^+$1).

EXAMPLE 8
1-(2-methoxyphenyl)-1-oxo-2-aza-4,4-di-(3-acetoxypropyl)-4-phenylbutane

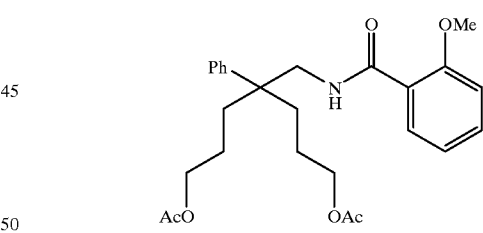

A solution of 0.085 gm of 1-(2-methoxyphenyl)-1-oxo-2-aza-4,4-di-(3-hydroxypropyl)-4-phenylbutane (Example 7, 0.23 mmol), 0.082 mL of acetic anhydride (0.69 mmol) and 0.056 mL of pyridine (0.69 mmol) in 2 mL of DMF was stirred for 12 h. The reaction mixture was concentrated, 5 mL of heptane were added and the mixture was evaporated to dryness this being reapeated one more time. The residue was purified by HPLC (RCM SepPak, silica 25×100, 5% CH$_3$CN, 20% tBuOCH$_3$, 75% hexane) to give the title compound.

$^1$H NMR (CDCl$_3$) δ 1.5 (m, 2H), 1.6 (m, 2H), 1.8 (m, 4H), 2.0 (s, 6H), 3.55 (s, 3H), 3.8 (d, 2H), 4.0 (t, 4H) 6.85 (d, 1H), 7.05 (t, 1H), 7.3 (m, 1H), 7.4 (m, 5H), 7.65 (br s, 1H), 8.2 (dd, 1H). Mass Spectrum m/e 456 (M$^+$1).

EXAMPLE 9

1-(2-methoxyphenyl)-1-oxo-2-aza-4,4-di-(2-hydroxyethyl)-4-phenylbutane

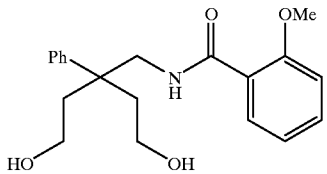

A solution of 500 mg of 1-(2-methoxyphenyl)-1-oxo-2-aza-4,4-diallyl-4-phenylbutane (1.5 mmol) in 5 mL of methanol and 5 mL of methylene chloride was cooled to −78° C. Ozone was bubbled through the reaction mixture for 20 min. until tlc (silica, 9:1 $CH_2Cl_2$:$CH_3OH$) showed no more starting material. 0.5 gm of $NaBH_4$ was then added to the reaction mixture and it was warmed to room temperature. After 0.5 hr 20 mL of 1N aqueous HCl were carefully added and the mixture extracted with $CH_2Cl_2$. The combined organic extracts were washed with brine, dried over magnesium sulfate, filtered, and concentrated. The residue was purified by chromatography (silica, 9:1 ethyl acetate:hexanes) to give the title compound.

$^1$H NMR (CDCl$_3$) δ 2.0 (t, 4H), 3.55 (m, 4H), 3.7 (s, 3H), 3.9 (s, 2H), 4.0 (t, 4H), 7.0 (m, 2H), 7.3 (m, 1H), 7.4 (m, 6H), 8.0 (dd, 1H). Mass Spectrum m/e 344 (M$^+$1).

EXAMPLE 10

1-(2-methoxyphenyl)-1-oxo-2-aza-4,4-di-(2-acetoxyethyl)-4-phenylbutane

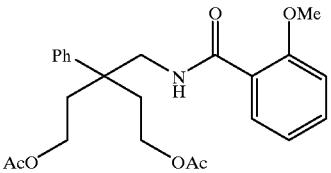

The title compound was prepared from 1-(2-methoxyphenyl)-1-oxo-2-aza-4,4-di-(2-hydroxyethyl)-4-phenylbutane (Example 9) according to procedures described in Example 8.

$^1$H NMR (CDCl$_3$) δ 2.0 (s, 6H), 2.2 (t, 4H), 3.6 (s, 3H), 3.9 (d, 2H), 4.1 (m, 4H) 6.85 (d, 1H), 7.05 (t, 1H), 7.3 (m, 1H), 7.4 (m, 5H), 7.65 (br s, 1H), 8.2 (dd, 1H). Mass Spectrum m/e 428 (M$^+$1).

EXAMPLE 11

1-(2-methoxyphenyl)-1-oxo-2-aza-(R)-ethyl-4-phenylbutane

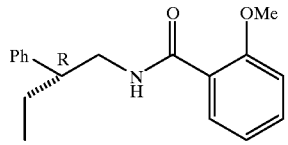

Step 1 (R)-(−)-2-phenylbutanol

To a suspension of 2.3 gm of LAH (60.6 mmol) in 70 mL of THF was slowly added a solution of 5 gm of (R)-(−)-2-phenylbutyric acid (30.45 mmol, Aldrich) in 30 mL of THF. The reaction mixture was heated to 60° C. for 3 hr. The reaction was cooled to 0° C. and to it was successively added 2 mL of water, 2 mL of 1N KOH and 2 mL of water. The aluminum salts were removed by filtration and washed with 100 mL of ethylacetate. The filtrate was dried over MgSO$_4$, filtered and concentrated to give the title compound which was used without purification.

$^1$H NMR (CDCl$_3$) δ 0.9 (t, 3H), 1.6 (m, 2H), 1.8 (m, 2H), 2.2 (be s, 1H), 2.7 (m, 1H), 3.75 (m, 2H), 7.3 (m, 5H).

Step 2 (R)-(−)-2-phenylbutyl amine

To a solution of 4.7 gm of (R)-(−)-2-phenylbutanol (31.78 mmol) and 7.6 mL of pyridine (95 mmol) in 40 mL of $CH_2Cl_2$ was added 10 gm of methanesulfonic anhydride (64 mmol). After stirring at room temperature for 5 hr, 100 mL of water was added and the mixture was extracted 3 times with ether. The combined organic fractions were washed with 1N HCl, sat. NaHCO$_3$ and sat. NaCl solutions. The organic fractions were dried over MgSO$_4$, filtered through a thin layer of silica and concentrated in vacuo. The methanesulfonate was used without further purification. $^1$H NMR (CDCl$_3$) δ 0.85 (t, 3H), 1.65 (m, 2H), 1.85 (m, 2H), 2.75 (s, 3H), 2.9 (m, 1H), 4.35 (d, 2H), 7.3 (m, 5H). A solution of the methanesulfonate, 10 gm of sodium azide (154 mmol) and a trace amount of sodium iodide in 50 mL of DMF was stirred at 80° C. for 12 hr. The reaction mixture was then cooled and 200 mL of ether was added. The mixture was washed 3 times with water, then with sat. NaCl solution, dried over MgSO$_4$, filtered and concentrated. To a solution of the azide in 20 mL of THF was added 50 mL of a 1M solution of LAH in THF and the reaction mixture was stirred at room temperature. After 2 hours, the reaction was quenched with successive additions of 5 mL of water, 5 mL of 10% KOH and 5 mL of water. The aluminum salts were removed by filtration and washed with 200 mL of ethylacetate. The filtrate was dried over MgSO$_4$, filtered and concentrated. The residue was purified by vacuum distillation in a Kugelrohr apparatus (bp 145° C., 0.2 Torr) to give the title compound as a clear liquid.

Step 3 1-(2-methoxyphenyl)-1-oxo-2-aza-4-(R)-ethyl-4-phenylbutane

The title compound was prepared from 0.2 gm of (R)-(−)-2-phenylbutyl amine and 2-mL of 4 methoxybenzoyl chloride according to procedures described in Example 2.

$^1$H NMR (CDCl$_3$) δ 0.87 (t, 3H), 1.66 (m, 1H), 1.8 (m, 1H), 2.8 (m, 1H), 3.4 (m, 1H), 3.55 (s, 3H), 4.05 (m, 1H), 6.87 (d, 1H), 7.03 (t, 1H), 7.3 (m, 6H), 7.75 (br s, 1H), 8.2 (dd, 1H). Mass Spectrum m/e 284 (M$^+$1), α$_D$ (CHCl3)=30.2.

EXAMPLE 12

1-(2-methoxyphenyl)-1-oxo-2-aza-4-(S)-ethyl-4-phenylbutane

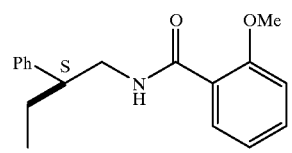

The title compound was prepared from (S)-(+)-2-phenyl butyric acid according to procedures described in Example 11.

$^1$H NMR (CDCl$_3$) same as Example 11, Step 3 Mass Spectrum m/e 284 (M$^+$1), α$_D$ (CHCl3)=−29.7.

EXAMPLE 13

1-(2-methoxyphenyl)-1-oxo-2-aza-4-(R)-methyl-4-phenylbutane

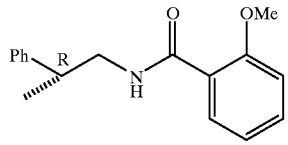

The title compound was prepared from (R)-(−)-2-phenyl propionic acid according to procedures described in Example 11.

$^1$H NMR (CDCl$_3$) δ 1.4 (d, 3H), 3.1 (m, 1H), 3.5 (m, 1H), 3.6 (s, 3H), 3.95 (m, 1H), 6.85 (d, 1H), 7.05 (t, H), 7.35 (m, 6H), 7.8 (br s, 1H), 8.2 (dd, 1H). Mass Spectrum m/e 270 (M$^+$1), α$_D$ (CHCl3)=+34.25.

EXAMPLE 14

1-(2-methoxyphenyl)-1-oxo-2-aza-4-(S)-methyl-4-phenylbutane

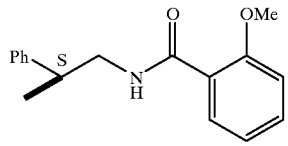

The title compound was prepared from (S)-(+)-2-phenyl propionic acid according to procedures described in Example 11.

$^1$H NMR (CDCl$_3$) same as Example 13. Mass Spectrum m/e 270 (M$^+$1), α$_D$ (CHCl3)=−35.05.

EXAMPLE 15

1-(2-methoxyphenyl)-1-oxo-2-aza--(S)-4-i-propyl-4-phenylbutane

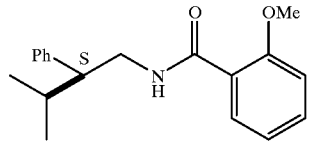

The title compound was prepared from (S)-(+)-2-phenyl-3-methylbutyric acid (Aldrich) according to procedures described in Example 11.

$^1$H NMR (CDCl$_3$) d 0.75 (d, 3H), 1.0 (d, 3H), 1.85 (m. 1H), 2.5 (m, 1H), 3.35 (m, 4H), 4.2 (m, 1H), 6.7 (d, 1H), 6.95 (t, 1H), 7.2 (m, 6H), 7.6 (br s, 1H), 8.14 (dd, 1H). Mass Spectrum m/e 298 (M$^+$1), α$_D$ (CHCl3)=−19.8.

EXAMPLE 16

1-(2-methoxyphenyl)-1-oxo-2-aza-4-(S)-allyl-4-phenylbutane

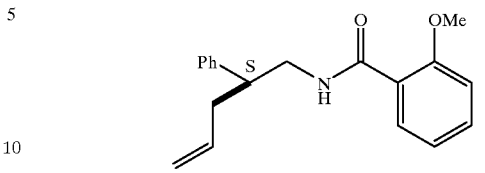

Step 1 3-Phenylacetyl-4-(S)-benzyl-2-oxazolidinone

A solution of 10 gm of phenylacetic acid (73 mmol) and 12.2 mL of triethylamine (87.6 mmol) in 200 mL of THF was cooled to −78° C. To this solution was added 9.8 mL of trimethylacetyl chloride (80 mmol) and the reaction was warmed to 0° C. and stirred for 1 hr. This solution was recooled to −78° C. (Solution #1) Meanwhile, to a solution of 14.2 gm of (S)-(−)-4-benzyl-2-oxazolidinone in 200 mL of THF at −78° C., was added 50 mL of a 1.6M solution of n-butyl lithium in THF (80 mmol) over 20 min. (Solution #2) After stirring for 20 min., this solution (#2) was slowly cannulated into the solution (#1) containing the mixed anhydride at −78° C. This reaction mixture was allowed to warm to room temperature and stirred for 2 hr. The reaction was quenched with a solution of saturated NH$_4$Cl and extracted with ethyl acetate. The combined organic fractions were washed with water, sat. NaHCO$_3$ solution, sat. NaCl solution, dried over MgSO$_4$, filtered and concentrated. The crude product was purified by chromatograpy (silica, hexanes:ethyl; acetate=4:1) to give the title compound.

Step 2 3-(2-Phenyl-2-(S)-allylacetyl)-4-(S)-benzyl-2-oxazolidinone

To a solution of 15.5 gm of 3-phenylacetyl-4-(S)-benzyl-2-oxazolidinone (52 mmol) in 100 mL of THF at −78° C. in a nitrogen atmosphere was added dropwise 63 mL of a 1M solution of lithium bis(trimethylsilyl)azide (63 mmol). The reaction mixture was warmed to 0° C. over the period of 1 hr and then recooled to −78° C. To the reaction mixture was added 5.3 mL of allyl iodide (57 mmol). The reaction mixture was slowly warmed to room temperature and stirred for 12 hr. The reaction was quenched with saturated NH$_4$Cl solution and the mixture was extracted with ethyl acetate. The combined organic fractions were washed with solutions of saturated NaHCO$_3$ and NaCl, dried over MgSO$_4$, filtered and concentrated. The residue was purified by chromatography (silica, 2:1 hexanes:ethyl acetate) to give the title compound.

$^1$H NMR (CDCl$_3$) δ 2.5 (m, 1H), 2.8 (ABq, 1H), 3.00 (m, 1H), 3.35 (d, 1H), 4.1 (m, 2H), 5.1 (d,1H), 5.1.5 (d, 1H), 5.2 (t, 1H), 5.8 (m, 1H), 7.3 (m, 10H).

Step 3 2-(S)-allyl-2-phenethanol

To a suspension of 4.57 gm of LAH (115 mmol) in 150 mL of THF at 0° C. was added a solution of 19.2 gm of 3-(2-Phenyl-2-(S)-allylacetyl)-4-(S)-benzyl-2-oxazolidinone (57 mmol) in 100 mL of THF. The reaction mixture was stirred for 12 hr at room temperature. The reaction was quenched with 10 mL of water, and the pH was lowered to pH=1 with a 2N solution of H$_2$SO$_4$. The mixture was extracted with ethyl acetate and the combined organic fractions were dried over MgSO$_4$, filtered and concentrated. The title compound was used without further purification.

$^1$H NMR (CDCl$_3$) δ 1.4 (br s, 1H), 2.45 (m, 2H), 2.9 (m, 1H), 3.8 (m, 2H), 5.0 (d,1H), 5.05 (d, 1H), 5.75 (m, 1H), 7.3 (m, 5H).

Step 4 2-(S)-allyl-2-phenethyl bromide

To a solution of 18.5 gm of triphenylphosphine (70.6 mmol) in 200 mL of anhydrous ether at room temperature was added 23.3 gm of carbon tetrabromide (70.6 mmol). After stirring for 30 min, a solution of 6.76 gm of 3-(2-Phenyl-2-(S)-allylethanol (44.1 mmol) in 50 mL of ether was added dropwise and the reaction was allowed to stir for 12 hr. The reaction mixture was filtered and the filtercake was washed with ether. The combined ether fractions were washed with solutions of saturated NaHCO$_3$ and NaCl, dried over MgSO$_4$, filtered and concentrated. The residue was purified by chromatography (silica, 4:1, hexanes:ethyl acetate) to give the title compound.

$^1$H NMR (CDCl$_3$) δ 2.5 (m, 1H), 2.65 (m, 1H), 3.05 (m, 1H), 3.6 (m, 2H), 5.0 (d,1H), 5.05 (d, 1H), 5.65 (m, 1H), 7.3 (m, 5H).

Step 5 2-(S)-allyl-2-phenethyl amine

To a solution of 8.6 gm of 2-(S)-allyl-2-phenethyl bromide (37 mmol) in 60 mL of DMF was added 13.7 gm of potassium phthalimide (74 mmol, Aldrich) and the reaction mixture was heated at 78° C. for 12 hr. The reaction was quenched with water and the mixture was extracted with ethyl acetate. The combined organic fractions were washed with solutions of saturated NaHCO$_3$ and NaCl, dried over MgSO$_4$, filtered and concentrated. The residue was purified by chromatography (silica, 9:1, hexanes:ethyl acetate) to give 4.77 gm of the phthalimide inetrmediate. A solution of the phthalimide and 2.2 mL of hydrazine hydrate (70.5 mmol) in 50 mL of ethanol was stirred for 3 hr. The reaction mixture was diluted with water, made acidic with HCl and washed with ethyl acetate. The aqueous layer was then made basic with a solution of 1N KOH and extracted with ether. The combined ether fractions were washed with solutions of saturated NaHCO$_3$ and NaCl, dried over MgSO$_4$, filtered and concentrated to give the title compound, which was used without further purification.

$^1$H NMR (CDCl$_3$) δ 1.9 (br S, 2H), 2.4 (m, 2H), 2.7 (m, 1H), 2.8 (m, 1H), 3.0 (m, 1H), 4.95 (d,1H), 5.0 (d, 1H), 5.7 (m, 1H), 7.3 (m, 5H).

Step 5 1-(2-methoxyphenyl)-1-oxo-2-aza-4-(S)-allyl-4-phenylbutane

The title compound was prepared from 2-(S)-allyl-2-phenethyl amine and 4 methoxybenzoyl chloride according to procedures described in Example 2.

$^1$H NMR (CDCl$_3$) δ 2.45 (m, 2H), 3.0 (m, 1H), 3.45 (m, 1H), 3.55 (s, 3H), 4.05 (m, 1H), 4.95 (d, 1H), 5.05 (d, 1H), 5.7 (m, 1H), 6.8 (d, 1H), 7.0 (t, 1H), 7.3 (m, 6H), 7.8 (br s, 1H), 8.2 (dd, 1H). Mass Spectrum m/e 296 (M$^+$1), α$_D$ (CHCl$_3$)=−14.3

EXAMPLE 17
1-(2-methoxyphenyl)-1-oxo-2-aza-4-(R)-allyl-4-phenylbutane

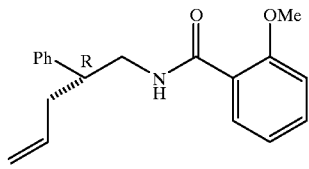

The title compound was prepared according to procedures described in Example 16, with the exception that (R)-(−)-4-benzyl-2-oxazolidinone was used as the chiral auxiliary.

$^1$H NMR (CDCl$_3$) same as for Example 16, Step 5. Mass Spectrum m/e 296 (M$^+$1), α$_D$ (CHCl$_3$)=+14.27.

EXAMPLE 18
1-(2-methoxyphenyl)-1-oxo-2-aza-(S)-4-i-butyl-4-phenylbutane

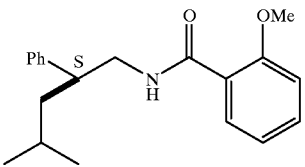

Step 1 2-(S)-i-butyl-2-phenethanol

The title compound was prepared according to procedures described in Example 16, Steps 1–3.

Step 2 1-(2-methoxyphenyl)-1-oxo-2-aza-4-(S)-i-butyl-4-phenylbutane 2-(S)-i-butyl-2-phenethanol was converted to the title compound according to procedures described in Example 11, Steps 2 and 3.

$^1$H NMR (CDCl$_3$) δ 0.9 (t, 6H), 1.5 (m, 3H), 1.65 (m, 2H), 3.0 (m, 1H), 3.35 (m, 1H), 3.55 (s, 3H), 6.8 (d, 1H), 7.0 (t, 1H), 7.3 (m, 6H), 7.8 (br s, 1H), 8.2 (dd, 1H). Mass Spectrum m/e 312 (M$^+$1), α$_D$ (CHCl$_3$)=−21.4

EXAMPLE 19
1-(2-methoxyphenyl)-1-oxo-2-aza-4-(S)-n-propyl-4-phenylbutane

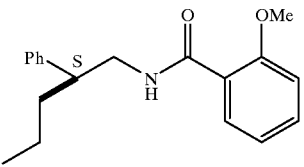

The title compound was prepared from 1-(2-methoxyphenyl)-1-oxo-2-aza-3-(S)-allyl-4-phenylbutane according to procedures described in Example 6.

$^1$H NMR (CDCl$_3$) δ 0.9 (t, 3H), 1.3 (m, 2H), 1.7 (m, 3H), 2.9 (m, 1H), 3.4 (m, 1H), 3.6 (s, 3H), 4.05 (m, 1H), 6.85 (d, 1H), 7.05 (t, 1H), 7.35 (m, 6H), 7.8 (br s, 1H), 8.2 (dd, 1H). Mass Spectrum m/e 298 (M$^+$1), α$_D$ (CHCl$_3$)=−22.4

EXAMPLE 20
1-(2-methoxyphenyl)-1-oxo-2-aza-4-(S)-(3-hydroxypropyl)-4-phenylbutane

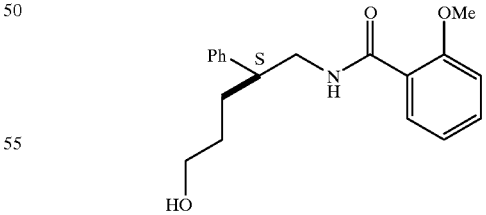

The title compound was prepared from 1-(2-methoxyphenyl)-1-oxo-2-aza-4-(S)-allyl-4-phenylbutane according to procedures described in Example 7.

$^1$H NMR (CDCl$_3$) δ 1.5 (m, 2H), 1.6 (Br s, 1H), 1.85 (m, 2H) 2.9 (m, 1H), 3.45 (m, 1H), 3.6 (s, m, 5H), 4.00 (m, 1H), 6.85 (d, 1H), 7.05 (t, 1H), 7.35 (m, 6H), 7.8 (br s, 1H), 8.2 (dd, 1H). Mass Spectrum m/e 314 (M$^+$1), α$_D$ (CHCl$_3$)=−19.6

EXAMPLE 21

1-(2-methoxyphenyl)-1-oxo-2-aza-4-(S)-((3-allylcarbamoyloxy)propyl))-4-phenylbutane

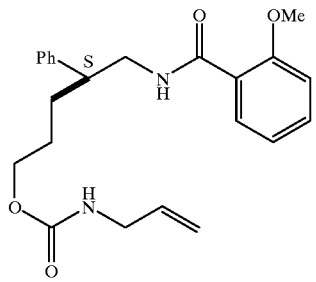

To solution of 0.2 gm of 1-(2-methoxyphenyl)-1-oxo-2-aza-4-(S)-(3-hydroxypropyl)-4-phenylbutane (0.638 mmol) in 5 mL of dichloromethane and 0.176 mL of triethylamine (1.27 mmol) and 0.116 gm of DMAP (0.96 mmol) was added 0.19 gm of 4-nitrophenyl chloroformate and the reaction was stirred at rt. After 3 hr, the reaction mixture was concentrated and purified by chromatography (silica, hexane:ethyl acetate=1:1) to give the 4-nitrophenyl carbonate intermediate. The carbonate was redissolved in 2 mL of dichloromethane and to it was added 0.18 mL of allylamine (2.4 mmol) and the reaction was stirred for 12 hr at rt. The reaction mixture was washed with saturated $NaHCO_3$, 3N HCl and NaCl, dried over $MgSO_4$, filtered and concentrated. The residue was purified by chromatography (silica, silica, hexane:ethyl acetate=1:1) to give the title compound.

$^1$H NMR (CDCl$_3$) δ 1.6 (m, 2H), 1.7 (m, 1H), 1.85 (m, 1H) 2.9 (m, 1H), 3.4 (m, 1H), 3.6 (s, 3H), 3.8 (m, 1H), 4.1 (m, 4H), 4.95 (br s, 1H), 5.1 (d, 1H), 5.2 (d, 1H), 5.8 (br s, 1H), 6.85 (d, 1H), 7.05 (t, 1H), 7.3 (m, 6H), 7.8 (br s, 1H), 8.2 (dd, 1H). Mass Spectrum m/e 397 (M$^+$1), α$_D$ (CHCl$_3$)=−21.4

EXAMPLE 22

1-(2-methoxyphenyl)-1-oxo-2-aza-4-(S)-((3-allyloxycarbonyloxy)propyl))-4-phenylbutane

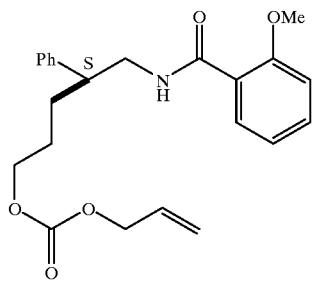

The title compound was prepared from 1-(2-methoxyphenyl)-1-oxo-2-aza-4-(S)-(3-hydroxypropyl)-4-phenylbutane according to procedures described in Example 21 with the exception that allylchloroformate was used.

$^1$H NMR (CDCl$_3$) δ 1.6 (m, 1H), 1.65 (m, 1H), 1.7 (m,1H), 1.9 (m, 1H) 2.9 (m, 1H), 3.4 (m, 1H), 3.6 (s, 3H), 4.0 (m, 1H), 4.1 (m, 2H), 4.6 (d, 2H), 5.25 (d, 1H), 5.35 (d, 1H), 5.9 (m, 1H), 6.85 (d, 1H), 7.05 (t, 1H), 7.3 (m, 6H), 7.8 (br s, 1H), 8.2 (dd, 1H). Mass Spectrum m/e 398 (M$^+$1), α$_D$ (CHCl$_3$)=−12.6

EXAMPLE 23

1-(2-methoxyphenyl)-1-oxo-2-aza-4-(R)-n-propyl-4-phenylbutane

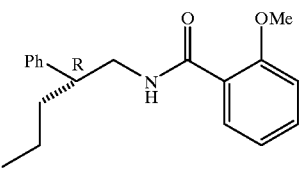

The title compound was prepared from 1-(2-methoxyphenyl)-1-oxo-2-aza-4-(R)-allyl-4-phenylbutane (Example 17) according to procedures described in Example 6.

$^1$H NMR (CDCl$_3$) δ 0.9 (t, 3H), 1.3 (m, 2H), 1.7 (m, 3H), 2.9 (m, 1H), 3.4 (m, 1H), 3.6 (s, 3H), 4.05 (m, 1H), 6.85 (d, 1H), 7.05 (t, 1H), 7.35 (m, 6H), 7.8 (br s, 1H), 8.2 (dd, 1H). Mass Spectrum m/e 298 (M$^+$1), α$_D$ (CHCl$_3$)=+22.7

EXAMPLE 24

1-(2-methoxyphenyl)-1-oxo-2-aza-4-(R)-(3-hydroxypropyl)-4-phenylbutane

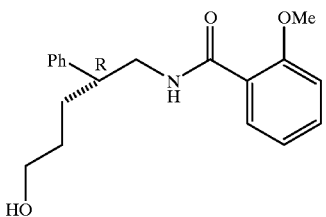

The title compound was prepared from 1-(2-methoxyphenyl)-1-oxo-2-aza-4-(R)-allyl-4-phenylbutane according to procedures described in Example 7.

$^1$H NMR (CDCl$_3$) δ 1.5 (m, 2H), 1.6 (Br s, 1H), 1.85 (m, 2H) 2.9 (m, 1H), 3.45 (m, 1H), 3.6 (s, m, 5H), 4.00 (m, 1H), 6.85 (d, 1H), 7.05 (t, 1H), 7.35 (m, 6H), 7.8 (br s, 1H), 8.2 (dd, 1H). Mass Spectrum m/e 314 (M$^+$1), α$_D$ (CHCl$_3$)=+18.2

EXAMPLE 25

1-(2-methoxyphenyl)-1-oxo-2-aza-3-(R)-((3-allylcarbamoyloxy)propyl))-4-phenylbutane

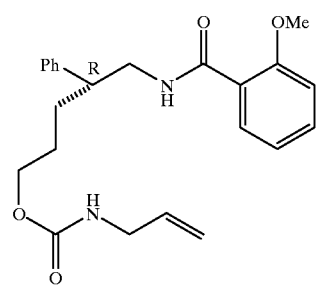

The title compound was prepared from 1-(2-methoxyphenyl)-1-oxo-2-aza-4-(R)-(3-hydroxypropyl)-4-phenylbutane according to procedures described to Example 21.

¹H NMR (CDCl₃) δ 1.6 (m, 2H), 1.7 (m, 1H), 1.85 (m, 1H) 2.9 (m, 1H), 3.4 (m, 1H), 3.6 (s, 3H), 3.8 (m, 1H), 4.1 (m, 4H), 4.95 (br s, 1H), 5.1 (d, 1H), 5.2 (d, 1H), 5.8 (br s, 1H), 6.85 (d, 1H), 7.05 (t, 1H), 7.3 (m, 6H), 7.8 (br s, 1H), 8.2 (dd, 1H). Mass Spectrum m/e 397 (M⁺1), α_D (CHCl₃)=+ 19.8

EXAMPLE 26
1-(2-methoxyphenyl)-1-oxo-2-aza-4-(R)-((3-allyloxycarbonyloxy)propyl))-4-phenylbutane

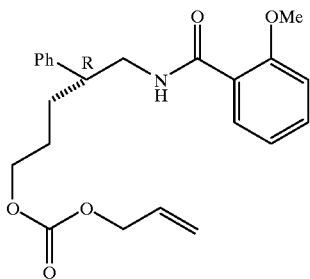

The title compound was prepared from 1-(2-methoxyphenyl)-1-oxo-2-aza-4-(R)-(3-hydroxypropyl)-4-phenylbutane according to procedures described in Example 21 with the exception that allylchloroformate was used.

¹H NMR (CDCl₃) δ 1.6 (m, 1H), 1.65 (m, 1H), 1.7 (m,1H), 1.9 (m, 1H) 2.9 (m, 1H), 3.4 (m, 1H), 3.6 (s, 3H), 4.0 (m, 1H), 4.1 (m, 2H), 4.6 (d, 2H), 5.25 (d, 1H), 5.35 (d, 1H), 5.9 (m, 1H), 6.85 (d, 1H), 7.05 (t, 1H), 7.3 (m ,6H), 7.8 (br s, 1H), 8.2 (dd, 1H). Mass Spectrum m/e 398 (M⁺1), α_D (CHCl₃)=+12.6.

EXAMPLE 27
1-(2-methoxyphenyl)-1-oxo-2-aza-4-hydroxyethyl-4-(4-oxy-3-oxopentanyl)-4-phenylbutane

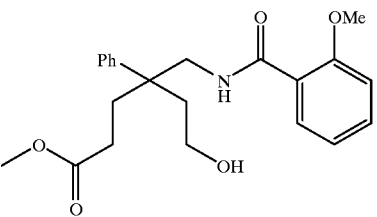

Step 1 4-cyano-4-phenylcyclohexanone ethyleneglycol ketal

A solution of 20 gm of 4-cyano-4-phenylcyclohexanone (Aldrich, 100.5 mmol), 60 ml of ethylene glycol, and 1.10 gm of TsOH in 65 ml of toluene was refluxed for 12 hr. The water formed during the reaction was removed via a Dean-Stark distillation receiver. The reaction mixture was concentrated under reduced pressure to remove the solvent and the residue was poured into 200 ml of ether. It was washed with water (20 ml×3), dried over MgSO₄ and concentrated. The residue was purified by recrystallization with hexanes:ether to afford the title compound as a white solid.

Step 2 4-aminomethyl-4-phenylcyclohexanone ethyleneglycol ketal

To a suspension of 10.00 g (41.1 mmol) of 4-cyano-4-phenylcyclohexanone ethylene glycol ketal in 50 ml of dry THF was slowly added 61.65 ml of lithium aluminum hydride (1.0 M in THF, 61.65 mmol) and the reaction mixture was refluxed for 3 hr. When TLC showed no starting material the reaction mixture was cooled to 0° C. and quenched with 4 ml of 4N NaOH at 0° C. The reaction mixture was filtered through a plug of Na₂SO₄ and concentrated to give the title compound as a colorless oil.

Step 3 4-Phenyl-4-(3-(2-methoxyphenyl)-3-oxo-2-azaprop-1-yl) cyclohexanone

To a solution of 6.06 g (24.5 mmol) of 4-aminomethyl-4-phenylcyclohexanone ethyleneglycol ketal and 6.50 ml of triethylamine (49.0 mmol) in 60 ml of methylene chloride was added 5.44 g (31.9 mmol) of o-anisoyl chloride at 0° C. The reaction mixture was stirred for 3 hr and was poured into 200 ml of ether. It was washed with aq NaHCO₃, dried over MgSO₄ and concentrated. Then 150 ml of THF and 50 ml of 2N HCl was added into the residue. The reaction mixture were stirred for 3 hr at 40° C. Then it was poured into 200 ml of ether. The organic layer was washed with aq NaHCO₃, dried over MgSO₄ and concentrated. The residue was purified by chromatography (silica, hexanes:ethyl acetate, 1:1) to afford the compound as a solid.

Step 4 5-phenyl-4-(3-(2-methoxyophenyl)3-oxo-2-azapropyl)-1-oxy-2-oxocycloheptane

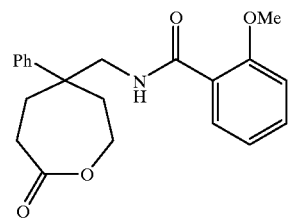

A solution of 0.044 gm of 4-phenyl-4-(3-(2-methoxyphenyl)3-oxo-2-aza-propyl)-cyclohexanone (Lancaster Chemical Co., 0.13 mmol) and 0.15 gm of 3-chloro peroxybenzoic acid (0.87 mmol) in 10 mL of CH₂Cl₂ was stirred at rt for 72 hr and was filtered through a plug of silica gel. The residue was purified by HPLC (Waters RCM 25×10, with CH₃CN:tBuOMe:Hexane (1:4:5)/Hexane=6.75/6.0 nL/min) to give the title compound as a white solid.

¹H NMR (CDCl₃) δ 8.16 (d of d, 1H, J=1.3, 7.7 Hz); 7.63 (t, 1H, J=5.5 Hz), 7.47 (t, 2H, J=7.6 Hz), 7.41 (t of d, 1H, J=1.1, 8.2 Hz), 7.34–7.39 (m, 3H), 4.36 (d of d, 1H, J=7.1, 13.3 Hz), 4.13 (d of d, 1H, J=9.1, 13.2 Hz), 3.64–3.73 (m, 2H), 3.62 (s, 3H), 2.72 (d of d, 1H, J=9.1, 14.2 Hz), 2.54–2.61 (m, 2H), 2.45 (d of d, 1H, J=14.2, 8.9 Hz), 2.11 (d of d, 1H, J=9.1, 16 Hz), 2.02 (d of d, 1H, J=11.6, 14.4 Hz); Mass Spectrum (CI) m/e 354 (M+1)

Step 5 1-(2-methoxyphenyl)-1-oxo-2-aza-4hydroxyethyl-4-(4-oxy-3-oxo-pentanyl)-4-phenylbutane A solution of 0.0081 gm of 5-phenyl-4-(3-(2-methoxyophenyl)3-oxo-2-aza-propyl)-1-oxy-2-oxocycloheptane (0.023 mmol) and 0.0065 gm of potassium carbonate (0.047 mmol) in 4 mL of methanol was stirred at rt for 14 hr and solvent was removed. The residue was dissolved in EtOAc and filtered through a plug of silica gel to give the title compound.

¹H NMR (CDCl₃) δ 8.19 (d of d, 1H, J=1.7, 7.8 Hz); 7.99 (bs 1H), 7.37–7.45 (m, 5H), 7.27–7.29 (m, 1H), 7.07 (t, 1H, J=7.7 Hz), 6.90 (d, 1H, J=8.5 Hz), 4.05 (d of d, 1H, J=7.1, 13.8 Hz), 3.80 (d of d, 1H, J=5.5, 14.0 Hz), 3.60–3.73 (m, 2H), 3.66 (s, 3H), 3.62 (s, 3H), 1.98–2.25 (m, 7H); Mass Spectrum (CI) m/e 386 (M+1)

EXAMPLE 28

1-(2-methoxyphenyl)-1-oxo-2-aza-4-hydroxyethyl-4-(8-phenyl-4-oxy-3-oxo-octanyl)-4-phenylbutane

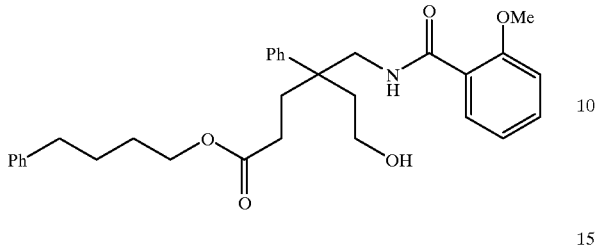

A solution of 0.01 gm of 5-phenyl-4-(3-(2-methoxyophenyl)3-oxo-2-aza-propyl)-1-oxy-2-oxocycloheptane (0.028 mmol), 0.005 mg potassium carbonate (0.036 mmol) and (0.042 gm, 0.28 mmol) of 4-phenyl-1-butanol in 1.0 mL of DMF was heated to 80° C. for 14 hr and solvent was removed. The residue was dissolved in EtOAc and filtered through a plug of silica gel. It was purified by HPLC (Waters RCM 25×10, with CH$_3$CN:tBuOMe:Hexane (1:4:5)/Hexane=6.75/6.0 mL/min) to give the title compound.

$^1$H NMR (CDCl$_3$) δ 8.19 (d, 1H, J=7.8 Hz), 8.01 (t, 1H, J=5.8 Hz), 7.16–7.44 (m, 11H), 7.06 (t, 1H, J=7.5 Hz), 6.89 (d, 1H, J=8.5 Hz), 4.01–4.04 (m, 3H), 3.80 (d of d, 1H, J=5.5, 13.8 Hz), 3.62–3.75 (m, 2H), 3.65 (s, 3H), 2.79 (bs, 1H), 2.63 (t, 2H, J=7.0 Hz), 1.98–2.25 (m, 6H), 1.63–1.67 (m, 4H); Mass Spectrum (CI) m/e 504 (M+1).

EXAMPLE 29

1-(2-methoxyphenyl)-1-oxo-2-aza-4-hydroxyethyl-4-(4-oxy-3-oxo-hept-6-enyl)-4-phenylbutane

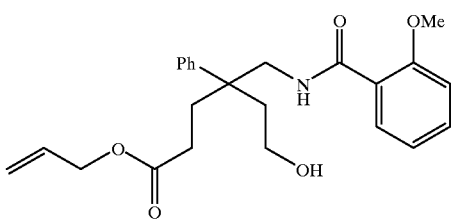

The title compound was prepared from 30.6 mg 5-phenyl-4-(3-(2-methoxyophenyl)3-oxo-2-aza-propyl)-1-oxy-2-oxocycloheptane as in Example 28 with the exception that allyl alcohol was used and the reaction was stirred at 40° C. for 14 hr.

$^1$H NMR (CDCl$_3$) δ 8.16 (d of d, 1H, J=1.4, 7.8 Hz); 8.01 (t, 1H, J=5.5 Hz), 7.37–7.42 (m, 5H), 7.25–7.28 (m, 1H), 7.03 (t, 1H, J=7.5 Hz), 6.87 (d, 1H, J=8.2 Hz), 5.85 (m, 1H), 5.28 (d of d, 1H, J=1.3, 17.2Hz), 5.19 (d, 1H, J=11.4 Hz), 4.50 (d, 2H, J=5.7 Hz), 4.01 (d of d, 1H, J=6.8, 13.7 Hz), 3.77 (d of d, 1H, J=5.5, 13.7 Hz), 3.59–3.72 (m, 2H), 3.64 (s, 3H), 2.96 (bs, 1H),1.97–2.27 (m, 6H); Mass Spectrum (CI) m/e 412 (M+1)

EXAMPLE 30

1-(2-methoxyphenyl)-1-oxo-2-aza-4-acetoxyethyl-4-(4-oxy-3-oxo-hept-6-enyl)-4-phenylbutane

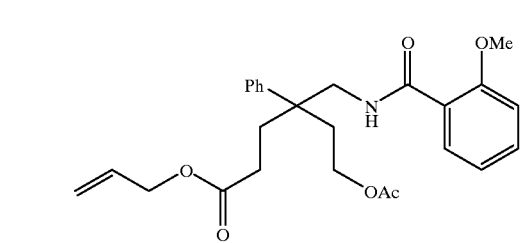

A solution of 0.0095 gm of 1-(2-methoxyphenyl)-1-oxo-2-aza-4-hydroxyethyl-4-(4-oxy-3-oxo-hept-6-enyl)-4-phenylbutane (0.023 mmol), 0.0018 gm of DMAP, 0.05 mL of Ac$_2$O and 0.1 mL of pyridine in 2.0 mL of THF was stirred at rt for 14 hr and volatiles were removed under vacuum. The residue was dissolved in CH$_2$Cl$_2$ and filtered through a plug of silica gel, purified by HPLC (Waters RCM 25×10, with CH$_3$CN:tBuOMe:Hexane (1:4:5)/Hexane= 6.75/6.0 mL/min) conditions) to afford the title compound.

$^1$H NMR (CDCl$_3$) δ 8.18 (d of d, 1H, J=1.8, 7.8 Hz), 7.80 (t, 1H, J=5.3 Hz), 7.39–7.42 (m, 5H), 7.27–7.32 (m, 1H), 7.05 (t, 1H, J=7.8 Hz), 6.88 (d, 1H, J=8.2 Hz), 5.83–5.90 (m, 1H), 5.27 (d, 1H, J=15.2 Hz), 5.20 (d, 1H, J=10.3Hz), 4.52 (d, 2H, J=5.7Hz), 4.07 (t, 2H, J=7.1 Hz), 3.91 (d of d, 1H, J=6.0, 13.8 Hz), 3.83 (d of d, 1H, J=5.5, 13.7 Hz), 3.63 (s, 3H), 2.29–2.38 (m, 2H), 2.11–2.18 (m, 4H), 1.96 (s, 3H); Mass Spectrum (CI) m/e 454 (M+1).

EXAMPLE 31

1-(2-methoxyphenyl)-1-oxo-2-aza-4-hydroxyethyl-4-(4-aza-3-oxo-pentanyl)-4-phenylbutane

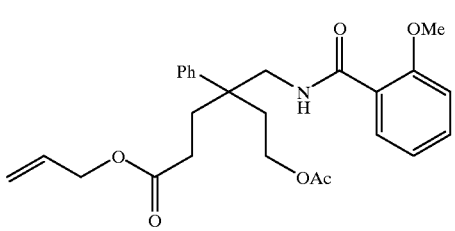

The title compound was prepared (from 27.1 mg of 5-phenyl-4-(3-(2-methoxyophenyl)3-oxo-2-aza-propyl)-1-oxy-2-oxocycloheptane (0.077 mmol) according to procedures described in Example 28 with the exception that the reaction was carried out in a solution of 2M methylamine in THF.

$^1$H NMR (CDCl$_3$) δ 8.25 (t, 1H, J=5.7 Hz), 8.12 (d, 1H, J=6.8 Hz); 7.42 (t, 1H, J=7.0 Hz), 7.32–7.36 (m, 4H), 7.21–7.23 (m, 1H), 7.04 (t, 1H, J=7.3 Hz), 6.89 (d, 1H, J=8.2 Hz), 6.60 (q, 1H, J=4.1 Hz), 3.89 (d, 2H, J=6.2 Hz), 3.68 (s, 3H), 3.58–3.62 (m, 1H), 3.41–3.46 (m, 1H), 3.25 (bs, 1H), 2.66 (d, 4.8 Hz), 1.89–2.18 (m, 6H); Mass Spectrum (CI) m/e 385 (M+1)

EXAMPLE 32

1-(2-methoxyphenyl)-1-oxo-2-aza-4,4-diphenylbutane

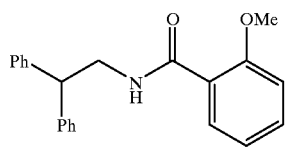

To a solution of 0.106 gm (0.58 mmol) of 1-amino diphenylmethane in 5 mL of dichloromethane and 0.1 mL of pyridine (1.16 mmol) at 0° C. was added 0.198 gm of 2-methoxybenzoyl chloride (0.172 mL, 1.16 mmol). The reaction was allowed to warm to rt and was stirred for 4 hr. The reaction mixture was concentrated, 5 mL of heptane were added and the mixture was evaporated to dryness this being repeated one more time. The residue was purified by HPLC (RCM SepPak, silica 25×100, 1.25% $CH_3CN$, 5% $tBuOCH_3$, 93.75% hexane) to give the title compound.

$^1$H NMR (500 MHz, $CDCl_3$) δ 3.95 (s, 3H), 6.58 (d, 1H), 7.01 (d, 1H), 7.06 (t, 1H), 7.25–7.50 (m, 9H), 8.2 (d, 1H), 8.7 (d, 1H); $^{13}$C NMR ($CDCl_3$) δ 55.82, 57.15, 164.16; Mass Spectrum m/e 318 ($M^+$1).

The following examples 33 to 37 were prepared as described in Examples 3 and 2.

EXAMPLE 33

1-(2-methoxyphenyl)-1-oxo-2-aza-4,4-diethyl-4-(2-methoxyphenyl)-butane

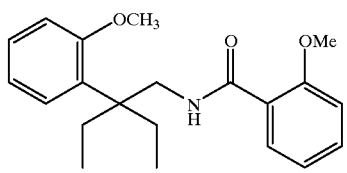

$^1$H NMR ($CDCl_3$) δ 0.8 (t, 6H), 1.8 (m, 2H), 2.0 (m, 2H), 3.5 (s, 3H), 3.85 (s, 3H), 4.0 (d, 2H), 6.83 (d, 1H), 6.94 (d, 1H), 6.98 (t, 1H), 7.04 (t, 1H), 7.28 (m, 1H), 7.31 (m, 1H), 7.37 (m, 1H), 7.6 (br s, 1H), 8.2 (dd, 1H). Mass Spectrum m/e 342 ($M^+$1).

EXAMPLE 34

1-(2-methoxyphenyl)-1-oxo-2-aza-4,4-diethyl-4-(3-methoxyphenyl)-butane

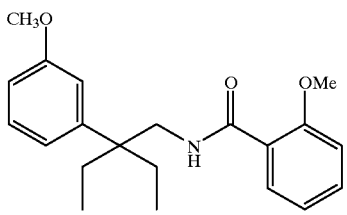

$^1$H NMR ($CDCl_3$) δ 0.8 (t, 6H), 1.78 (m, 4H), 3.6 (s, 3H), 3.76 (d, 2H), 3.83 (t, 3H), 6.8 (dd, 1H), 6.86 (d, 1H), 6.97 (t, 1H), 7.02 (m, 1H), 7.04 (m, 1H), 7.32 (t, 1H), 7.4 (m, 1H), 7.66 (br s, 1H), 8.2 (dd, 1H). Mass Spectrum m/e 342 ($M^+$1).

EXAMPLE 35

1-(2-methoxyphenyl)-1-oxo-2-aza-4,4-diethyl-4-(4-methoxyphenyl)-butane

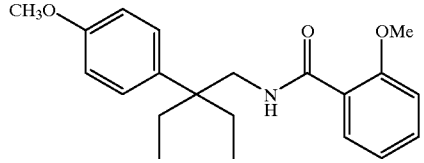

$^1$H NMR ($CDCl_3$) δ 0.8 (t, 6H), 1.76 (m, 4H), 3.6 (s, 3H), 3.77 (d, 2H), 3.83 (t, 3H), 6.88 (d, 1H), 6.94 (m, 2H), 7.05 (t, 1H), 7.32 (m, 2H), 7.4 (m, 1H), 7.65 (br s, 1H), 8.2 (dd, 1H). Mass Spectrum m/e 342 ($M^+$1).

EXAMPLE 36

1-(2-methoxyphenyl)-1-oxo-2-aza-4,4-diethyl-4-(2,4dimethylphenyl)-butane

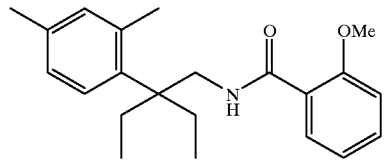

$^1$H NMR ($CDCl_3$) δ 0.8 (t, 6H), 2.2 (m, 4H), 3.4 (s, 3H), 4.2 (d, 2H), 6.78 (d, 1H), 7.02 (t, 1H), 7.36 (dt, 1H), 7.5 (m, 3H), 7.56 (d, 1H), 7.7 (br s, 1H), 7.8 (d, 1H), 7.92 (dd, 1H), 8.2 (dd, 1H), 8.55 (s, 1H). Mass Spectrum m/e 340 ($M^+$1).

EXAMPLE 37

1-(2-methoxyphenyl)-1-oxo-2-aza-4,4-diethyl-4-(naphth-1-yl)-butane

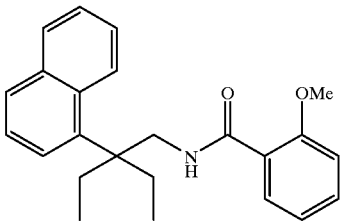

$^1$H NMR ($CDCl_3$) δ 0.8 (t, 6H), 1.76 (m, 4H), 2.3 (s, 3H), 2.5 (s, 3H), 3.5 (s, 3H), 3.9 (d, 2H), 6.84 (d, 1H), 7.02 (m, 1H), 7.05 (t, 1H), 7.25 (d, 1H), 7.39 (m, 1H), 7.7 (br s, 1H), 8.22 (dd, 1H). Mass Spectrum m/e 362 ($M^+$1).

EXAMPLE 38

1-(2-methoxyphenyl)-1-oxo-2-aza-4,4-diethyl-4-(4-acetylphenyl)-butane

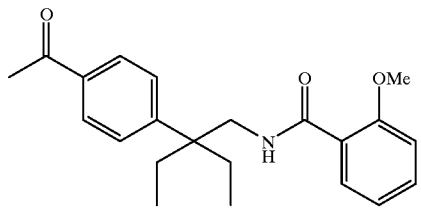

Step 1 2-(4-Tributyltinphenyl)acetonitrile

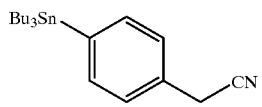

To a solution of 10 gm of 4-bromophenylacetonitrile (50 mmol) in 400 mL THF at −90° C. was added 100 mL of t-butyl lithium (1 M in hexanes 170 mmol). To this was added a solution of 19.5 gm of tributyltin chloride (60 mmol) in 10 mL THF and the reaction mixture was allowed to warm to −70° C. The reaction mixture was stirred for 30 min and then poured into 400 mL water. The reaction mixture was extracted with 500 mL of 1:1 ether-hexanes and the layers were separated. The organic layer was washed with water and brine, dried over $Na_2SO_4$, filtered and concentrated. The residue was purified by chromatography (silica, 30% ether-hexanes) to afford the title compound as a colorless oil.

$^1$H NMR (CDCl$_3$) δ 0.80 (t, 9H), 1.06 (m, 6H), 1.32 (m, 6H), 1.52 (m, 6H), 3.73 (s, 2H), 7.28 (d, 2H), 7.47 (d, 2H).

Step 2 2-(4-Tributyltinphenyl)-2,2-diethylacetonitrile

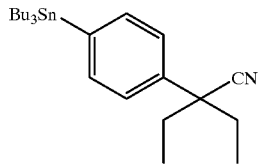

To a solution of 10.1 gm of 2-(4-tributyltinphenyl)acetonitrile (Step 1, 25 mmol) in 250 mL of tetrahydrofuran at −20° C. was added 75 mL t-BuOK (1M in t-butanol, 75 mmol), and the reaction mixture was stirred for 5 min. To the reaction mixture was then added 10.1 gm of ethyl iodide (65 mmol) and stirring was continued for 1 hr as the temperature was warmed to rt. The reaction mixture was then partitioned between NH$_4$Cl (sat) and ether. The organic fraction was washed with H$_2$O, brine, dried over Na$_2$SO$_4$, filtered and concentrated. The residue was purified by chromatography (silica, 5–15% ether-hexane) to afford the title compound as a colorless oil.

$^1$H NMR (CDCl$_3$) δ 0.80–0.95 (m, 15H), 1.06 (m, 6H), 1.32 (m, 6H), 1.52 (m, 6H), 1.82–2.05 (m, 4H), 7.28 (m, 2H), 7.47 (m, 2H).

Step 3 2-(4-tributyltinphenyl)-(2,2-diethyl)ethylamine

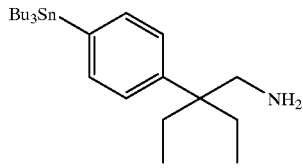

To a solution of 0.3 gm of 2-(4-Tributyltinphenyl)-2,2-diethylacetonitrile (Step 2, (1.1 mmol) ) in 5 mL of MeOH and 0.5 mL of THF was added 0.1 gm (0.78 mmol) of CoCl$_2$. After stirring for for 5 min., 0.065 of NaBH$_4$ (1.75 mmol) was added portionwise over 3 hrs. When the reaction was complete (TLC 90:10:1 CHCl$_3$—MeOH—NH4OH), it was partitioned between NH$_4$Cl (sat) and ether. The organic fraction was washed with water and brine, dried over Na$_2$SO$_4$, filtered and concentrated. The residue was used without further purification.

Step 4 1-(2-methoxyphenyl)-1-oxo-2-aza-4,4-diethyl-4-(4-tributyltinphenyl)-butane

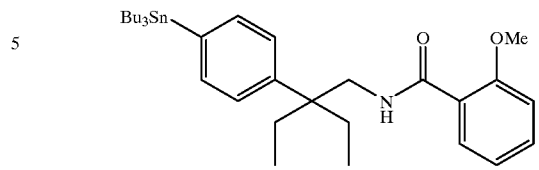

To a solution of 2-(4-tributyltinphenyl)-(2,2-diethyl)ethylamine (~1 mmol) in 5 mL dichloromethane was added 0.12 mL of pyridine (3 mmol), 0.024 gm of DMAP (0.2 mmol) and 0.34 gm of o-anisoyl chloride (2 mmol). After stirring for 1 hr, the reaction mixture was partitioned between ethyl ether and water. The organic fraction was washed with water and brine, dried over NaSO$_4$, filtered and concentrated. The residue was purified by chromatography (silica, 20–25% ether-hexane) to afford the title compound as a colorless oil.

$^1$H NMR (CDCl$_3$) δ 0.82 (t, 6H), 0.91 (t, 9H), 1.07 (t, 6H), 1.36(m, 6H), 1.56 (m, 6H), 1.79 (q, 4H), 3.62 (s, 3H), 3.77 (d, 2H), 6.84 (d, 1H), 7.04 (t, 1H), 7.35–7.40 (m, 3H), 7.49 (d, 2H) 7.68 (br s, 1H), 8.21 (dd, 1H).

Step 5 1-(2-methoxyphenyl)-1-oxo-2-aza-4,4-diethyl-4-(4-acetylphenyl)-butane

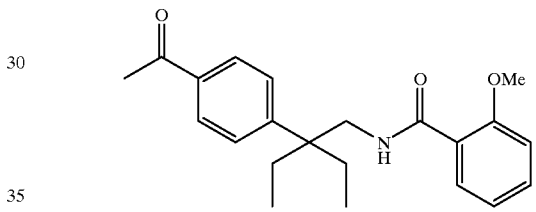

To a solution of 0.24 gm of 1-(2-methoxyphenyl)-1-oxo-2-aza-4,4-diethyl-4-(4-tributyltinphenyl)butane (0.04 mmol) in 1 mL of dichloromethane was added 4 mg triethylamine (0.04 mmol), 0.01 gm of K$_2$CO$_3$, 0.002 gm, Pd$_2$(dba)$_3$-CHCl$_3$ (5 mole %) and 0.004 gm of acetyl chloride (0.05 mmol), the reaction mixture was stirred for 4 hr at ambient temperature. The reaction mixture was partitioned between water and ether and the organic fraction was dried over MgSO$_4$, filtered and concentrated. The residue was purified by HPLC (Waters RCM, Nova-Pak silica, 8 mm×10 cm, using a mixture of 2:1 (6:3:1 hexane-methyl tert-butyl ether-acetonitrile:hexane) to afford the title compound.

$^1$H NMR (CDCl$_3$) δ 0.82 (t, 6H), 1.83 (m, 4H), 2.63 (s, 3H), 3.60 (s, 3H), 3.84 (d, 2H), 6.86 (d, 1H), 7.06 (t, 1H), 7.40(m, 1H), 7.52 (d, 2H) 7.65 (m, 1H), 7.99 (m, 2H), 8.22 (dd, 1H) Mass Spectrum (CI) m/e 354 (M+1)

EXAMPLE 39

1-(2-methoxyphenyl)-1-oxo-2-aza-4,4-diethyl-4-(4-bromophenyl)-butane

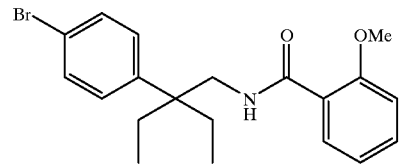

To a solution of 0.24 of 1-(2-methoxyphenyl)-1-oxo-2-aza-4,4-diethyl-4-(4-tributyltinphenyl)-butane (0.04 mmol)

in 1 mL dichloromethane was added 0.008 gm triethylamine (0.08 mmol) and 0.08 mL of a 1M solution of bromine in dichloromethane. After stirring for 15 min., the reaction was quenched with water and a drop of sat. NaHSO$_3$. The organic fraction was dried over MgSO$_4$, filtered and concentrated. The residue was purified by HPLC (Waters RCM, Nova-Pak silica, 8 mm×10 cm) using a mixture of 2:1 (6:3:1 hexane-methyl tert-butyl ether-acetonitrile:hexane) to afford the title compound.

$^1$H NMR (CDCl$_3$) δ 0.81 (t, 6H), 1.76 (m, 4H), 3.62 (s, 3H), 3.77 (d, 2H), 6.87 (d, 1H), 7.06 (t, 1H), 7.29 (d, 2H), 7.40(m, 1H), 7.52 (d, 2H) 7.63 (br s, 1H), 8.22 (dd, 1H). d Mass Spectrum (CI) m/e 390,392 (M+1).

EXAMPLE 40

1-(2-methoxyphenyl)-1-oxo-2-aza-4,4-diethyl-4-(3-acetylphenyl) butane

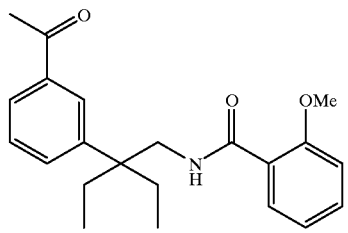

The title compound was prepared from 3-bromophenyl acetonitrile according to procedures described in Example 38.

$^1$N NMR (CDCl$_3$) δ 0.81 (t, 6H), 1.85 (m, 4H), 2.63 (s, 3H), 3.59 (s, 3H), 3.84 (d, 2H), 6.86 (d, 1H), 7.06 (t, 1H), 7.40(m, 1H), 7.50 (d, 1H) 7.64 (m, 2H), 7.86 (m, 1H), 8.03 (m, 1H), 8.22 (dd, 1H) Mass Spectrum (CI) m/e 354 (M+1)

EXAMPLE 41

1-(2-methoxyphenyl)-1-oxo-2-aza-4,4-diethyl-4-(3-bromophenyl)-butane

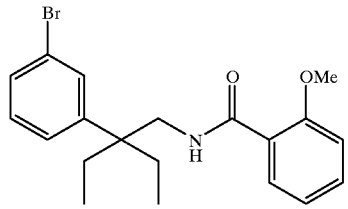

The title compound was prepared from 1-(2-methoxyphenyl)-1-oxo-2-aza-4,4-diethyl-4-(3-tributyltinphenyl)-butane according to procedures described in Example 39.

$^1$H NMR (CDCl$_3$) δ 0.82 (t, 6H), 1.78 (m, 4H), 3.65 (s, 3H), 3.77 (d, 2H), 6.88 (d, 1H), 7.06 (t, 1H), 7.28 (m, 1H), 7.35–7.45 (m, 3H), 7.55 (m, 1H) 7.63 (br s, 1H), 8.22 (dd, 1H). d Mass Spectrum (CI) m/e 390,392 (M+1)

EXAMPLE 42

1-(2-methoxy-5-bromophenyl)-1-oxo-2-aza-4,4-diethyl-4-(3-bromophenyl) butane

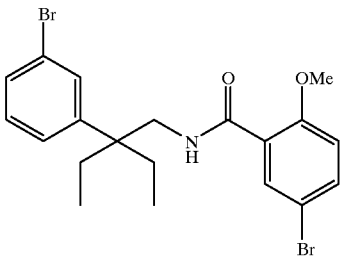

To a solution of 0.024 gm of 1-(2-methoxyphenyl)-1-oxo-2-aza-4,4-diethyl-4-(3-tributyltinphenyl)-butane (0.04 mmol) in 1 mL of dichloromethane was added 0.008 gm of triethylamine (0.08 mmol) and 1.2 mL of a 1M solution of bromine in dichloromethane. After stirring for 45 min. the reaction mixture was partitioned into water and a drop of sat. NaHSO$_3$. The organic fraction was dried over MgSO$_4$, filtered and concentrated. The residue was purified by HPLC (Waters RCM, Nova-Pak silica, 8 mm×10 cm) using a mixture of 2:1 (6:3:1 hexane-methyl tert-butyl ether-acetonitrile:hexane) to afford the title compound.

$^1$H NMR (CDCl$_3$) δ 0.82 (t, 6H), 1.77 (m, 4H), 3.63 (s, 3H), 3.75 (d, 2H), 6.77 (d, 1H), 7.28 (t, 1H), 7.35 (d, 1H), 7.42 (d, 1H), 7.49 (dd, 1H), 7.50–7.56 (br m, 2H), 8.32 (dd, 1H). d Mass Spectrum (CI) m/e

EXAMPLE 43

1-(2,3-dihydrobenzofuran-7-yl)-1-oxo-2-aza-4,4-diethyl-4-(phenyl)-butane

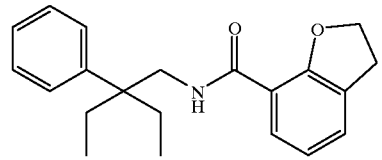

Step 1 1-(2,3-dihydrobenzofuran-7-yl)-1-oxo-2-aza-4,4-diethyl-4-(4-tributyltinphenyl)-butane

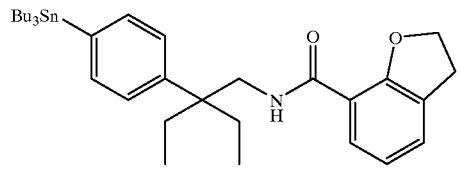

To a solution of 2-(4-tributyltinphenyl)-(2,2-diethyl) ethylamine (Example 38, Step 3, ~1 mmol) in 5 mL dichloromethane was added 0.12 mL pyridine (3 mmol), 0.024 gm of DMAP (0.2 mmol) and 0.36 gm of 7-dihydrobenzofuranyl chloride (2 mmol) and the reaction mixture stirred for 1 hr. The mixture was partitioned between ethyl ether and water and the organic fraction was washed with water and brine, dried over NaSO$_4$ filtered and concentrated. The residue was purified by chromatography (silica, 20–25% ether-hexane) to afford the title compound as a colorless oil.

$^1$H NMR (CDCl$_3$) δ 0.82 (t, 6H), 0.91 (t, 9H), 1.07 (t, 6H), 1.36 (m, 6H), 1.56 (m, 6H), 1.79 (q, 4H), 3.17 (t, 2H), 3.77

(d, 2H), 4.43 (t, 2H), 6.92 (t, 1H), 7.32–7.40 (m, 3H), 7.50 (d, 2H) 7.69 (br s, 1H), 7.91 (dd, 1H)

Step 2 1-(2,3-dihydrobenzofuran-7-yl)-1-oxo-2-aza-4,4-diethyl-4-(phenyl)-butane

A solution of 0.025 gm 1-(2,3-dihydrobenzofuran-7-yl)-1-oxo-2-aza-4,4-diethyl-4-(4-tributyltinphenyl)-butane (0.04 mmol) in 1 mL dichloromethane and 0.1 mL of 1M HCl in ether was stirred for 15 min. The reaction mixture was partitioned between 5 mL ether and 2 mL of sat. Na$_2$CO$_3$ and organic fraction was washed with water and brine, dried over NaSO$_4$ filtered and concentrated. The residue was purified by HPLC (Waters RCM, Nova-Pak silica, 8 mm×10 cm) using a mixture of 2:1 (6:3:1 hexane-methyl tert-butyl ether-acetonitrile:hexane) to afford the title compound.

$^1$H NMR (CDCl$_3$) δ 0.81 (t, 6H), 1.80 (m, 4H), 3.17 (t, 2h), 3.76 (d, 2H), 4.44 (t, 2H), 6.93 (t, 1H), 7.26 (m, 2H), 7.32–7.42 (m, 5H), 7.9 (d, 1H). d Mass Spectrum (CI) m/e 324 (M+1)

EXAMPLE 44
1-(2,3-dihydrobenzofuran-7-yl)-1-oxo-2-aza-4,4-diethyl-4-(phenyl)-butane

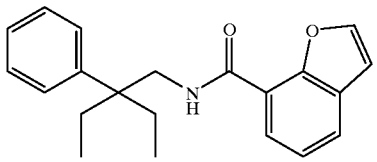

A solution of 0.12 gm of 1-(2,3-dihydrobenzofuran-7-yl)-1-oxo-2-aza-4,4-diethyl-4-(phenyl)-butane (0.02 mmol) in n-propanol and 5% Pd/C was stirred at reflux for 3 hr. The reaction mixture was cooled, filtered and concentrated. The residue was purified by HPLC (Waters RCM, Nova-Pak silica, 8 mm×10 cm) using a mixture of 2:1 (6:3:1 hexane-methyl tert-butyl ether-acetonitrile:hexane) to afford the title compound.

$^1$H NMR (CDCl$_3$) δ 0.85 (t, 6H), 1.86 (m, 4H), 3.17 (t, 2H), 3.86 (d, 2H), 6.79 (d, 1H), 7.26 (m, 2H), 7.32–7.42 (m, 5H), 7.9 (d, 1H) d Mass Spectrum (CI) m/e 326 (M+1)

EXAMPLE 45
1-(2,3-dihydrobenzofuran-7-yl)-1-oxo-2-aza-4,4-diethyl-4-(3-acetylphenyl)-butane

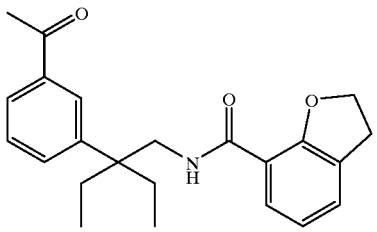

The title compound was prepared from 1-(2,3-dihydro benzofuran-7-yl)-1-oxo-2-aza-4,4-diethyl-4-(3-tributyltinphenyl)-butane according to procedures described in Examples 38 and 40.

$^1$H NMR (CDCl$_3$) δ 0.81 (t, 6H), 1.85 (m, 4H), 2.63 (s, 3H), 3.19 (t, 2H), 3.80 (d, 2H), 4.42 (t, 2H), 6.93 (d, 1H), 7.24–7.36 (m, 3H), 7.48 (t, 1H) 7.63 (m, 1H), 7.86 (dd, 1H) 8.02 (m, 1H), Mass Spectrum (CI) m/e 366 (M+1)

EXAMPLE 46
1-(2,3-dihydrobenzofuran-7-yl)-1-oxo-2-aza-4,4-diethyl-4-(3-bromophenyl)-butane

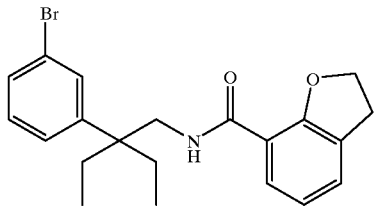

The title compound was prepared from 1-(2,3-dihydrobenzofuran-7-yl)-1-oxo-2-aza-4,4-diethyl-4-(3-tributyltinphenyl)-butane according to procedures described in Example 41.

$^1$H NMR (CDCl$_3$) δ 0.81 (t, 6H), 1.79 (m, 4H), 3.20 (t, 2h), 3.73 (d, 2H), 4.56 (t, 2H), 6.93 (t, 1H), 7.24–7.42 (m, 5H), 7.53 (m, 1H), 7.9 (d, 1H) . Mass Spectrum (CI) m/e 401,403 (m+1)

What is claimed is:

1. A compound of structural Formula I:

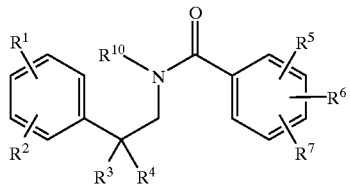

I or a pharmaceutically acceptable salt, crystal form, or hydrate, wherein:

n is: 0, 1, 2 or 3;

r is: 0 or 1;

s is: 0 or 1;

$R^1$, $R^2$, $R^5$, $R^6$ and $R^7$ are independently:
(1) halo, wherein halo is fluoro, chloro, bromo, or iodo,
(2) hydroxy,
(3) ($C_1$–$C_6$)-alkyl,
(4) HO($C_1$–$C_6$)-alkyloxy,
(5) ($C_1$–$C_4$)-perfluoroalkyl,
(6) ($C_2$–$C_6$)-alkenyl,
(7) ($C_2$–$C_6$)-alkynyl,
(8) O[(C=O)O$_r$]$_s$($C_1$–$C_6$)-alkyl, wherein the alkyl may be cyclic or straight-chained,
(9) ($C_1$–$C_6$)-alkyl-S(O)$_n$—,
(10) phenyl,
(11) phenoxy,
(12) cyano,
(13) nitro,
(14) CO$_2$H,
(15) CO($C_1$–$C_6$)-alkyl,
(16) CO$_2$($C_1$–$C_6$)-alkyl,
(17) CONR$^8$R$^9$,
(18) NR$^8$R$^9$,
(20) ($C_2$–$C_6$)-alkenyloxy,
(21) benzyloxy,
(22) hydrogen, or
(23) OCF$_3$;

$R^3$ and $R^4$ are independently:
(1) halo, wherein halo is fluoro, chloro, bromo, or iodo,
(2) hydroxy, (3) HO($C_1$–$C_6$)-alkyloxy,
(4) ($C_1$–$C_4$)-perfluoroalkyl,
(5) O(CO)CCl$_3$,
(6) ($C_1$–$C_6$)-alkyl-S(O)$_n$—,
(7) phenyl-(CH$_2$)$_r$-S(O)$_n$—,
(8) cyano,
(9) nitro,
(10) CO$_2$H,
(11) CO($C_1$–$C_6$)-alkyl,
(12) CO$_2$($C_1$–$C_6$)-alkyl,
(13) CONR$^8$R$^9$,
(14) NR$^8$R$^9$,
(15) O(CO)NR$^8$R$^9$,
(16) azido,
(17) NR$^8$(CO)NR$^8$R$^9$,
(18) hydrogen, provided that both R$^3$ and R$^4$ are not hydrogen,
(19) ($C_1$–$C_{10}$)-alkyl, wherein the alkyl is cyclic or acyclic and is unsubstituted or substituted with one or two of the substituents selected from the group consisting of:
  (a) halo, wherein halo is fluoro, chloro, bromo, or iodo,
  (b) hydroxy,
  (c) oxo,
  (d) O[(C=O)O$_r$]$_s$($C_1$–$C_6$)-alkyl,
  (e) ($C_1$–$C_6$)alkyl-S(O)$_n$—,
  (f) aryl-($C_1$–$C_6$)-alkyloxy,
  (g) cyano,
  (h) nitro,
  (i) vinyl,
  (j) NR$^8$R$^9$,
  (k) O(CO)NR$^8$R$^9$,
  (l) CHO,
  (m) CO$_2$H,
  (n) CO($C_1$–$C_6$)-alkyl,
  (o) CO$_2$($C_1$–$C_6$)-alkyl, wherein alkyl may be substituted with phenyl,
  (p) CONR$^8$R$^9$,
  (q) aryl, wherein aryl is defined as phenyl or naphthyl, unsubstituted or
  substituted with one, two or three of the substituents selected from the group consisting of:
    (a') halo, as defined above,
    (b') hydroxy,
    (c') ($C_1$–$C_6$)-alkyl,
    (d') ($C_1$–$C_4$)-perfluoroalkyl,
    (e') ($C_2$–$C_6$)-alkenyl,
    (f') ($C_2$–$C_6$)-alkynyl,
    (g') ($C_1$–$C_6$)-alkyloxy,
    (h') ($C_1$–$C_6$)-alkyl-S(O)$_n$—,
    (i') phenyl,
    (j') phenoxy,
    (k') cyano,
    (l') nitro,
    (m') CO$_2$H,
    (n') CO($C_1$–$C_6$)-alkyl,
    (o') CO$_2$($C_1$–$C_6$)-alkyl,
    (p') CONR$^8$R$^9$,
    (q') NR$^8$R$^9$, and
  (s) heterocyclyl, wherein heterocyclyl is defined as a 3 to 7 atom cyclic, non-aromatic substituent containing from 1 to 3 heteroatoms selected from the group consisting of O, N, and S, said heterocycle being unsubstituted or substituted with one, two or three substituents selected from the group consisting of:
    (a') halo, as defined above,
    (b') hydroxy,
    (c') ($C_1$–$C_6$)-alkyl,
    (d') ($C_1$–$C_4$)-perfluoroalkyl,
    (e') ($C_2$–$C_6$)-alkenyl,
    (f') ($C_2$–$C_6$)-alkynyl,
    (g') ($C_1$–$C_6$)-alkyloxy,
    (h') ($C_1$–$C_6$)-alkyl-S(O)$_n$—,
    (i') phenyl,
    (j') phenoxy,
    (k') cyano,
    (l') nitro,
    (m') CO$_2$H,
    (n') CO($C_1$–$C_6$)-alkyl,
    (o') CO$_2$($C_1$–$C_6$)-alkyl,
    (p') CONR$^8$R$^9$,
    (q') NR$^8$R$^9$,
    (r') NR$^8$CO($C_1$–$C_6$)-alkyl,
    (s') oxo, and
    (t') fused benzo,
  (t) benzyl-S(O)$_n$—,
  (u) O[(C=O)O$_r$]$_s$($C_2$–$C_6$)-alkenyl,
  (v) O[(C=O)O$_r$]$_s$aryl, or
  (w) O(CH$_2$)$_n$aryl;
(20) ($C_2$–$C_{10}$)-alkenyl, wherein alkenyl is unsubstituted or substituted with one or two of the substituents selected from the group consisting of:
  (a) halo, wherein halo is fluoro, chloro, bromo, or iodo,
  (b) hydroxy,
  (c) oxo,
  (e) ($C_1$–$C_6$)-alkyl-S(O)$_n$—,
  (f) phenyl-($C_1$–$C_6$)-alkyloxy,
  (g) cyano,
  (h) nitro,
  (i) NR$^8$R$^9$,
  (j) CHO,
  (k) CO$_2$H,
  (l) CO($C_1$–$C_6$)-alkyl,
  (m) CO$_2$($C_1$–$C_6$)-alkyl,
  (n) CONR$^8$R$^9$,
  (o) aryl, wherein aryl is as defined above,
  (p) heterocyclyl, wherein heterocyclyl is as defined above,
  (q) O[(C=O)O$_r$]$_s$($C_1$–$C_6$)-alkyl, alkyl as defined above,
  (r) O[(C=O)O$_r$]$_s$($C_2$–$C_6$)-alkenyl, as defined above,
  (s) O[(C=O)O$_r$]$_s$aryl, aryl as defined above, and
  (t) O(CH$_2$)$_n$aryl, aryl as defined above;
(21) ($C_2$–$C_{10}$)-alkynyl, wherein alkynyl is unsubstituted or substituted with one or two of the substituents selected from the group consisting of:
  (a) halo, wherein halo is fluoro, chloro, bromo, or iodo,
  (b) hydroxy,
  (c) oxo,
  (d) ($C_1$–$C_6$)-alkyloxy,
  (e) ($C_1$–$C_6$)-S(O)$_n$—,
  (f) phenyl-($C_1$–$C_6$)-alkyloxy,
  (g) cyano,
  (h) nitro,
  (i) vinyl,
  (j) NR$^8$R$^9$,
  (k) NR$^8$CO($C_1$–$C_6$)-alkyl,
  (l) CHO,
  (m) CO$_2$H,
  (n) CO($C_1$–$C_6$)-alkyl, (o) $CO_2C(C_1-C_6)$-alkyl,
(p) $CONR^8R^9$,
(q) aryl, wherein aryl is as defined above,
(r) heterocyclyl, wherein heterocyclyl is as defined above,
(s) $O[(C=O)O_r]_s(C_1-C_6)$-alkyl, alkyl as defined above,
(t) $O[(C=O)O_r]_s(C_2-C_6)$-alkenyl, as defined above,
(u) $O[(C=O)O_r]_s$aryl, aryl as defined above,
(v) $O(CH_2)_n$aryl, aryl as defined above,
(22) $O[(C=O)O_r]_s(C_1-C_6)$-alkyl, alkyl as defined above,
(23) $O[(C=O)O_r]_s(C_2-C_6)$-alkenyl, as defined above,
(24) $O[(C=O)O_r]_s$aryl, aryl as defined above,
(25) aryl, wherein aryl is as defined above or
(26) $O(CH_2)_n$aryl, aryl as defined above;
$R^3$ can also be any of the following when $R^4$ is absent:
(29) oxo,
(30) $=CH$-$(C_1-C_6)$-alkyl, wherein alkyl is as defined above,
(31) $=CH$-$(C_2-C_6)$-alkenyl, wherein alkenyl is as defined above,
(32) $=CH$-aryl, wherein aryl is as defined above, or
(33) $=CH_2$;
$R^8$ and $R^9$ are independently selected from the group consisting of:
(1) hydrogen,
(2) $[(C=O)O_r]_s$aryl, wherein aryl is as defined above,
(3) $[(C=O)O_r]_s(C_2-C_8)$-alkenyl, wherein alkenyl is as defined above,
(4) $[(C=O)O_r]_s(C_1-C_8)$-alkyl, wherein alkyl is as defined above,
(5) $(C=O)_rS(O)_n(C_1-C_8)$-alkyl, wherein alkyl is as defined above,
(6) $(C=O)_rS(O)_n$-aryl, wherein aryl is as defined above, and
(7) heterocyclyl, wherein heterocyclyl is defined above;
$R^{10}$ is:
(1) hydrogen,
(2) $[(C=O)O_r]_s$aryl, wherein aryl is as defined above, or
(3) $[(C=O)O_r]_s(C_1-C_6)$-alkyl, wherein alkyl is as defined above.

2. The Compound of claim 1, wherein:
$R^3$ and $R^4$ are independently:
(1) halo, wherein halo is fluoro, chloro, bromo, or iodo,
(2) hydroxy,
(3) $HO(C_1-C_6)$-alkyloxy,
(4) $(C_1-C_4)$-perfluoroalkyl,
(5) $O(CO)CCl_3$,
(6) $(C_1-C_6)$-alkyl-$S(O)_n$—,
(7) phenyl-$(CH_2)_rS(O)_n$—,
(8) cyano,
(9) nitro,
(10) $CO_2H$,
(11) $CO(C_1-C_6)$-alkyl,
(12) $CO_2(C_1-C_6)$-alkyl,
(13) $CONR^8R^9$,
(14) $NR^8R^9$,
(15) $O(CO)NR^8R^9$,
(16) azido,
(17) $NR^8(CO)NR^8R^9$,
(18) hydrogen, provided that both $R^3$ and $R^4$ are not hydrogen,
(19) $(C_1-C_6)$-alkyl, wherein the alkyl is cyclic or acyclic groups and is unsubstituted or substituted with one or two of the substituents selected from the group consisting of:
(a) halo, wherein halo is fluoro, chloro, bromo, or iodo,
(b) hydroxy,
(c) oxo,
(d) $O[(C=O)O_r]_s(C_1-C_6)$-alkyl,
(e) $(C_1-C_6)$-alkyl-$S(O)_n$—,
(f) aryl-$(C_1-C_6)$-alkyloxy,
(g) cyano,
(h) nitro,
(i) vinyl,
(j) $NR^8R^9$,
(k) $O(CO)NR^8R^9$,
(l) CHO,
(m) $CO_2H$,
(n) $CO(C_1-C_6)$-alkyl,
(o) $CO_2(C_1-C_6)$-alkyl, wherein alkyl may be substituted with phenyl,
(p) $CONR^8R^9$,
(q) aryl, wherein aryl is defined as phenyl or naphthyl, unsubstituted or substituted with one, two or three of the substituents selected from the group consisting of:
(a') halo, as defined above,
(b') hydroxy,
(c') $(C_1-C_6)$-alkyl,
(d') $(C_1-C_4)$-perfluoroalkyl,
(e') $(C_2-C_6)$-alkenyl,
(f') $(C_2-C_6)$-alkynyl,
(g') $(C_1-C_6)$-alkyloxy,
(h') $(C_1-C_6)$-alkyl-$S(O)_n$—,
(i') phenyl,
(j') phenoxy,
(k') cyano,
(l') nitro,
(m') $CO_2H$,
(n') $CO(C_1-C_6)$-alkyl,
(o') $CO_2(C_1-C_6)$-alkyl,
(p') $CONR^8R^9$,
(q') $NR^8R^9$, and
(r) heterocyclyl, wherein heterocyclyl is defined as a 3 to 7 atom cyclic, non-aromatic substituent containing from 1 to 3 heteroatoms selected from the group consisting of O, N, and S, said heterocycle being unsubstituted or substituted with one, two or three substituents selected from the group consisting of:
(a') halo, as defined above,
(b') hydroxy,
(c') $(C_1-C_6)$-alkyl,
(d') $(C_1-C_4)$-perfluoroalkyl,
(e') $(C_2-C_6)$-alkenyl,
(f') $(C_2-C_6)$-alkynyl,
(g') $(C_1-C_6)$-alkyloxy,
(h') $(C_1-C_6)$-alkyl-$S(O)_n$—,
(i') phenyl,
(j') phenoxy,
(k') cyano,
(l') nitro,
(m') $CO_2H$,
(n') $CO(C_1-C_6)$-alkyl,
(o') $CO_2(C_1-C_6)$-alkyl,
(p') $CONR^8R^9$,
(q') $NR^8R^9$,
(r') $NR^8CO(C_1-C_6)$-alkyl,
(s') oxo, and
(t') fused benzo;

(t) benzyl-S(O)$_n$—,
(u) O[(C=O)O$_r$]$_s$(C$_2$–C$_6$)-alkenyl,
(v) O[(C=O)O$_r$]$_s$aryl, or
(w) O(CH$_2$)$_n$aryl;
(20) (C$_2$–C$_6$)-alkenyl, wherein alkenyl is unsubstituted or substituted with one or two of the substituents selected from the group consisting of:
   (a) halo, wherein halo is fluoro, chloro, bromo, or iodo,
   (b) hydroxy,
   (c) oxo,
   (e) (C$_1$–C$_6$)-alkyl-S(O)$_n$—,
   (f) phenyl-(C$_1$–C$_6$)-alkyloxy,
   (g) cyano,
   (h) nitro,
   (i) NR$^8$R$^9$,
   (j) CHO,
   (k) CO$_2$H,
   (l) CO(C$_1$–C$_6$)-alkyl,
   (m) CO$_2$(C$_1$–C$_6$)-alkyl,
   (n) CONR$^8$R$^9$,
   (o) aryl, wherein aryl is as defined above,
   (p) heterocyclyl, wherein heterocyclyl is as defined above,
   (q) O[(C=O)O$_r$]$_s$(C$_1$–C$_6$)-alkyl, alkyl as defined above,
   (r) O[(C=O)O$_r$]$_s$(C$_2$–C$_6$)-alkenyl, as defined above,
   (s) O[(C=O)O$_r$]$_s$aryl, aryl as defined above, and
   (t) O(CH$_2$)nary, aryl as defined above;
(21) (C$_2$–C$_6$)-alkynyl, wherein alkynyl is unsubstituted or substituted with one or two of the substituents selected from the group consisting of:
   (a) halo, wherein halo is fluoro, chloro, bromo, or iodo,
   (b) hydroxy,
   (c) oxo,
   (d) (C$_1$–C$_6$)-alkyloxy,
   (e) (C$_1$–C$_6$)-S(O)$_n$—,
   (f) phenyl-(C$_1$–C$_6$)-alkyloxy,
   (g) cyano,
   (h) nitro,
   (i) vinyl,
   (j) NR$^8$R$^9$,
   (k) NR$^8$CO(C$_1$–C$_6$)-alkyl,
   (l) CHO,
   (m) CO$_2$H,
   (n) CO(C$_1$–C$_6$)-alkyl,
   (o) CO$_2$C(C$_1$–C$_6$)-alkyl,
   (p) CONR$^8$R$^9$,
   (q) aryl, wherein aryl is as defined above,
   (r) heterocyclyl, wherein heterocyclyl is as defined above,
   (s) O[(C=O)O$_r$]$_s$(C$_1$–C$_6$)-alkyl, alkyl as defined above,
   (t) O[(C=O)O$_r$]$_s$(C$_2$–C$_6$)-alkenyl, as defined above,
   (u) O[(C=O)O$_r$]$_s$aryl, aryl as defined above, and
   (v) O(CH$_2$)$_n$aryl, aryl as defined above,
(22) O[(C=O)O$_r$]$_s$(C$_1$–C$_6$)-alkyl, alkyl as defined above,
(23) O[(C=O)O$_r$]$_s$(C$_2$–C$_6$)-alkenyl, as defined above,
(24) O[(C=O)O$_r$]$_s$aryl, aryl as defined above,
(25) aryl, wherein aryl is as defined above or
(26) O(CH$_2$)$_n$aryl, aryl as defined above;
R$^3$ can also be any of the following when R$^4$ is absent:
(29) oxo,
(30) =CH-(C$_1$–C$_6$)-alkyl, wherein alkyl is as defined above,
(31) =CH-(C$_2$–C$_6$)-alkenyl, wherein alkenyl is as defined above,
(32) =CH-aryl, wherein aryl is as defined above, or
(33) =CH$_2$.

3. The compound of claim 2, wherein:
R$^1$, R$^2$, R$^5$, R$^6$ and R$^7$ are independently:
   (1) halo, wherein halo is fluoro, chloro, bromo, or iodo,
   (2) hydroxy,
   (3) (C$_1$–C$_6$)-alkyl,
   (4) HO(C$_1$–C$_6$)-alkyloxy,
   (5) (C$_1$–C$_4$)-perfluoroalkyl,
   (6) (C$_2$–C$_6$)-alkenyl,
   (7) O[(C=O)O$_r$]$_s$(C$_1$–C$_6$)-alkyl, wherein the alkyl may be cyclic or straight-chained,
   (8) phenyl,
   (9) CO(C$_1$–C$_6$)-alkyl,
   (10) CO$_2$(C$_1$–C$_6$)-alkyl,
   (11) CONR$^8$R$^9$,
   (12) NR$^8$R$^9$,
   (13) (C$_2$–C$_6$)-alkenyloxy,
   (14) benzyloxy,
   (15) hydrogen, or
   (16) OCF$_3$;
R$^3$ and R$^4$ are independently:
   (1) halo, wherein halo is fluoro, chloro, bromo, or iodo,
   (2) hydroxy,
   (3) HO(C$_1$–C$_6$)-alkyloxy,
   (4) (C$_1$–C$_4$)-perfluoroalkyl,
   (5) O(CO)CCl$_3$,
   (6) (C$_1$–C$_6$)-alkyl-S(O)$_n$—,
   (7) phenyl-(CH$_2$)$_r$S(O)$_n$—,
   (8) cyano,
   (9) nitro,
   (10) CO$_2$H,
   (11) CO(C$_1$–C$_6$)-alkyl,
   (12) CO$_2$(C$_1$–C$_6$)-alkyl,
   (13) CONR$^8$R$^9$,
   (14) NR$^8$R$^9$,
   (15) O(CO)NR$^8$R$^9$,
   (16) azido,
   (17) NR$^8$(CO)NR$^8$R$^9$,
   (18) hydrogen, provided that both R$^3$ and R$^4$ are not hydrogen,
   (19) (C$_1$–C$_6$)-alkyl, wherein the alkyl is cyclic or acyclic and is unsubstituted or substituted with one or two of the substituents selected from the group consisting of:
      (a) halo, wherein halo is fluoro, chloro, bromo, or iodo,
      (b) hydroxy,
      (c) oxo,
      (d) O[(C=O)O$_r$]$_s$(C$_1$–C$_6$)-alkyl,
      (e) aryl-(C$_1$–C$_6$)-alkyloxy,
      (f) NR$^8$R$^9$,
      (g) O(CO)NR$^8$R$^9$,
      (h) CHO,
      (i) CO$_2$H,
      (j) CO(C$_1$–C$_6$)-alkyl,
      (k) CO$_2$(C$_1$–C$_6$)-alkyl, wherein alkyl may be substituted with phenyl,
      (l) CO$_2$(C$_1$–C$_6$)-alkenyl,
      (m) CONR$^8$R$^9$,
      (n) aryl, wherein aryl is defined as phenyl or naphthyl, unsubstituted or substituted with a substituent selected from the group consisting of:
         (a') halo, as defined above,
         (b') hydroxy, (c') $(C_1-C_6)$-alkyl,
(d') $(C_1-C_6)$-alkyloxy,
(e') $(C_1-C_6)$-alkyl-S(O)$_n$—,
(f') phenyl,
(g') phenoxy,
(h') cyano,
(i') CO$_2$H,
(j') CO$(C_1-C_6)$-alkyl,
(k') CO$_2(C_1-C_6)$-alkyl,
(l') CONR$^8$R$^9$,
(m') NR$^8$R$^9$, and
(o) benzyl-S(O)$_n$—,
(p) O[(C=O)O$_r$]$_s$(C$_2$–C$_6$)-alkenyl,
(q) O[(C=O)O$_r$]$_s$aryl, or
(r) O(CH$_2$)$_n$aryl;
(20) $(C_2-C_6)$-alkenyl, wherein alkenyl is unsubstituted or substituted with a substituent selected from the group consisting of:
(a) halo, wherein halo is fluoro, chloro, bromo, or iodo,
(b) hydroxy,
(c) oxo,
(d) phenyl-$(C_1-C_6)$-alkyloxy,
(e) NR$^8$R$^9$,
(f) CHO,
(g) CO$_2$H,
(h) CO$(C_1-C_6)$-alkyl,
(i) CO$_2(C_1-C_6)$-alkyl,
(j) CONR$^8$R$^9$,
(k) aryl, wherein aryl is as defined above,
(l) O[(C=O)O$_r$]$_s$(C$_1$–C$_6$)-alkyl, alkyl as defined above,
(m) O[(C=O)O$_r$]$_s$aryl, aryl as defined above, or
(n) O(CH$_2$)$_n$aryl, aryl as defined above;
(21) O[(C=O)O$_r$]$_s$(C$_1$–C$_6$)-alkyl, alkyl as defined above,
(22) O[(C=O)O$_r$]$_s$(C$_2$–C$_6$)-alkenyl, as defined above,
(23) O[(C=O)O$_r$]$_s$aryl, aryl as defined above,
(24) aryl, wherein aryl is as defined above or
(25) O(CH$_2$)$_n$aryl, aryl as defined above;
R$^3$ can also be any of the following when R$^4$ is absent:
(28) oxo,
(29) =CH-$(C_1-C_6)$-alkyl, wherein alkyl is as defined above,
(30) =CH-$(C_2-C_6)$-alkenyl, wherein alkenyl is as defined above,
(31) =CH-aryl, wherein aryl is as defined above, or
(32) =CH$_2$;
R$^8$ and R$^9$ are independently selected from the group consisting of:
(1) hydrogen,
(2) [(C=O)O$_r$]$_s$aryl, wherein aryl is as defined above,
(3) [(C=O)O$_r$]$_s$(C$_2$–C$_8$)-alkenyl, wherein alkenyl is as defined above, and
(4) [(C=O)O$_r$]$_s$(C$_1$–C$_8$)-alkyl, wherein alkyl is as defined above, and
R$^{10}$ is:
(1) hydrogen, or
(2) [(C=O)O$_r$]$_s$(C$_1$–C$_6$)-alkyl, wherein alkyl is as defined above.

4. The compound of claim 3, wherein:
R$^1$, R$^2$, R$^5$, R$^6$ and R$^7$ are independently:
(1) halo, wherein halo is fluoro, chloro, bromo, or iodo,
(2) hydroxy,
(3) $(C_1-C_3)$-alkyl,
(4) $(C_2-C_3)$-alkenyl,
(5) O$(C_1-C_4)$-alkyl, wherein the alkyl may be cyclic or straight-chained,
(6) O(CO)CH$_3$,
(7) CO$(C_1-C_3)$-alkyl,
(8) CO$_2(C_1-C_3)$-alkyl, or
(9) hydrogen;
R$^3$ and R$^4$ are independently:
(1) hydrogen, provided that both R$^3$ and R$^4$ are not hydrogen,
(2) $(C_1-C_6)$-alkyl, wherein the alkyl is cyclic or acyclic and is unsubstituted or substituted with one or two of the substituents selected from the group consisting of:
(a) halo, wherein halo is fluoro, chloro, bromo, or iodo,
(b) hydroxy,
(c) oxo,
(d) O[(C=O)O$_r$]$_s$(C$_1$–C$_6$)-alkyl, wherein r and s are independently 0 or 1,
(e) CO$_2(C_2-C_3)$-alkenyl,
(f) O[(C=O)O$_r$]$_s$(C$_1$–C$_6$)-alkenyl, wherein r and s are independently 0 or 1,
(g) NR$^8$R$^9$,
(h) O(CO)NR$^8$R$^9$,
(i) CHO,
(j) CO$_2$H,
(k) CO$(C_1-C_6)$-alkyl,
(l) CO$_2(C_1-C_6)$-alkyl, wherein alkyl may be substituted with phenyl,
(m) CONR$^8$R$^9$,
(n) aryl, wherein aryl is defined as phenyl, unsubstituted or substituted with a substituent selected from the group consisting of:
(a') halo, as defined above,
(b') hydroxy,
(c') $(C_1-C_6)$-alkyl, and
(d') $(C_1-C_6)$-alkyloxy, and
(o) O[(C=O)O$_r$]$_s$(C$_2$–C$_6$)-alkenyl, wherein r and s are independently 0 or 1,
(3) $(C_2-C_6)$-alkenyl,
(4) aryl, wherein aryl is as defined above or
(5) O(CH$_2$)$_n$aryl, wherein aryl is as defined above;
R$^3$ can also be any of the following when R$^4$ is absent:
(6) =CH-$(C_1-C_6)$-alkyl, wherein alkyl is as defined above,
(7) =CH-$(C_2-C_6)$-alkenyl, wherein alkenyl is as defined above,
R$^8$ and R$^9$ are independently selected from the group consisting of:
(1) hydrogen,
(2) [(C=O)O$_r$]$_s$aryl, wherein aryl is as defined above and r and s are independently 0 or 1,
(3) $(C_2-C_8)$-alkenyl, wherein alkenyl is as defined above, and
(4) $(C_1-C_6)$-alkyl, wherein alkyl is as defined above, and
R$^{10}$ is:
(1) hydrogen, or
(2) (C=O)$(C_1-C_3)$-alkyl, wherein alkyl is as defined above.

5. A compound which is selected from the group consisting of:
1-(2-methoxyphenyl)-1-oxo-2-aza-(S)-4-i-butyl-4-phenylbutane,
1-(2-methoxyphenyl)-1-oxo-2-aza-4-(S)-((3-allyloxycarbonyloxy)propyl))-4-phenylbutane,
1-(2-methoxyphenyl)-1-oxo-2-aza-4,4-diethyl-4-phenylbutane, 1-(2,3-dihydrobenzofuran-7-yl)-1-oxo-2-aza-4,4-diethyl-4-(phenyl)-butane, and 1-(2-methoxyphenyl)-1-oxo-2-aza-4-(S)-(3-hydroxypropyl)-4-phenylbutane, or a pharmaceutically acceptable salt thereof.

6. A method of treating a condition in a mammal, the treatment of which is effected or facilitated by Kv1.3 inhibition, which comprises administering the compound of claim 1 in an amount that is effective at inhibiting Kv1.3.

7. A method of preventing or treating resistance to transplantation or transplantation rejection of organs or tissues in a patient in need thereof, which comprises administering a therapeutically effective amount of a compound of claim 1.

8. A method of suppressing the immune system in a subject in need thereof, which comprises administering to the subject an immune suppressing amount of a compound of claim 1.

9. A pharmaceutical formulation comprising a pharmaceutically acceptable carrier and the compound of claim 1 or a pharmaceutically acceptable crystal form or hydrate thereof.

10. A pharmaceutical composition made by combining the compound of claim 1 and a pharmaceutically acceptable carrier.

11. The pharmaceutical formulation of claim 9, comprising, in addition, a second immunosuppressive agent.

12. A pharmaceutical composition made by combining the compound of claim 1, pharmaceutically acceptable carrier, and a second immunosuppressive agent.

13. The pharmaceutical formulation as recited in claim 11 wherein the second immunosuppressive agent is selected from a group consisting of azathioprine, brequinar sodium, deoxyspergualin, mizaribine, mycophenolic acid morpholino ester, cyclosporin, FK-506 and rapamycin.

14. The method of claim 8, which comprises coadministering a second immunosuppressive agent.

15. A method of treating a condition in a mammal, the treatment of which is effected or facilitated by $K_v1.3$ inhibition, which comprises administering a pharmaceutical formulation comprising a pharmaceutical carrier and a compound of claim 1, in an amount that is effective at inhibiting $K_v1.3$.

16. A method of treating a condition in a mammal, the treatment of which is effected or facilitated by $K_v1.3$ inhibition, comprising coadministering a therapeutically effective amount of a compound of claim 1, with a second immunosuppressive agent.

17. A method of treating a condition in a mammal, the treatment of which is effected or facilitated by $K_v1.5$ inhibition, which comprises administering a compound of claim 1 in an amount that is effective at inhibiting $K_v1.5$.

18. A method of treating a condition in a mammal, the treatment of which is effected or facilitated by $K_v1.5$ inhibition, which comprises administering a pharmaceutical formulation comprising a pharmaceutical carrier and a compound of claim 1, in an amount that is effective at inhibiting $K_v1.5$.

19. A method of preventing or treating cardiac arrhythmias in a mammal, which comprises administering a therapeutically effective amount of a compound of claim 1.

* * * * *